(12) United States Patent
Mandell et al.

(10) Patent No.: US 6,560,542 B1
(45) Date of Patent: May 6, 2003

(54) ALGORITHMIC DESIGN OF PEPTIDES FOR BINDING AND/OR MODULATION OF THE FUNCTIONS OF RECEPTORS AND/OR OTHER PROTEINS

(75) Inventors: Arnold J. Mandell, Asheville, NC (US); Karen A. Selz, Asheville, NC (US); Michael F. Shlesinger, Rockville, MD (US)

(73) Assignee: The Cielo Institute, Asheville, NC (US)

( * ) Notice: Subject to any disclaimer, the term of this patent is extended or adjusted under 35 U.S.C. 154(b) by 0 days.

(21) Appl. No.: 09/490,702

(22) Filed: Jan. 24, 2000

(51) Int. Cl.$^7$ .............................. G06F 19/00; C07K 1/00
(52) U.S. Cl. .......................................... 702/19; 530/300
(58) Field of Search ............................ 702/19; 530/300

(56) References Cited

PUBLICATIONS

Bangalore et al, Antiserum raised against a synthetic phosphotyrosine–containing peptide selectively recognizes p185neu/erb–2 and the epidermal growth factor receptor, Dec. 1992, Cell Biology, vol. 89, pp. 11637–11641.*

Mandell, A.J. (1984) Non–equilibrium behavior of some brain enzyme and receptor systems. Ann. Rev. Pharm. Toxicol. 24:237–274.

Mandell, A.J., Russo, P.V. and Blomgren, B.W. (1987) Complex hydrophobic sequence transformation predicts mutual recognition by polypeptides and proteins. Ann. N.Y. Acad. Sci. 504:88–118.

Mandell, A.J., Selz, K.A. and Shlesinger, M.F. (1997) Mode matches and their locations in the hydrophobic free energy sequences of peptide ligands and their receptor eigenfunctions Proc. Natl. Acad. Sci. 94:13576–13581.

Mandell, A.J., Selz, K.A. and Shlesinger, M.F. (1997) Wavelet transformation of protein hydrophobicity sequences suggests their membrships in structural families. Physica A224:254–262.

Mandell, A.J., Selz, K.A. and Shlesinger, M.F. (1997) Hydrophobic free energy eigenfunctions help define continuous wavelet transformations of amino acid sequences of protein families. Proc. Intl. (Fermi) Sch. Phys. CXXXIV, 175–192.

Di Marzo, E.A and Mandell, A.J. (1997) Phase transition behavior of a linear macromolecules threading a membrane. J. Chem. Physics 197:5510–5514.

Mandell, A.J., Owens, M.J., Selz, K.A., Morgan, W.N., Shlesinger, M.F. and Nemeroff, C.G. (1998) Mode matches in hydrophobic free energy eigenfunctions predict protein–protein interactions. Biopolymers 46:89–101.

Selz, K.A., Mandell, A.J., and Shlesinger, M.F. (1998) Hydrophobic free energy eigenfunctions of pore, channel and transporter proteins contain β–burst patterns. Biophysical J. 7:2332–2342.

Mandell, A.J., Selz, K.A. and Shlesinger, M.F. (198) Transformational homologies in amino acid sequences suggest membership in protein families. J. Stat. Phys. 93:673–697.

Mandell, A.J., Selz, K.A. and Shlesinger, M.F. (1999) Linear and entropic transformations of the hydrophobic free energy sequence help characterize a novel brain polyproptein: CART. In (M.T. Batchelor and L. Wille, eds.), *Statistical Physics on the Eve of the Twenty–First Century*, World Scientific, NJ, pp. 131–152.

Manavalan, P. and Ponnuswamy, P.K. (1978) Hydrophobic character of amino acid residues in globular proteins. Nature 275:673–674.

White, Stephen H. (1994) Global Statistics of Protein Sequences: Implications for the Origin, Evolution, and Prediction of Structure. Annu. Rev. Biophys. Biomol. Struct. 23:407–439.

Doyle, P.M. (1995) Combinatorial Chemistry in the Discovery and Development of Drugs. J. Chem. Tech. Biotechnol. 64:317–324.

Gordon, E.M., Barrett, R.W., Dower, W.J., Fodor, S.P.A. and Gallop, M.A. (1994) Applications of Combinatorial Technologies to Drug Discovery. 2. Combinatorial Organic Synthesis, Library Screening Strategies, and Future Directions. J. Med. Chem. 37(10):1385–1401.

Houghten, R.A. (1993) The Broad Utility Of Soluble Peptide Libraries For Drug Discovery. Gene 137:7–11.

\* cited by examiner

*Primary Examiner*—John S. Brusca
(74) *Attorney, Agent, or Firm*—Howrey Simon Arnold & White

(57) ABSTRACT

Methods of synthesizing a peptide or peptide-like molecule to a polypeptide or protein target based on mode-matching each member of a set of peptide constituents of the peptide or peptide-like molecule to peptide constituents of the target polypeptide or protein target.

45 Claims, 6 Drawing Sheets

A

B

SEQUENCE LISTING

<160> NUMBER OF SEQ ID NOS: 96

<210> SEQ ID NO 1
<211> LENGTH: 15
<212> TYPE: PRT
<213> ORGANISM: Artificial Sequence
<220> FEATURE:

<221> NAME/KEY: misc_feature
<223> OTHER INFORMATION: synthetic

<400> SEQUENCE: 1

Ser His Gln Arg Trp Glu Tyr Lys Gly Val Asn Cys Ile Val Tyr
1               5                   10                  15

<210> SEQ ID NO 2
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 2

Thr His Gln Ala Phe His Tyr Cys Asn Lys Gln Cys Leu Val Ile
1               5                   10                  15

<210> SEQ ID NO 3
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 3

Glu Arg Asn Arg Lys Pro Leu Arg Pro Lys Asn Lys Tyr Leu Ile
1               5                   10                  15

<210> SEQ ID NO 4
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 4

Glu Arg Asn Arg Lys Pro Tyr Arg Pro Lys Asn Lys Tyr Leu Leu
1               5                   10                  15

<210> SEQ ID NO 5
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 5

Ser His Thr Ala Tyr His Trp Met Ser Cys Gly Lys Ile Val Ile
1               5                   10                  15

<210> SEQ ID NO 6
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 6

Ser Arg Gln Ala Phe His Tyr Lys Asn Val Gln Val Leu Val Leu
1               5                   10                  15

```
<210> SEQ ID NO 7
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 7

Ser His Gln Ala Trp Arg Tyr Lys Asn Val Asn Cys Tyr Val Ile
1               5                  10                  15

<210> SEQ ID NO 8
<211> LENGTH: 16
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 8

Gly Glu Thr Ala Phe Arg Tyr Val Asn Cys Asn Val Tyr Val Tyr Ile
1               5                  10                  15

<210> SEQ ID NO 9
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 9

Gly His Ser Ala Trp Arg Trp Lys Ser Lys Asn Val Tyr Met Ile
1               5                  10                  15

<210> SEQ ID NO 10
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 10

Asn Ala Ser Ala Leu His Leu Val Gly Val Gln Cys Trp Val Tyr
1               5                  10                  15

<210> SEQ ID NO 11
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 11

Ser Trp Gln Ala Ile Arg Ile Cys Gln Lys Gly Val Leu Met Tyr
1               5                  10                  15

<210> SEQ ID NO 12
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 12
```

Ser His Ser Arg Trp Arg Ile Val Ser Val Asn Val Leu Cys Tyr
1               5                   10                  15

<210> SEQ ID NO 13
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 13

Phe Ser Phe Gln Cys Lys Ser Ile Asn Tyr Glu Ala Leu Gly Tyr
1               5                   10                  15

<210> SEQ ID NO 14
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 14

Phe Ser Phe Gly Val Lys Ser Trp Gln Tyr His Ala Leu Gly Tyr
1               5                   10                  15

<210> SEQ ID NO 15
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 15

Ile Thr Phe Thr Val Lys Gly Leu Thr Leu Ala Ala Phe Thr Tyr
1               5                   10                  15

<210> SEQ ID NO 16
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 16

Ile Ser Phe Asn Lys Cys Thr Trp Ser Phe Glu Arg Tyr Ser Leu
1               5                   10                  15

<210> SEQ ID NO 17
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 17

Phe Asn Leu Ser Val Lys Gln Trp Asn Tyr Arg Ala Tyr Asn Leu
1               5                   10                  15

<210> SEQ ID NO 18
<211> LENGTH: 15
<212> TYPE: PRT
<213> ORGANISM: Artificial Sequence

```
<220> FEATURE:
<221> NAME/KEY: misc_feature
<223> OTHER INFORMATION: synthetic

<400> SEQUENCE: 18

Leu Asn Tyr Gln Lys Lys Gln Tyr Thr Tyr Ala Ala Trp Gln Phe
1               5                  10                  15

<210> SEQ ID NO 19
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 19

Leu Thr Tyr Gly Val Met Asn Tyr Gly Phe Ala Ala Phe Gly Phe
1               5                  10                  15

<210> SEQ ID NO 20
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 20

Leu Gly Phe Ser Val Cys Pro Ile Thr Leu Ala Glu Leu Thr Tyr
1               5                  10                  15

<210> SEQ ID NO 21
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 21

Leu Gly Leu Gly Val Cys Pro Ile Asn Leu Ala Ala Leu Thr Trp
1               5                  10                  15

<210> SEQ ID NO 22
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 22

Leu Thr Trp Asn Val Lys Thr Tyr Ser Leu His Glu Leu Pro Leu
1               5                  10                  15

<210> SEQ ID NO 23
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 23

Asp Leu Cys Arg Ser Ala Arg Ser Asp Ile Glu Val Thr Glu Tyr
1               5                  10                  15
```

```
<210> SEQ ID NO 24
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 24

Arg Phe Val Ala Ser Ala Ala Thr Glu Ile Glu Val Asn Arg Leu
1               5                   10                  15

<210> SEQ ID NO 25
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 25

His Tyr Cys Ala Ser Ala Asp Pro Arg Ile His Lys Asn Ala Leu
1               5                   10                  15

<210> SEQ ID NO 26
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 26

Asp Phe Val Asp Gly Ala Ala Gly Arg Leu His Lys Gly Glu Tyr
1               5                   10                  15

<210> SEQ ID NO 27
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 27

Asp Ile Lys Ala Thr Glu Ala Thr Asp Ile Glu Lys Gly His Leu
1               5                   10                  15

<210> SEQ ID NO 28
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 28

Arg Phe Val Asp Asn Asp Ala Thr Asp Ile Glu Lys Gly Arg Ile
1               5                   10                  15

<210> SEQ ID NO 29
<211> LENGTH: 15
<212> TYPE: PRT
<213> ORGANISM: Artificial Sequence
<220> FEATURE:
<221> NAME/KEY: misc_feature
<223> OTHER INFORMATION: synthetic
```

```
<400> SEQUENCE: 29

Arg Phe Val Arg Gly Asp Arg Asn His Phe Asp Cys Gly Glu Leu
1               5                   10                  15

<210> SEQ ID NO 30
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 30

His Phe Val Arg Asn Glu Arg Thr His Phe Asp Val Ser Ala Leu
1               5                   10                  15

<210> SEQ ID NO 31
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 31

Ala Tyr Lys His Asn Glu Ala Thr Asp Ile Glu Lys Gly Asp Phe
1               5                   10                  15

<210> SEQ ID NO 32
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 32

His Ile Lys Arg Lys Glu Ala Thr His Ile Glu Lys Ser Ala Leu
1               5                   10                  15

<210> SEQ ID NO 33
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 33

His Ile Val Glu Gly Arg Ala Pro Glu Ile Ala Cys Gly Glu Tyr
1               5                   10                  15

<210> SEQ ID NO 34
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 34

Lys Pro Asn Leu Pro Asn Glu Leu Asn Lys
1               5                   10

<210> SEQ ID NO 35
<211> LENGTH: 10
<212> TYPE: PRT
```

```
<213> ORGANISM: Artificial Sequence
<220> FEATURE:
<221> NAME/KEY: misc_feature
<223> OTHER INFORMATION: synthetic

<400> SEQUENCE: 35

Val Thr Asn Leu Gly Asn His Ile Gly Val
1               5                   10

<210> SEQ ID NO 36
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 36

Cys Asn Asn Phe Ser Pro Asp Ile Thr Val
1               5                   10

<210> SEQ ID NO 37
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 37

Met Gln Gln Ile Thr Thr His Phe Gln Cys
1               5                   10

<210> SEQ ID NO 38
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 38

Val Asn Thr Phe Gly Thr Glu Leu Ser Cys
1               5                   10

<210> SEQ ID NO 39
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 39

Cys Asn Asn Ile Gly Asn Arg Leu Ser Cys
1               5                   10

<210> SEQ ID NO 40
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 40

Lys Gly Asn Phe Thr Pro Glu Trp Pro Cys
1               5                   10
```

<210> SEQ ID NO 41
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 41

Met Gly Pro Leu Pro Gln Ala Phe Gln Cys
1               5                   10

<210> SEQ ID NO 42
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 42

Lys Ser Asn Ile Gly Pro Ala Leu Thr Met
1               5                   10

<210> SEQ ID NO 43
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 43

Val Ser Gln Tyr Gly Gln Glu Leu Gln Val
1               5                   10

<210> SEQ ID NO 44
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 44

Val Ser Pro Tyr Gln Ser His Phe Asn Val
1               5                   10

<210> SEQ ID NO 45
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 45

Met Gly Gly Trp Gly Pro Ala Leu Asn Cys
1               5                   10

<210> SEQ ID NO 46
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 46

Cys Thr Gly Tyr Thr Asn Ala Ile Gln Met
1               5                   10

<210> SEQ ID NO 47
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 47

Met Asn Thr Leu Gln Gln Ala Tyr Pro Lys
1               5                   10

<210> SEQ ID NO 48
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 48

Val Gln Pro Tyr Asn Gly Glu Leu Asn Met
1               5                   10

<210> SEQ ID NO 49
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 49

Val Thr Asn Trp Asn Gly Arg Ile Asn Lys
1               5                   10

<210> SEQ ID NO 50
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 50

Met Gln Asn Phe Pro Thr Ala Ile Asn Val
1               5                   10

<210> SEQ ID NO 51
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 51

Val Pro Ser Ile Gln Gly His Tyr Gly Met
1               5                   10

<210> SEQ ID NO 52
<211> LENGTH: 10

```
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 52

Val Gly Asn Leu Thr Gln His Tyr Thr Lys
1               5                   10

<210> SEQ ID NO 53
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 53

Val Pro Pro Phe Thr Asn His Trp Gln Lys
1               5                   10

<210> SEQ ID NO 54
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 54

Val Gly Thr Leu Asn Pro Ala Phe Ser Val
1               5                   10

<210> SEQ ID NO 55
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 55

Cys Gly Asn Tyr Gly Thr Arg Phe Ser Lys
1               5                   10

<210> SEQ ID NO 56
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 56

Cys Ser Ser Leu Gln Gln Ala Leu Thr Val
1               5                   10

<210> SEQ ID NO 57
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 57

Met Pro Ser Ile Pro Thr His Leu Asn Lys
```

```
<210> SEQ ID NO 58
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 58

Lys Asn Asn Tyr Gly Gln Ala Phe Thr Val
1               5                   10

<210> SEQ ID NO 59
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 59

Lys Asn Gln Leu Asn Thr Glu Ile Asn Cys
1               5                   10

<210> SEQ ID NO 60
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 60

Lys Asn Pro Leu Asn Asn His Leu Asn Met
1               5                   10

<210> SEQ ID NO 61
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 61

Val Asn Gly Ile Gly Gln Ala Ile Asn Val
1               5                   10

<210> SEQ ID NO 62
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 62

Cys Pro Gly Ile Thr Gly Asp Phe Gln Lys
1               5                   10

<210> SEQ ID NO 63
<211> LENGTH: 10
<212> TYPE: PRT
<213> ORGANISM: Artificial Sequence
<220> FEATURE:
<221> NAME/KEY: misc_feature
```

<223> OTHER INFORMATION: synthetic

<400> SEQUENCE: 63

Met Thr Gln Phe Gln Ser His Ile Thr Val
1               5                   10

<210> SEQ ID NO 64
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 64

Val Gln Thr Tyr Pro Pro His Phe Pro Val
1               5                   10

<210> SEQ ID NO 65
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 65

Lys Gly Asn Leu Asn Thr Asp Leu Asn Met
1               5                   10

<210> SEQ ID NO 66
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 66

Val Thr Pro Leu Ser Ser Ala Ile Asn Lys
1               5                   10

<210> SEQ ID NO 67
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 67

Val Asn Asn Leu Ser Ser Glu Tyr Asn Val
1               5                   10

<210> SEQ ID NO 68
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 68

Met Pro Pro Trp Pro Ser Asp Tyr Pro Cys
1               5                   10

<210> SEQ ID NO 69

```
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 69

Lys Gln Ser Phe Gln Ser Glu Leu Asn Lys
1               5                   10

<210> SEQ ID NO 70
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 70

Val Pro Ser Leu Thr Thr Arg Leu Gln Val
1               5                   10

<210> SEQ ID NO 71
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 71

Val Gln Pro Leu Gln Gly His Leu Pro Val
1               5                   10

<210> SEQ ID NO 72
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 72

Val Ser Gln Phe Asn Gln Ala Trp Gly Val
1               5                   10

<210> SEQ ID NO 73
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 73

Val Pro Ser Leu Asn Ser Ala Leu Gly Val
1               5                   10

<210> SEQ ID NO 74
<211> LENGTH: 10
<212> TYPE: PRT
<213> ORGANISM: Artificial Sequence
<220> FEATURE:
<221> NAME/KEY: misc_feature

<400> SEQUENCE: 74
```

Met Asn Ser Ile Gln Thr Asp Phe Thr Met
1               5                  10

<210> SEQ ID NO 75
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 75

Val Gln Ser Leu Thr Asn Asp Ile Ser Lys
1               5                  10

<210> SEQ ID NO 76
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 76

Lys Gly Asn Ile Asn Pro Ala Tyr Asn Val
1               5                  10

<210> SEQ ID NO 77
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 77

Lys Thr Gly Leu Asn Asn Glu Ile Asn Val
1               5                  10

<210> SEQ ID NO 78
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 78

Val Gln Ser Phe Thr Asn Glu Ile Gln Cys
1               5                  10

<210> SEQ ID NO 79
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 79

Lys Thr Thr Ile Asn Gly His Ile Ser Lys
1               5                  10

<210> SEQ ID NO 80
<211> LENGTH: 10
<212> TYPE: PRT
<213> ORGANISM: Artificial Sequence
<220> FEATURE:

```
<221> NAME/KEY: misc_feature
<223> OTHER INFORMATION: synthetic

<400> SEQUENCE: 80

Val Gly Gly Tyr Gly Thr Asp Tyr Asn Met
1               5                   10

<210> SEQ ID NO 81
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 81

Met Gln Gly Tyr Thr Asn Asp Ile Pro Val
1               5                   10

<210> SEQ ID NO 82
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 82

Val Asn Gln Trp Gln Asn His Tyr Thr Met
1               5                   10

<210> SEQ ID NO 83
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 83

Lys Pro Thr Phe Ser Asn Ala Tyr Asn Val
1               5                   10

<210> SEQ ID NO 84
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 84

Val Thr Asn Phe Ser Asn Ala Leu Ser Met
1               5                   10

<210> SEQ ID NO 85
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 85

Val Thr Pro Ile Asn Ser Glu Phe Pro Cys
1               5                   10
```

```
<210> SEQ ID NO 86
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 86

Lys Asn Gln Leu Asn Thr His Ile Gly Lys
1               5                   10

<210> SEQ ID NO 87
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 87

Val Gln Ser Ile Asn Asn Ala Ile Gly Lys
1               5                   10

<210> SEQ ID NO 88
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 88

Met Gly Thr Phe Gln Pro Asp Trp Gln Val
1               5                   10

<210> SEQ ID NO 89
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 89

Val Gln Thr Ile Ser Ser Arg Trp Gly Lys
1               5                   10

<210> SEQ ID NO 90
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 90

Met Gly Asn Ile Thr Gln Asp Leu Gln Cys
1               5                   10

<210> SEQ ID NO 91
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 91
```

```
Lys Gly Ser Tyr Thr Thr Glu Leu Gly Val
1               5                   10
```

<210> SEQ ID NO 92
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 92

```
Lys Asn Ser Tyr Ser Pro Glu Leu Thr Val
1               5                   10
```

<210> SEQ ID NO 93
<211> LENGTH: 10
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 93

```
Cys Asn Ser Tyr Thr Pro Glu Phe Pro Cys
1               5                   10
```

<210> SEQ ID NO 94
<211> LENGTH: 32
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 94

```
Ala Ile Arg Cys Lys Ser Met Leu Arg Tyr Gly His Ala Met Gln Leu
1               5                   10                  15
Arg Glu Trp Val Cys Cys Met His Ala Met Gln Val Tyr Arg Leu Met
            20                  25                  30
```

<210> SEQ ID NO 95
<211> LENGTH: 16
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 95

```
Ala Ile Arg Cys Lys Ser Met Leu Arg Tyr Gly His Ala Met Gln Leu
1               5                   10                  15
```

<210> SEQ ID NO 96
<211> LENGTH: 15
<212> TYPE: PRT
<213> ORGANISM: Artificial Sequence
<220> FEATURE:
<221> NAME/KEY: misc_feature
<223> OTHER INFORMATION: synthetic

<400> SEQUENCE: 96

```
Ala Ile Arg Cys Lys Ser Met Leu Arg Tyr Gly His Ala Met Gln
1               5                   10                  15
```

ALGORITHMIC DESIGN OF PEPTIDES FOR BINDING AND/OR MODULATION OF THE FUNCTIONS OF RECEPTORS AND/OR OTHER PROTEINS

FIELD OF THE INVENTION

The invention relates generally to peptide molecules and to methods of designing peptides or peptide-like molecules. More particularly, the invention relates to novel, short peptides or peptide-like molecules which have a high probability of binding to and/or otherwise modulating the function of polypeptides or proteins, and to methods for designing such peptides or peptide-like molecules.

BACKGROUND OF THE INVENTION

All protein sequences, whether peptides, polypeptides, or proteins, are composed of a linear sequence of amino acids joined by peptide bonds. There are twenty naturally occurring amino acids, each bearing a chemically unique side chain. Determinants of polypeptide interactions, such as those between peptide segments in protein folding or between protein monomers, are encoded in the one-dimensional sequence of these twenty amino acid side chains. For purposes of this application, "peptides" are generally considered to be amino acid polymers of not more than 25 amino acids in length; "polypeptides" are generally considered to be polymers of between 25 and 50 amino acids; and "proteins" are generally considered to be polymers containing more than 50 amino acids. One of ordinary skill in the art would appreciate that some overlap among these ranges is expected, and minor deviations from these ranges does not in any way diminish the scope of the invention. The "naturally occurring amino acids" are those that are encoded for in the genetic code, and which are generally considered to be those found in all living species to date.

Net differences in the cumulative energetic contributions of several types of weak bonding mechanisms, totaling as little as $\Delta G=5-10$ kcal/mol, determine selection and stabilization among conformations observed in protein folding, protein-protein interactions and the initial phases of substrate-enzyme and ligand-membrane receptor association. In particular, the minimization of $\Delta G$ through the formation of four general types of weak bonding mechanisms between amino acid side chains, in the range of $\Delta G \cong 2-7$ kcal/mol, determines the arrangement of protein sequences in three-dimensional space, as well as the relative orientations of protein chain aggregates, in aqueous environments and at physiological temperatures. The thermal instability of the conformations supported by these low $\Delta G$, reversible, weak-bonding mechanisms permits uncatalyzed, fast searches of configuration space for functionally optimal cooperative arrangements within and between polypeptide and protein monomers. The variety of weak bond capacities afforded by amino acid side chains determines the range of the amino acid sequences' physicochemical property transformations listed in this invention.

The weak bonds ordering polypeptides and proteins in three-dimensional space include hydrogen bonds, such as the main chain amino acid carbonyl and imino groups, which configure the right-turning α-helices and the parallel and antiparallel β-sheets. They also include the hydrogen and ionic bonds between amino acid side chains, such as the hydroxyl groups of serine and threonine, the acidic carboxyl groups of aspartate and glutamate, and the basic groups of lysine and arginine. In addition to being distinct with respect to the chemical group, these weak hydrogen and ionic bonding influences are also directionally specific, with bonding angles greater than 30° reducing their influence to negligible levels.

A third but nondirectional type of weak bonding interaction, induced by fluctuating charges within a distance of 1–3 Å, is called van der Waal forces. These interactions vary with the size and the extent of mutual geometric fit, but are in the range of 1–2 kcal/mol. These forces are barely greater than those due to the heat of molecular motion at room temperature ($\Delta G \cong 0.6-1.0$ kcal/mol). However, in the specific cases of some antibody/antigen interactions and MHC protein/peptide interactions, which involve water-releasing tight fits between corresponding moieties in suitably shaped binding pockets, the $\Delta G$s associated with van der Waals interactions have been estimated to be as high as 30 kcal/mol.

A fourth weak bonding mechanism, and the most energetically dominant force on three-dimensional polypeptide structure and protein-protein interactions, is termed the hydrophobic effect. The hydrophobic effect arises from the much stronger attraction that water molecules have for each other than for hydrocarbon groups or molecules. Each tetrahedrally-coordinated water molecule participates in strong, hydrogen-bonded, dipole/dipole interactions with other water molecules that are manifested in the properties of water such as its high surface tension, high latent heat and high boiling point. These physicochemical features of water molecules afford a large variety of possible atomic arrangements of water (as seen in the large number of different ice types) that in turn permit maximizing the entropy and minimizing the free energy of the aqueous solution. Spatially distributed (nondirectional) deformations in these hydrogen-bonded arrangements of water result from the intrusion of nonpolar, hydrophobic solutes. The introduction of such molecules into an aqueous solution results in the formation of volume-expanding hydration shells composed of hydrogen-bonded cages of multiple molecular layers of water ("clathrate structures") around these molecules, in a process called "hydrophobic hydration". In aqueous solutions, such deformations in water structure are energetically unfavored. For example, the side chains of alanine, valine, leucine and isoleucine are without effective dipole moments, and therefore cannot participate in charge-mediated or hydrogen-bonding interactions with water. As a result, these side chains intrude into the aqueous solvent and disrupt the ordered structure of the aqueous solvent, resulting in an increase in the overall $\Delta G$. Amino acids with polar but uncharged side chains, such as serine and threonine, may hydrogen bond with a molecule of water, but otherwise undergo the same kind of hydrophobic hydration as the non-polar side chains. In the case of amino acids with side chains containing charged groups, such as glutamate or lysine, the electrostatic fields associated with these side groups are screened by water molecules, such that in an aqueous solution hydrophobic hydration is still a prominent characteristic of these amino acids as well. The nonlocal, cooperative interactions of the hydrogen bonds of the aqueous solvent surrounding these amino acids drive the in-line, surface-minimizing attraction between the coherent hydrophobic-phase patches of amino acid side chains, thereby maximizing the entropy, and minimizing the free energy, of the overall aqueous solution.

The importance of the sequential arrangements of amino acid side chain hydrophobicities in the determination of peptide and protein secondary structures has been established knowledge in protein biology for many decades. The ready availability of water for compensatory weak bonding implies that relatively small changes in ΔG occur when internal peptide backbone-related, carbonyl-imino hydrogen bonding or side chain polar groups are not satisfied. This contrasts with the much greater alteration in ΔG associated with loss of internal hydrophobic bonding, which cannot be compensated by the hydrophobically disrupted, aqueous environment. Minimization of hydrophobic free energy, $\Delta G_{hp}$, by water interface-reducing aggregation of nonpolar, hydrophobic amino acid side chain groups adds to the ΔG of binding that can, collectively, be orders of magnitude larger than that predicted by van der Waals theory. Mutually attractive forces mediated by hydrophobic surface minimization have been measured by atomic force spectroscopy to extend to as great a distance as 60 Å, the length scale of synaptic gaps. These attractive forces decay less than exponentially with distance. The contribution to the energy of stabilization of the three-dimensional, tertiary structure of protein by $\Delta G_{hp}$ minimization due to aggregation of hydrophobic amino side chains has been estimated to be in the range of 70%.

Complete substitution of hydrophobically equivalent amino acids in peptides maintains and sometimes increments their peptide-receptor mediated physiological potency. Additionally, proteins which are dominated by helical secondary structures of specific turn lengths can be designed using sequences of amino acids of high and low hydrophobicities, independent of the specific amino acids chosen within each hydrophobicity class. In contrast, regions of amino acids characterized by interactions dominated by hydrogen bonds, ionic bonds, and van der Waals interactions are often exquisitely sensitive to any substitution, even those deemed to be conservative replacements. This difference between the effects on ΔG of hydrophobic interactions versus those of hydrogen bonding, ionic binding or van der Waals interactions, along with more stringent geometric requirements of the latter compared with hydrophobic weak bonds, make sequential patterns of $\Delta G_{hp}$ in polypeptide sequences of primary importance in determining peptide-peptide or peptide-protein interactions.

Previously, the role of the hydrophobic interactions of amino acids in peptide ligands with amino acids in their associated membrane proteins have been considered in structure-function analyses in two ways. First, the local roles of amino acids have been evaluated. In these studies, ligand-receptor binding is changed by point mutations in specifically positioned amino acids, producing alterations in the hydrophobic characteristics of "binding pockets" involving neighboring but nonsequential juxtapositions of residues brought together in the protein's cooperative tertiary structure. Second, the global effects of amino acids have been examined. These effects are often studied using chimeric exchanges, with respect to the number, lengths, and locations of transmembrane segments of receptors, transporters, and/or channels, and exploit the sequential juxtapositions of amino acid hydrophobicities, using n-point window moving averages to generate what are commonly known as "hydropathy plots". The largest, longest positive variations in these smoothed hydrophobic amplitude graphs across sequence-indexed location of membrane proteins are interpreted as the lipophilic, hydrophobic transmembrane segments of the membrane protein. The best-studied example of this approach is the finding of seven sequential hydrophobic maxima of approximately 25 residues each in the hydropathy plots of bacteriorhodopsin, assumed to be the evolutionary prototype of the G-protein gene superfamily of transmembrane receptors. This common transmembrane receptor protein motif comprises copolymers of seven transmembrane domains that snake back and forth across the lipid bilayers of membranes, anchored by lipophilic transmembrane ("TM") segments. In this motif, three separate extracellular loops ("ELs") are defined by the TMs: the first extracellular loop, EL-I, between $TM_2$ and $TM_3$; the second extracellular loop, EL-II, between $TM_4$ and $TM_5$; and the third extracellular loop, EL-III, between $TM_6$ and $TM_7$.

Secondary structures with matching wavenumbers, such as the β-strands of interleukin-1β, have been shown to bind together and initiate protein folding in a process called the "hydrophobic zipper". We define "wavenumbers" as the inverse spatial variational frequencies of a physicochemically transformed series. They are reported here in sequential distance units of amino acids. Two long, helical secondary structures with congruent hydrophobic wavenumbers bind to create the central "hydrophobic knot" that stabilizes the structure of phospholipase $A_2$. Recent studies of the binding of extracellular domains of growth hormone receptor by polyclonal antibodies to ovine growth hormone have shown that functional binding occurs between the epitope sequences and the extracellular segments of the growth hormone transmembrane receptor. This binding, analogous to that between peptide ligands and their receptors, is more related to common helical, loop and/or disordered secondary structures than to specific amino acid sequences or their local three-dimensional geometry.

Estimates of the relative contributions by the $\Delta G_{hp}$ of each of the twenty amino acids to these weak bond-mediated reactions can be approximated as the free energy of transfer from aqueous to organic phases of each of the amino acids in a binary solution. Values for the free energy of transfer are measured as the relative equilibrium partitions $K_{eq}=e^{-\Delta G_{hp}/RT}$, expressed in kcal/mol, in these aqueous-organic binary solvents. The transformation of individual amino acids into their $\Delta G_{hp}$ values enables the conversion of polypeptide and protein sequences into real number series available for analyses with respect to matches in sequential patterns. These have been predictive of differentially selective hydrophobic attraction and aggregation between peptide ligands and relevant extracellular receptor loops following their search via "snake upon snake" sliding diffusion, or "reptation".

A topologically one-dimensional polypeptide sequence manifests secondary structures, which are organized into supersecondary structures and further into tertiary structures. For example, spiral rotations of ≈3.6 amino acids are the elementary component of a helical barrel comprised of 12–16 amino acids. These helical barrels may be joined by short loops into four-barrel bundles comprised of 60–70 amino acids, which may in turn be part of a protein domain containing several hundred amino acids and forming sequentially segregated or alternating barrels, bundles, β-sheets and coils and loops of varying lengths. Therefore, hydrophobic sequences of a range of lengths may underlie the conformational components of different sizes and complexity that comprise the compact intermediate states of proteins.

Transformations of polypeptide sequences into $\Delta G_{hp}$ values have been found useful in predicting polypeptide chain turns composing secondary structures, such as α-helices and β-strands. These predictions have been confirmed by x-ray crystallographic studies. Generic α-helices are ≈5.4 angstroms long with 3.6 amino acids per rotation resulting in ≈1.5 angstrom linear distance per residue. Generic β-strands have 2.1 amino acids per turn with ≈3.3 angstroms linear distance per residue.

Sliding window $\Delta G_{hp}$ averages were shown to be able to locate the lipophilic, hydrophobic transmembrane segments of membrane proteins, and these results were confirmed using low- and high-resolution crystallographic studies of bacteriorhodopsin as a model seven-transmembrane receptor protein. It is generally accepted that representation of polypeptide sequences as a series of amino acid aqueous volumes, partial specific volumes or $\Delta G_{hp}$, followed by n-block averaging, statistical predilection, hydrophobic moments, Fourier transformation, helical wheel plots or wavelet transformations can predict the size and locations of secondary and transmembrane structures in soluble and membrane proteins 60–80% of the time. These approaches have also been found useful in predicting supersecondary structures, such as the four-helix barrels and the supercoiling of α-helical structures about each other in fibrous proteins, such as the keratins and myosin tails. However, one drawback of these methods is that coexisting sequential variations in hydrophobic free energy wavelengths (mode or modes) other than that of transmembrane segments are lost in the generation of hydropathy plots by smoothing. Moreover, conventional Fourier transformation of the protein's hydrophobicities results in poor mode definition, because of end effects and intrinsic multimodality. In addition, these conventional techniques have thus far provided no solution of what is called the "inverse problem"—that is, even if the conventional methods were able to define one or more given signatory and relevant modes, how does one construct a de novo peptide using these modes? The present invention overcomes the deficiencies of the prior art, and describes successful solutions to the inverse problem.

When the amino acid sequences of neuropeptides and peptide hormones were transformed into their individual $\Delta G_{hp}$ values, functionally related peptides demonstrated similarities in hydrophobic free energy power spectral mode or modes. Functionally related peptide family members share the same statistically significant dominant power spectral wavelengths (wavenumbers expressed as inverse spatial frequencies), though differing in their ordered amino acid content by as much as 60%. The power spectral wavelengths are expressed in units of amino acid residues as $h(\omega)$. For example, glucagon, vasoactive intestinal peptide, secretin, oxytomodulin, helodermin and growth hormone releasing factor, which share several (but not all) physiological actions and which have differing relative potencies, share a $h(\omega)=4.0$. The range of peptide hydrophobic modes found by the power spectral transformation of amino acid sequences as hydrophobic free energies includes the well known $h(\omega)=3.6$ and $h(\omega)=2.0$ of the α-helix and the β-strand, respectively, but many others as well, ranging from the $h(\omega)=13.10$ amino acid residue of acid fibroblast growth factor to the $h(\omega)=2.18$ which dominates the hydrophobic free energy power spectrum of corticotropin releasing factor.

The HIV coat protein manifests a waxing and waning of $h(\omega)=7$ to 9 (observed by sliding a 50-residue windowed Fourier transform along its sequence), which appears to be conserved across many of its mutations. Fibroblast growth factor ("FGF") was predicted and confirmed to have a regulatory influence on the enzyme ribonuclease A, with which it was found to share dominant hydrophobic mode. This mode match led to experiments that demonstrated an increased half-life of messenger RNA in the presence of FGF in a neuroendocrine cell line.

The specific amino acid sequences of the calcitonins, the peptide hormone family that regulates the rate of enzymatic bone catabolism, vary by approximately 60% across species, but all are dominated by an h(ω)=3.6. The most potent calcitonin (from salmon) expresses this mode with a significantly lower hydrophobicity per residue (due the presence of a higher number of charged groups) than those of nine other species examined. The same h(ω) can be expressed across differing average hydrophobicities of the amino acid sequences of peptides and receptors.

Using a variety of techniques involving linear decomposition and transformation of the $\Delta G_{hp}$ sequences, we have obtained diagnostic graphical patterns of known and novel proteins with weak or unknown homology, polyproteins which have multiple functional segments following post-translational processing, and discriminable subtypes in membrane pore, channel and transporter proteins. These methods, which decompose $\Delta G_{hp}$ series into their hierarchical levels of organization to yield secondary and supersecondary patterns at multiple wavelengths and/or length scales, include a variety of wavelet transformations, eigenvalue decomposition of autocovariance matrices and all poles, maximum entropy power spectra. Using $\Delta G_{hp}$ sequences as input, these methods elucidated primary and secondary wavenumbers and the sequential order of these multiple hydrophobic modes which, when taken together, can contribute to the preliminary classification of unknown proteins into families or provide clues to their function.

Using these techniques, we have located peptide-receptor mode matches in the ELs of seven-transmembrane proteins, in the vicinity of neurotransmitter and pharmacological binding domains suggested by studies of point mutations and chimeric exchanges. The ligands designed for mode-matched hydrophobic aggregation at these sites are postulated to have modulatory (e.g. allosteric and/or direct) influences on the physiological activities induced by the corresponding membrane protein's native ligands. In addition, mode matches were found between the α-estrogen receptor and a known peptide antagonist; between a nuclear membrane docking site on a nuclear factor of activated T-cells and the known ligand calcineurin; and between the protein chaperonin GroEL and β-lactamase, which is known to be bound by GroEL.

Eigenfunctions of autocovariance matrices of lagged $\Delta G_{hp}$ sequence data matrices, maximum entropy power spectra and wavelet transformations were used as linear decompositions to remove the longer $\Delta G_{hp}$ sequence wavelengths of various receptor TMs, leaving the shorter wavelength hydrophobic modes for analyses. Matches as statistical patterns in $\Delta G_{hp}$ modes were found between peptide ligands and their membrane receptors, including kappa, mu, delta and orphan opiate receptors, corticotropin releasing factor receptor, cholecystokinin receptor, neuropeptide Y receptor, somatostatin receptor, bombesin receptor, and neurotensin receptor. Functionally significant mode matches also occur between peptides and non-peptide receptors and other proteins. For example, $\Delta G_{hp}$ mode matches, such as those found between the dopamine co-localized neuropeptide neurotensin and the $D_2$ dopamine membrane receptor, $D_2DA$, and those found between the gastrointestinal and brain peptide cholecystokinin and the dopamine membrane transporter, DAT, predicted the differential binding of the pharmacologically active ligands to their respective responsive dopamine membrane receptors and, correspondingly, their lack of binding to the opposing, pharmacologically unresponsive dopamine membrane receptors.

We have proposed that functional interactions of peptides and biogenic amines may occur via selective hydrophobic aggregation of these peptides with mode-matched ELs on a target membrane protein. These interactions may result in heterosteric modification of the global kinetic conformations of the target membrane protein, and thereby produce responses to native or pharmacological ligands, distant from intramembranous ion- or charge-mediated active sites. We have modeled the joint actions on a single membrane protein as the shifting of the critical hydrophilic-hydrophobic partition between extra- and intramembranous portions of the TMs of receptors by peptide-receptor loop hydrophobic weak bond binding. This would facilitate (or retard) the first-order phase transition of native ligand induced-receptor membrane internalization, where low dielectric constant, unscreened ionic and/or charge-mediated tight binding most likely occurs. This theory contrasts with another suggesting that receptor-mediated interactions between co-localized biogenic amines and neuropeptides, such as dopamine and cholecystokinin, result from convergent intramembranous signaling through two receptors, one for each ligand, via the cooperative interactions between their membrane receptor proteins which result in G-protein mediated second messenger cascades.

Peptides are known to mediate a variety of physiological responses in many organisms, including man. Among these bioactive peptides are the peptide hormones, such as glucagon and insulin, which regulate glucose levels in the blood; gastrin and secretin, which control digestive processes; and follicle-stimulating hormone (FSH) and leuteinizing hormone, which regulate reproductive processes. Other bioactive peptides act as growth factors, including somatotropin (growth hormone), erythropoietin, and NGF (nerve growth factor).

Because of the powerful and specific effects of these peptides, they have long held great interest as drug candidates. For example, insulin is widely used to combat diabetes, and erythropoietin stimulates red blood cell formation. However, peptides have numerous drawbacks as potential therapeutics. Peptides are very unstable and sensitive to changes in their environments, which can create alterations in their structures and reduce or eliminate their physiological effects. Furthermore, peptides are susceptible to proteolysis, which complicates the problem of delivery to the desired site in the body and limits the available routes of administration. The available routes of administration are further limited by the relatively large sizes of many peptides, which make transdermal or inhalation administration methods impractical. Because peptides typically interact with other peptides or proteins to produce their biological effects, and the in vivo interactions between even a simple peptide and another protein are extraordinarily difficult to understand, enormous effort is required to determine the interactions between such molecules, or even to predict if such interactions will occur. Finally, relatively few bioactive peptides are known, in comparison to the number of potential polypeptide targets that mediate biological effects. As a result, there is great interest in finding methods to predict sequences of peptides that will interact with a polypeptide/protein target, and produce a desired physiological response. The present inventors have made the revolutionary discovery that peptides, in interaction with solvent-accessible proteins, also influence the behavior of proteins (as above) that are not specific peptide receptors.

The difficulties associated with predicting the structure of peptides that would produce a given effect in the body have led to the adoption of various combinatorial approaches. These methods produce large numbers of peptides having randomly generated sequences. The peptides are then subjected to various high-throughput screening methods to detect those peptides that may warrant further study. However, without prior knowledge of a relevant sequence pattern, often called a peptide pharmacophore, and without proven methods of pattern-conserving design, finding physiologically active lead compounds in applications involving peptide-protein interactions using purely random combinatorial searches is generally a low probability event. Depending on the candidate peptide length, the statistical expectations with respect to hits in at least micromolar concentrations using high throughput screening of $\geq 300,000$–$400,000$ component peptide libraries generated by parallel synthesis and combinatorial strategies, can be less than 2–4 per 100,000 peptides. Detection of these candidate peptides requires costly and time-consuming high-throughput methods for both peptide synthesis and for screening of the peptides. As a result, there is a great need for a method that can produce peptides or peptide-like drugs having a high probability of binding, modulating the activity of, activating or inhibiting a target polypeptide and/or protein.

SUMMARY OF THE INVENTION

The present invention relates to entirely new methods of designing peptides or peptide analogue molecules capable of binding to and/or otherwise modulating the function of protein targets having known amino acid sequences. The methods employ three kinds of templates, derived from analyses of the target protein sequences, in addition to relevant distributions of amino acids, for weighted and constrained random assignments to the templates to produce the peptides. Protein targets suitable for use in the present invention include cell membrane receptors, nuclear membrane receptors, circulating peptide and non-peptide receptors, membrane and circulating transporters, enzymes, chaperonins and chaperonin-like proteins; antibodies, surface proteins of infectious agents, and more generally, any protein involved in peptide-protein and/or protein-protein interactions. The peptides are designed to bind to and/or otherwise modulate, activate and/or inhibit the function of the target protein. The kinetic influence of the algoritimically-designed peptides on target protein function may be direct, competitive, uncompetitive, noncompetitive and/or allosteric in character. The templates are derived from at least one of the following: 1) eigenvectors of the autocovariance matrices of the physicochemically transformed amino acid sequence of the target protein; 2) wavelet subsequence templates derived from a variety of wavelet transformations of the physicochemically transformed amino acid sequence of the target protein; and 3) redundant subsequence templates computed from the physicochemically transformed amino acid sequence of the target protein. In the methods of the present invention, the constituent amino acids employed in synthesis of the peptide are partitioned into a finite number of groups, based on similarities in values of a physicochemical property. Thereafter, the amino acids are randomly assigned to the peptide, based on matching the physicochemical mode of the template derived from the target protein amino acid sequence. Partitioned amino acid distributions for random assignments to the similarly partitioned templates may be weighted by, for example, consideration of amino acid distribution in a variety of extra- and/or intracellular physiologically relevant pools or alternatively, such distributions in regions in the target protein sequence relevant to the construction of the templates. The physicochemical transformations of each of the amino acids in the target protein sequence may be based on, for example, hydrophobic free energy, relative vapor pressure, relative free energy of amino acid transfer into bulk phases, aqueous molar volume, aqueous surface area, aqueous cavity surface area, partial specific volume, relative charge, relative mass (in daltons), volume, $pK_a$, relative diffusivity, relative frictional coefficient, relative chromatographic mobility, relative electrophoretic mobility, and/or memberships in categorical amino acid families such as polar, uncharged, polar charged, basic-positively charged, acidic-negatively charged and sulfur containing. Sequential pattern ("mode") matches between candidate algorithmic peptides and their target proteins are designed such that when examined by maximum entropy, all poles, power spectral transformations and/or wavelet transformations, they yield peaks with wavenumbers that differ by 10% or less of the larger wavenumber value. As noted above, wavenumbers are the inverse spatial variational frequencies of a physicochemical transformed data series, expressed in sequential distance units of amino acids. These peptides are then selected for physiological testing on the target protein system. The peptide design methods and an associated mechanistic rationale are illustrated for the methods of the present invention, using an eigenvector template derived from the hydrophobic free energy-transformed sequence of several different receptors and random assignment of amino acids to the eigenvector templates based on probability-weighted amino acid pool distributions. The peptides generated in this manner demonstrate physiological activity in receptor-transfected cell systems, as shown by direct action and/or pretreatment potentiation or inhibition of extracellular acidification rates. In addition, peptides generated by the methods of the present invention also bound to and otherwise interact with and alter the activities of the seven-transmembrane cholinergic M1 receptor ("muscarinic M1 receptor") and the nerve growth factor (NGF) receptor, which has one transmembrane segment. As another example of the range of applicability of these methods, hydrophobic free energy mode matches between the peptide fibroblastic growth factor and ribonuclease successfully predicted their functional interaction in neuroendocrine cell culture. These results illustrate the broad applicability of the methods of the present invention to the design of peptides for binding to or otherwise modulating a wide variety of different kinds of target polypeptides and proteins.

One of the three mode-matched peptide design methods of the invention involves the construction of such peptides using random assignment of peptide constituents, such as amino acids, as dictated by an eigenvector template containing polypeptide-matching physicochemical property binding/modulating modes. This method is herein exemplified by one of many possible physicochemical properties usable in the method, namely, hydrophobic free energy. The template eigenvector is obtained by linear decomposition of an autocovariance matrix formed by transformation of the polypeptide's amino acid sequence into a physicochemical sequence, in this case a hydrophobic free energy data series. The leading eigenvalue-associated eigenvectors are convolved with the original hydrophobic free energy data series to construct eigenfunctions. These eigenfunctions may then be further analyzed using wavelet transformations and all poles, maximum entropy power spectral transformations. The wavelet transformations may be discrete or continuous, and further may be one-dimensional wavelet packets or multiple convolved wavelet transformations. This approach yields clean representations of the polypeptide hydrophobic free energy modes as leading and secondary eigenfunctions. Most of the information found in the secondary eigenfunctions would be lost in the conventional smoothing of hydropathy plots, or contaminated by end effects and multimodality in conventional Fourier transformations. The eigenvectors associated with these eigenfunctions are used as templates for the formation of mode-matched peptides that can be tested for their ability to bind to or otherwise modulate the receptor. A mode match is attained when the maximum entropy power spectral or wavelet transformations of the polypeptide and the peptide or peptide-like molecule yield wavenumbers that differ by 10% or less of the larger wavenumber value. The amino acids intended for use in producing the candidate peptide are grouped into a number of groups, based on their assigned values of a physicochemical property (e.g. hydrophobic free energy). The eigenvector associated with the eigenfunction (or, alternately, the eigenvectors-based vector) is graphed, where the x-axis shows ordered position of the eigenvector and the Y-axis shows the numerical values of the physicochemical property. The y-axis is partitioned into an equal number of groups as intervals of the y-axis (e.g., four equal intervals), converting the eigenvector (or eigenvectors-based vector) into an eigenvector template. Amino acids corresponding to the value of the physicochemical property on the y-axis of the eigenvector template are randomly assigned to positions in the template, forming peptides or peptide-like molecules. The amino acid assignments may also be weighted or otherwise altered in accordance with a specific amino acid pool distribution or in accordance with known effects of substitutions of individual amino acids or amino acid segments, if desired.

The second method involves the construction of mode-matched peptides through the generation of wavelet subsequence templates derived from a variety of wavelet transformations of the physicochemically-transformed amino acid sequence of the target protein. The wavelet transformation method is particularly well suited for the study of localized coherent structures that appear across a target protein sequence, such as the patterns of alternating helices, loops and strands that make up larger supersecondary structures, such as helical barrels and sheets. A number of mother wavelet families are available for use in wavelet transformations.

The third method produces redundant target polypeptide or protein subsequence templates from the physicochemically-transformed amino acid sequence of the target polypeptide or protein. Redundant subsequence templates are prepared by converting the amino acid sequence of the target polypeptide or protein into a template through symbolic representations of each amino acid, e.g., one-letter amino acid codes or, more preferably, values representing each amino acid's membership in a particular physicochemical property grouping. The transformed target polypeptide or protein sequence is then scanned to find all possible redundant nonoverlapping subsequences. The redundant subsequences detected are used as templates to create mode-matching peptides.

It is therefore an object of the present invention to provide a method for synthesizing a peptide or a peptide-like molecule based on matching a physicochemical mode of a target polypeptide or protein to the same physicochemical mode of the peptide or peptide-like molecule, comprising the steps of assigning a numerical value of an orderable physicochemical property to each member of a set of peptide constituents which includes all the members of the set of naturally-occurring amino acids, arranging the peptide constituents in order of the numerical values of an orderable physicochemical property, partitioning the set of peptide constituents into a plurality of peptide constituent groups, whereby each of the peptide constituent groups contains at least one member of the set of peptide constituents, each peptide constituent group encompasses a range of the numerical values, each member of the set of peptide constituent belongs to only one peptide constituent group, creating a polypeptide physicochemical data series by replacing each amino acid in an amino acid sequence of the target polypeptide or protein with the numerical value of the orderable physicochemical property corresponding to each amino acid in the amino acid sequence, calculating one or more polypeptide eigenvalues and a corresponding polypeptide eigenvector associated with each of the polypeptide eigenvalues by linear decomposition of an autocovariance matrix formed from a sequentially lagged data matrix of the polypeptide physicochemical data series, ordering the polypeptide eigenvalues and the corresponding polypeptide eigenvectors from largest to smallest, selecting one or more of the polypeptide eigenvectors, transforming the selected polypeptide eigenvectors into an eigenvector template, forming a graph of the eigenvector template, wherein the numerical values of the physicochemical property are graphed along the y-axis of the graph and ordered position in the eigenvector template is graphed along the x-axis of the graph, partitioning the graph along the y-axis according to the ranges of the numerical values of the physicochemical property defining the peptide constituent groups to form a plurality of y-axis ranges, assigning a member of the peptide constituent group to each position in the peptide or peptide-like molecule by using the graph as a template, wherein at each ordered position in the eigenvector template along the x-axis of the graph, the member of the peptide constituent group assigned to the ordered position has a value of the orderable physicochemical property that is within the y-axis range of the ordered point, and synthesizing the peptide or peptide-like molecule.

It is another object of the present invention to provide a method for matching a physicochemical mode of a peptide or a peptide-like molecule to the same physicochemical mode of a target polypeptide or protein to determine if the peptide will bind to and/or otherwise modulate the target polypeptide or protein, comprising the steps of assigning a numerical value of an orderable physicochemical-property to each member of a set of peptide constituents which includes all the members of the set of naturally-occurring amino acids, arranging the peptide constituents in order of the numerical values of the orderable physicochemical property, partitioning the set of peptide constituents into a plurality of peptide constituent groups, whereby each of the peptide constituent groups contains at least one member of the set of peptide constituents, each peptide constituent group encompasses a range of the numerical values, each member of the set of peptide constituents belongs to only one peptide constituent group, creating a polypeptide physicochemical data series by replacing each amino acid in an amino acid sequence of the target polypeptide or protein with the numerical value of the orderable physicochemical property corresponding to each amino acid in the amino acid sequence, calculating one or more polypeptide eigenvalues and a corresponding polypeptide eigenvector associated with each of the polypeptide eigenvalues by linear decomposition of an autocovariance matrix formed from a sequentially lagged data matrix of the polypeptide physicochemical data series, ordering the polypeptide eigenvalues and the corresponding polypeptide eigenvectors from largest to smallest, transforming the polypeptide physicochemical data series into one or more polypeptide eigenfunctions, using the ordered polypeptide eigenvectors as multiplicative weights, transforming the polypeptide eigenfunctions into dominant wavenumbers, using all poles maximum entropy power spectra, to produce polypeptide spectral power peaks, identifying the polypeptide power spectral peaks, creating a peptide physicochemical data series by replacing each peptide constituent in a peptide sequence of the peptide or a peptide-like molecule with the numerical value of the orderable physicochemical property corresponding to the peptide constituent in the peptide sequence, calculating one or more peptide eigenvalues and a corresponding peptide eigenvector associated with each of the peptide eigenvalues by linear decomposition of an autocovariance matrix formed from the peptide physicochemical data series, ordering the peptide eigenvalues and the corresponding eigenvectors from largest to smallest, transforming the peptide physicochemical data series into one or more peptide eigenfunctions, using the ordered peptide eigenvectors as multiplicative weights, transforming the peptide eigenfunctions into dominant wavenumbers, using all poles maximum entropy power spectra, to produce peptide spectral power peaks, identifying the peptide power spectral peaks, and comparing the polypeptide spectral power peaks to the peptide spectral power peaks to determine if the polypeptide spectral power peaks match the peptide spectral power peaks, wherein a match between the polypeptide spectral power peaks and the peptide spectral power peaks indicates the peptide or peptide-like molecule may bind to and/or otherwise modulate the target polypeptide or protein.

It is another object of the present invention to provide a method for matching a peptide or a peptide-like molecule to a target polypeptide or protein to determine if the peptide will bind to and/or otherwise modulate the target polypeptide or protein, comprising the steps of assigning a numerical value of an orderable physicochemical property to each member of a set of peptide constituents, the set of peptide constituents including all the members of the set of naturally-occurring amino acids, arranging the peptide constituents in order of the numerical values of the orderable physicochemical property, partitioning the set of peptide constituents into a plurality of peptide constituent groups, whereby each of the peptide constituent groups contains at least one member of the set of peptide constituents, each peptide constituent group encompasses a range of the numerical values, each member of the set of peptide constituents belongs to only one peptide constituent group, creating a polypeptide physicochemical data series by replacing each amino acid in an amino acid sequence of the target polypeptide or protein with the numerical value corresponding to the amino acid in the amino acid sequence, decomposing the polypeptide physicochemical data series into translated and scaled version of a mother wavelet, w, as $$W^R(a, b) = (1/\sqrt{a}) \int_0^i H(i) w\left(\frac{i-b}{a}\right) di$$

wherein w denotes the chosen mother wavelet function, separating $W^R(a,b)$ into polypeptide modulus and polypeptide phase parts, graphing the polypeptide phase parts on a polypeptide phase graph, wherein the x-axis of the polypeptide phase graph indexes sequence position and the y-axis of the polypeptide phase graph is numbered in units of one of dilate divisions (dd) and wavelet wavelengths ($\bar{\omega}$), graphing the polypeptide modulus parts on a polypeptide modulus graph, wherein the x-axis of the polypeptide modulus graph indexes sequence position and the y-axis of the polypeptide modulus graph is numbered in units of one of dilate divisions (dd) and wavelet wavelengths ($\bar{\omega}$), identifying a plurality of polypeptide maximal phase amplitudes and a plurality of polypeptide moduli in the polypeptide phase graph and the polypeptide modulus graph, respectively, creating a peptide physicochemical data series by replacing each peptide constituent in a peptide sequence of the peptide or a peptide-like molecule with the numerical value of the orderable physicochemical property corresponding to each the peptide constituent in the peptide sequence, decomposing the peptide physicochemical data series into translated and scaled version of a mother wavelet, w, as $$W^L(a,b) = (1/\sqrt{a}) \int_0^i H(i) w\left(\frac{i-b}{a}\right) di$$

wherein w denotes the chosen mother wavelet function, separating $W^L(a,b)$ into peptide modulus and peptide phase parts, graphing the peptide phase parts on a peptide phase graph, wherein the x-axis of the peptide phase graph indexes sequence position and the y-axis of the peptide phase graph is numbered in units of one of relative dilation (dd) and wavelet wavelengths ($\bar{\omega}$), graphing the peptide modulus parts on a peptide modulus graph, wherein the x-axis of the peptide modulus graph indexes sequence position and the y-axis of the peptide modulus graph is numbered in units of one of dilate divisions (dd) and wavelet wavelengths ($\bar{\omega}$), identifying a plurality of peptide maximal phase amplitudes and a plurality of peptide moduli in the peptide phase graph and the peptide modulus graph, respectively, comparing the plurality of polypeptide maximal phase amplitudes in the polypeptide phase graph to the plurality of peptide maximal phase amplitudes in the peptide phase graph to determine if the plurality of polypeptide maximal phase amplitudes match the plurality of peptide maximal phase amplitudes, comparing the plurality of polypeptide moduli in the polypeptide modulus graph to the plurality of peptide moduli in the peptide modulus graph to determine if the plurality of polypeptide moduli match the plurality of peptide moduli, wherein a match between the plurality of polypeptide maximal phase amplitudes and the plurality of peptide maximal phase amplitudes, and a match between the plurality of polypeptide moduli and the plurality of peptide moduli, indicates the peptide or peptide-like molecule may bind to and/or otherwise modulate the polypeptide.

It is another object of the present invention to provide a method for matching a peptide or a peptide-like molecule to a target polypeptide or protein to determine if the peptide will bind to and/or otherwise modulate the target polypeptide or protein, comprising the steps of assigning a numerical value of an orderable physicochemical property to each member of a set of peptide constituents, the set of peptide constituents including all the members of the set of naturally-occurring amino acids, arranging the peptide constituents in order of the numerical values of the orderable physicochemical property, partitioning the set of peptide constituents into a plurality of peptide constituent groups, whereby each of the peptide constituent groups contains at least one member of the set of peptide constituents, each group encompasses a range of the numerical values, each member of the set of peptide constituents belongs to only one peptide constituent group, creating a polypeptide physicochemical data series by replacing each amino acid in an amino acid sequence of the target polypeptide or protein with the numerical value corresponding to the amino acid in the amino acid sequence, decomposing the polypeptide physicochemical data series with a family of functions $W_{j,n,k}(x)=2^{-j/2}W_n(2^{-j}x-k)$, which when j,n are positive integers and k has an integer value, are organized in one or more tree structures, each of the tree structures being composed of a plurality of nodes, each of the nodes being in the form of:

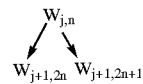

wherein $W_{j,n,k}(x)$ is computed for a mother wavelet function, computing and frequency ordering best level and best tree representations of a physicochemical polypeptide series based on Stein's Unbiased Risk Estimate (SURE) and Shannon entropy criteria, graphing the best level representation on a polypeptide best level graph, wherein the x-axis of the polypeptide best level graph indexes sequence position and the y-axis of the polypeptide best level graph is numbered in units of wavelet wavelengths, $\bar{\omega}$, graphing the best tree representation on a polypeptide best tree graph, wherein the x-axis of the polypeptide best tree graph indexes sequence position and the y-axis of the polypeptide best tree graph is numbered in units of one of relative dilation (dd) and wavelet wavelengths, $\bar{\omega}$, identifying a plurality of polypeptide maximal coefficient amplitudes, each of the plurality of polypeptide maximal coefficient amplitudes being derived from the polypeptide best level graph and the polypeptide best tree graph, creating a peptide physicochemical data series by replacing each peptide constituent in a peptide sequence of the peptide or a peptide-like molecule with the numerical value of the orderable physicochemical property corresponding to the peptide constituent in the peptide sequence, decomposing the peptide physicochemical data series with the family of functions $W_{j,n,k}(x)=2^{-j/2}W_n(2^{-j}x-k)$, which when j,n are positive integers and k has an integer value, are organized in one or more tree structures, each of the tree structures being comprised of a plurality of nodes, each of the nodes being in the form of

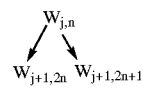

wherein $W_{j,n,k}(x)$ is computed for a mother wavelet function, computing and frequency ordering best level and best tree representations of a physicochemical peptide series based on SURE and Shannon entropy criteria, graphing the best level representation on a peptide best level graph, wherein the x-axis of the peptide best level graph indexes sequence position and the y-axis of the peptide best level graph is numbered in units of wavelet wavelengths, $\bar{\omega}$, graphing the best tree representation on a peptide best tree graph, wherein the x-axis of the peptide best tree graph indexes sequence position and the y-axis of the peptide best tree graph is numbered in units of one of relative dilation (dd) and wavelet wavelengths, $\bar{\omega}$, identifying a plurality of peptide maximal coefficient amplitudes, each of the plurality of peptide maximal coefficient amplitudes being derived from the peptide best level graph and the peptide best tree graph, comparing the plurality of polypeptide maximal coefficient amplitudes to the plurality of peptide maximal coefficient amplitudes to determine if the plurality of polypeptide maximal coefficient amplitudes match the plurality of peptide maximal coefficient amplitudes, wherein a match between the plurality of polypeptide maximal coefficient amplitudes and the plurality of peptide maximal coefficient amplitudes indicates the peptide or peptide-like molecule may bind to and/or otherwise modulate the target polypeptide or protein.

It is another object to provide a method for modifying a non-peptide-responsive target polypeptide or protein to bind to and/or otherwise modulate a peptide or peptide-like molecule by modifying the sequence of the non-peptide-responsive target polypeptide or protein to match a physicochemical mode of the peptide or peptide-like molecule, comprising the steps of assigning a numerical value of an orderable physicochemical property to each member of a set of polypeptide constituents, the set of peptide constituents including all the members of the set of naturally-occurring amino acids, arranging the peptide constituents in order of the numerical values of the orderable physicochemical property, partitioning the set of peptide constituents into a plurality of peptide constituent groups, whereby each of the peptide constituent groups contains at least one member of the set of peptide constituents, each group encompasses a range of the numerical values, each member of the set of peptide constituents belongs to only one peptide constituent group, creating a polypeptide physicochemical data series by replacing each amino acid in an amino acid sequence of the non-peptide-responsive target polypeptide or protein with the numerical value corresponding to the amino acid in the amino acid sequence, calculating one or more polypeptide eigenvalues and a corresponding polypeptide eigenvector associated with each of the polypeptide eigenvalues by linear decomposition of an autocovariance matrix formed from the polypeptide physicochemical data series, ordering the polypeptide eigenvalues and the corresponding polypeptide eigenvectors from largest to smallest, transforming the polypeptide physicochemical data series into polypeptide eigenfunctions, using the ordered polypeptide eigenvectors as multiplicative weights, transforming the polypeptide eigenfunctions into dominant wavenumbers, using all poles maximum entropy power spectra to produce polypeptide spectral power peaks, identifying the polypeptide power spectral peaks, creating a peptide physicochemical data series by replacing each peptide constituent in a peptide sequence of the peptide or peptide-like molecule with a numerical value of the orderable physicochemical property corresponding to the peptide or peptide-like molecule constituent in the peptide sequence, calculating one or more peptide eigenvalties and a corresponding peptide eigenvector associated with each of the peptide eigenvalues by linear decomposition of an autocovariance matrix formed from the peptide physicochemical data series, ordering the peptide eigenvalues and the corresponding peptide eigenvectors from largest to smallest, transforming the peptide physicochemical data series into peptide eigenfunctions, using the peptide eigenvectors as multiplicative weights, transforming the peptide eigenfunctions into dominant wavenumbers, using all poles maximum entropy power spectra, to produce peptide spectral power peaks, identifying the peptide power spectral peaks, comparing the polypeptide spectral power peaks to the peptide spectral power peaks to determine if the polypeptide spectral power peaks match the peptide spectral power peaks, wherein a match between the polypeptide spectral power peaks and the peptide spectral power peaks indicates the peptide or peptide-like molecule may bind to and/or otherwise modulate the non-peptide-responsive target polypeptide or protein, and if the polypeptide spectral power peaks do not match the peptide spectral power peaks, modifying the amino acid sequence of the non-peptide-responsive target polypeptide or protein to form a match between the polypeptide spectral power peaks and the peptide spectral power peaks.

It is a further object to provide a method for modifying a non-peptide-responsive target polypeptide or protein to bind to and/or otherwise modulate a peptide or peptide-like molecule by modifying the sequence of the non-peptide-binding/modulating target polypeptide to match a physicochemical mode of the peptide or peptide-like molecule, comprising the steps of assigning a numerical value of an orderable physicochemical property to each member of a set of peptide constituents, the set of peptide constituents including all the members of the set of naturally-occurring amino acids, arranging the peptide constituents in order of the numerical values of the orderable physicochemical property, partitioning the set of peptide constituents into a plurality of peptide constituent groups, whereby each of the peptide constituent groups contains one or more members of the set of peptide constituents, each group encompasses a range of said numerical values, each member of the set of peptide constituents belongs to only one peptide constituent group, creating a polypeptide physicochemical data series by replacing each amino acid in an amino acid sequence of the non-peptide-binding and/or modulating target polypeptide or protein with a numerical value corresponding to each the amino acid in the amino acid sequence, decomposing the polypeptide physicochemical data series into translated and scaled version of a mother wavelet, w, as $$W^R(a,b) = \left(1/\sqrt{a}\right)\int_0^i H(i)w\left(\frac{i-b}{a}\right)di$$

wherein w denotes the chosen mother wavelet function, separating $W^R$(a,b) into polypeptide modulus and polypeptide phase parts, graphing the polypeptide phase parts on a polypeptide phase graph, wherein the x-axis of the polypeptide phase graph indexes sequence position and the y-axis of the polypeptide phase graph is numbered in units of one of relative dilation (dd) and wavelet wavelengths $(\overline{\omega})$, graphing the polypeptide modulus parts on a polypeptide modulus graph, wherein the x-axis of the polypeptide modulus graph indexes sequence position and the y-axis of the polypeptide modulus graph is numbered in units of one of relative dilation (dd) and wavelet wavelengths $(\overline{\omega})$, identifying a plurality of polypeptide maximal phase amplitudes and a plurality of polypeptide moduli in the polypeptide phase graph and the polypeptide modulus graph, respectively, creating a peptide physicochemical data series by replacing each peptide constituent in a peptide sequence of a peptide or a peptide-like molecule with the numerical value corresponding to each peptide constituent in the peptide sequence, decomposing the peptide physicochemical data series into translated and scaled version of a mother wavelet, w, as $$W^L(a,b) = \left(1/\sqrt{a}\right)\int_0^i H(i)w\left(\frac{i-b}{a}\right)di$$

wherein w denotes the chosen mother wavelet function, separating $W^L$(a,b) into peptide modulus and peptide phase parts, graphing the peptide phase parts on a peptide phase graph, wherein the x-axis of the peptide phase graph indexes sequence position and the y-axis of the peptide phase graph is numbered in units of one of relative dilation (dd) and wavelet wavelengths $(\overline{\omega})$, graphing the peptide modulus parts on a peptide modulus graph, wherein the x-axis of the peptide modulus graph indexes sequence position and the y-axis of the peptide modulus graph is numbered in units of one of relative dilation (dd) and wavelet wavelengths $(\overline{\omega})$, identifying a plurality of peptide maximal phase amplitudes and a plurality of peptide moduli in each of the peptide phase graph and the peptide modulus graph, respectively, comparing the plurality of polypeptide maximal phase amplitudes in the polypeptide phase graph to the plurality of peptide maximal phase amplitudes in the peptide phase graph respectively to determine if the plurality of polypeptide maximal phase amplitudes match the plurality of peptide maximal phase amplitudes, comparing the plurality of polypeptide moduli in the polypeptide modulus graph to the plurality of peptide moduli in the peptide modulus graph to determine if the plurality of polypeptide moduli match the plurality of peptide moduli, wherein a match between the plurality of polypeptide maximal phase amplitudes and the plurality of peptide maximal phase amplitudes, and a match between the plurality of polypeptide moduli and the plurality of peptide moduli indicates the peptide or peptide-like molecule may bind to and/or otherwise modulate the non-peptide-binding and/or modulating target polypeptide or protein, and if the plurality of polypeptide maximal phase amplitudes do not match the plurality of peptide maximal phase amplitudes, or if the plurality of polypeptide moduli do not match the plurality of peptide moduli, modifying the amino acid sequence of the non-peptide-binding and/or modulating target polypeptide or protein to form a match between the plurality of polypeptide maximal phase amplitudes and the plurality of peptide maximal phase amplitudes, and between the polypeptide moduli and the peptide moduli.

It is a further object to provide a method for modifying a non-peptide-responsive target polypeptide or protein to bind to and/or otherwise modulate a peptide or peptide-like molecule by modifying the sequence of the non-peptide-responsive target polypeptide or protein to match a physicochemical mode of the peptide or peptide-like molecule, comprising the steps of assigning a numerical value of an orderable physicochemical property to each member of a set of peptide constituents, the set of peptide constituents including all the members of the set of naturally-occurring amino acids, arranging the peptide constituents in order of the numerical values of the orderable physicochemical property, partitioning the set of peptide constituents into a plurality of peptide constituent groups, whereby each of the peptide constituent groups contains one or more members of the set of peptide constituents, each group encompassing a range of said numerical values, each member of the set of peptide constituents belongs to only one peptide constituent group, creating a polypeptide physicochemical data series by replacing each amino acid in an amino acid sequence of the non-peptide-binding and/or modulating target polypeptide or protein with the numerical value of the orderable physicochemical property corresponding to the amino acid in the amino acid sequence, decomposing the polypeptide physicochemical data series with a family of functions $W_{j,n,k}(x)=2^{-j/2}W_n(2^{-j}x-k)$, which when j,n are positive integers and k has an integer value, are organized in one or more tree structures, each of the tree structures being comprised of a plurality of nodes, each of the nodes being in the form of:

$$\begin{array}{ccc} & W_{j,n} & \\ \swarrow & & \searrow \\ W_{j+1,2n} & & W_{j+1,2n+1} \end{array}$$

wherein the $W_{j,k,n}(x)$ is computed for a mother wavelet function, computing and frequency ordering best level and best tree representations of the physicochemical polypeptide series based on SURE and Shannon entropy criteria, graphing the best level representation on a polypeptide best level graph, wherein the x-axis of the polypeptide best level graph indexes sequence position and the y-axis of the polypeptide best level graph is numbered in units of wavelet wavelengths, $\overline{\omega}$, graphing the best tree representation on a polypeptide best tree graph, wherein the x-axis of the polypeptide best tree graph indexes sequence position and the y-axis of the polypeptide best tree graph is numbered in units of one of relative dilation (dd) and wavelet wavelengths, $\overline{\omega}$, identifying a plurality of polypeptide maximal coefficient amplitudes, each of the plurality of polypeptide maximal coefficient amplitudes being derived from the polypeptide best level and best tree graphs, decomposing the peptide physicochemical data series with a family of functions $W_{j,n,k}(x)=2^{-j/2}W_n(2^{-j}x-k)$, which when j,n are positive integers and k has an integer value, are organized in one or more tree structures, each of the tree structures being comprised of a plurality of nodes, each of the nodes being in the form of:

$$\begin{array}{ccc} & W_{j,n} & \\ \swarrow & & \searrow \\ W_{j+1,2n} & & W_{j+1,2n+1} \end{array}$$

wherein the $W_{j,n,k}(x)$ is computed a mother wavelet function, computing and frequency ordering best level and best tree representations of the physicochemical peptide series based on SURE and Shannon entropy criteria, graphing the best level representation on a peptide best level graph, wherein the x-axis of the peptide best level graph indexes sequence position and the y-axis of the peptide best level graph is numbered in units of wavelet wavelengths, $\overline{\omega}$, graphing the best tree representation on a peptide best tree graph, wherein the x-axis of the peptide best tree graph indexes sequence position and the y-axis of the best tree graph is numbered in units of one of relative dilation (dd) and wavelet wavelengths, $\overline{\omega}$, identifying a plurality of peptide maximal coefficient amplitudes, each of the plurality of peptide maximal coefficient amplitudes being derived from the peptide best level and best tree graphs, comparing the plurality of polypeptide moduli in the polypeptide modulus graph to the plurality of peptide moduli in the peptide modulus graph to determine if the plurality of polypeptide moduli match the plurality of peptide moduli, wherein a match between the plurality of polypeptide maximal phase amplitudes and the plurality of peptide maximal phase amplitudes, and a match between the plurality of polypeptide moduli and the plurality of peptide moduli indicates the peptide or peptide-like molecule may bind to and/or otherwise modulate the non-peptide-binding and/or modulating target polypeptide or protein, and if the plurality of polypeptide maximal phase amplitudes do not match the plurality of peptide maximal phase amplitudes, or if the plurality of polypeptide moduli do not match the plurality of peptide moduli, modifying the amino acid sequence of the non-peptide-binding and/or modulating target polypeptide or protein to form a match between the plurality of polypeptide maximal phase amplitudes and the plurality of peptide maximal phase amplitudes, and between the polypeptide moduli and the peptide moduli.

The present invention also provides a method of detecting a cancerous cell or tissue, comprising contacting all or a portion of the cancerous cell or tissue with an effective amount of a peptide or peptide-like molecule having a physicochemical mode that matches a physicochemical mode of a target polypeptide or protein found on the cancerous cell or tissue.

The present invention also provides a method of detecting a tumor in a patient, comprising administering to the patient an effective amount of a peptide or peptide-like molecule having a physicochemical mode that matches a physicochemical mode of a polypeptide or protein found on the tumor, and detecting binding and/or modulating of the peptide or peptide-like molecule to the polypeptide or protein.

The present invention also provides a pharmaceutical composition for treatment of a tumor, comprising a peptide or peptide-like molecule having a physicochemical mode that matches a physicochemical mode of a polypeptide or protein found on the tumor, and a pharmaceutically acceptable carrier.

The present invention also provides a diagnostic kit for use in detecting a polypeptide or protein, comprising a container having a peptide or peptide-like molecule, the peptide or peptide-like molecule having a physicochemical mode that matches a physicochemical mode of the polypeptide or protein.

The present invention also provides a method for screening for a disease condition, comprising contacting a sample obtained from a patient with an effective amount of a peptide or peptide-like molecule having a physicochemical mode that matches a physicochemical mode of a polypeptide or protein found in the sample, wherein the presence, absence or abnormality in the polypeptide or protein is diagnostic of the presence of the disease condition.

The present invention also provides a method for screening a member selected from the group consisting of water, food, and soil for the presence of a contaminant, comprising contacting the member with a peptide or peptide-like molecule having a physicochemical mode that matches a physicochemical mode of a polypeptide or protein found in the member, wherein the presence, absence, or abnormality in the polypeptide or protein is diagnostic of the presence of the contaminant.

The present invention also provides a method for treating a disease condition, comprising administering to a patient in need of such treatment a peptide or peptide-like molecule having a physicochemical mode that matches a physicochemical mode of a polypeptide or protein found in the sample, wherein the peptide or peptide-like molecule is capable of effecting a direct action and/or modulation of an activity of the polypeptide or protein, and the direct action and/or modulation effected by the peptide or peptide-like molecule is associated with a change in the disease condition.

The present invention also provides a method for detecting an interaction between a peptide and a target polypeptide or protein, comprising incubating a peptide prepared by at least one of the methods of the present invention with the target polypeptide or protein under conditions that promote the interaction of the peptide with the target polypeptide or protein, and detecting the interaction of the peptide with the target polypeptide or protein.

The present invention also provides a pharmaceutical composition for treatment of a disease condition, comprising a peptide or peptide-like molecule having a physicochemical mode that matches a physicochemical mode of a polypeptide or protein found in the sample, the peptide or peptide-like molecule being capable of effecting a direct action and/or modulation of an activity of the polypeptide or protein, and the direct action and/or modulation effected by the peptide or peptide-like molecule is associated with a change in the disease condition, and a pharmaceutically acceptable carrier.

The above and other objects, features and advantages of the present invention will become apparent from the following description read in conjunction with the accompanying drawings. dr

DETAILED DESCRIPTION OF THE PREFERRED EMBODIMENTS

The present invention discloses methods to create mode-matched peptides that have a high probability of binding to and/or modulating the function of target peptides, polypeptides, or proteins. The peptides are constructed from peptide templates derived from physicochemical transformations of the amino acid sequences of the target peptide, polypeptide, or protein. In particular, the templates are derived from at least one of the following: 1) eigenvectors of the autocovariance matrices of the physicochemically transformed amino acid sequence of the target protein; 2) wavelet subsequence templates derived from a variety of wavelet transformations of the physicochemically transformed amino acid sequence of the target protein; and 3) redundant subsequence templates computed from the physicochemically transformed amino acid sequence of the target protein.

Figure 1:
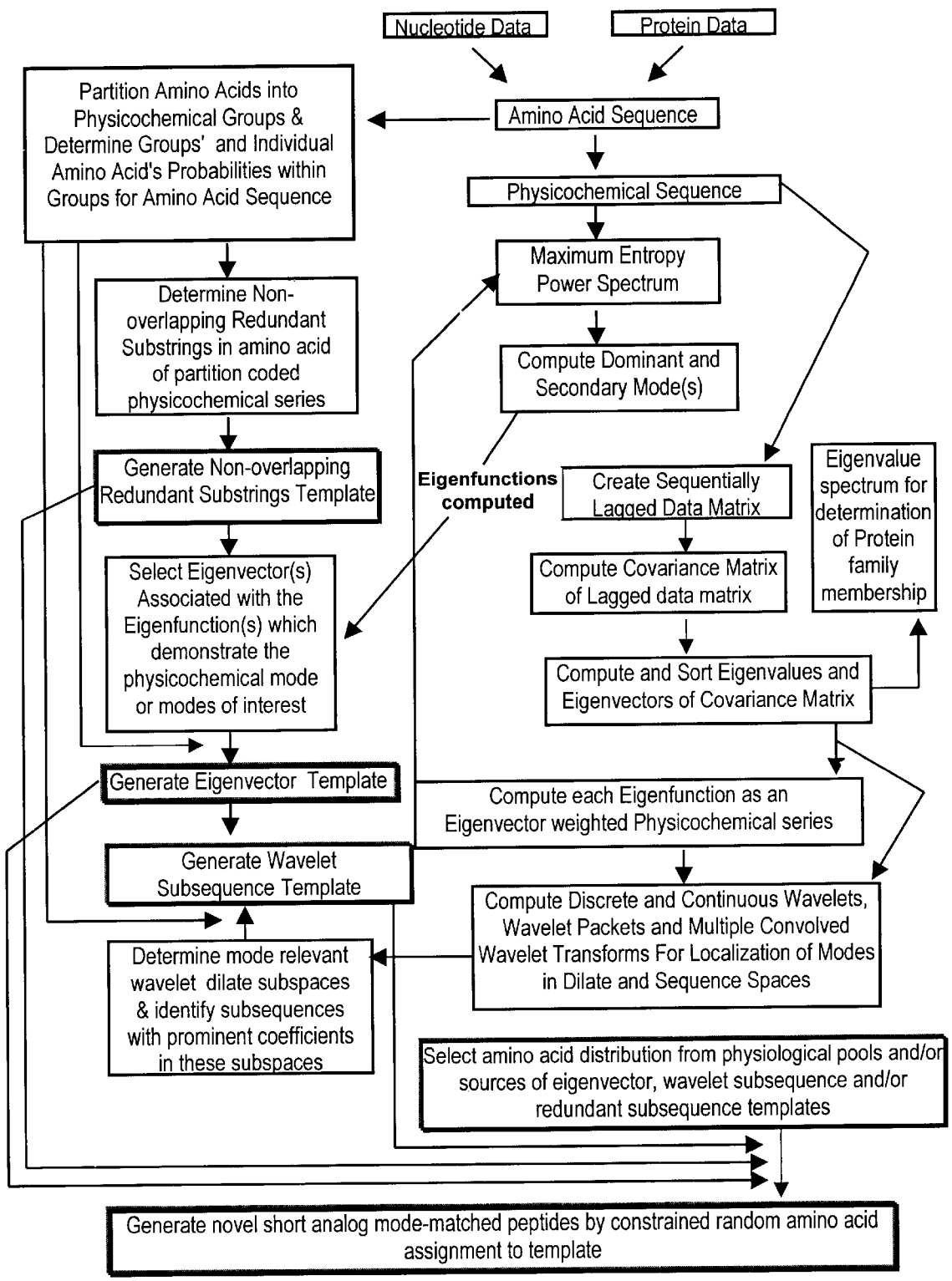
FIG. 1 is a flowchart which summarizes the methods of the present invention.

In the peptide design methods described herein, we make new use of three techniques to characterize the dominant statistical wavelengths of a target polypeptide's physicochemical property mode (or modes) in order to generate templates for the construction of mode-matched peptides having a high probability of binding to and/or otherwise modulating, inhibiting or activating activity of the target protein, polypeptide or peptide (FIG. 1). The techniques are: (1) eigenfunction(s) construction from the convolution of the eigenvector(s) with an original data series, in which the eigenvector(s) is determined from the autocovariance matrices of a sequentially lagged physicochemical property data series of the peptides, polypeptides and proteins; (2) all poles, maximum entropy power spectral transformation (in contrast to standard Fourier transformed power spectra) of the eigenfunction(s), which identifies the mode content of the physicochemical property data series or their eigenfunctions; and (3) discrete and continuous wavelet transformations, one-dimensional wavelet packets and multiple convolved wavelets (using a range of potential mother wavelets as listed above) which confirm the dominant statistical wavelengths of the eigenfunctions and locate them as phase amplitudes or absolute valued moduli in the constituent sequences. Additionally, as described in detail below, the results of the wavelet transformations may locate one or more subsequences of the polypeptide that can serve as a wavelet subsequence template or an amino acid distribution source in the design of peptide or peptide-like molecules, or both. Similarly, a symbolic or literal template can be created directly from the subsequences so selected, or through the decomposition of single or multiple concatenated subsequences, to create a non-overlapping redundant subsequence template. The spectral modes of the polypeptides or proteins that emerge from the power spectra and wavelet transformations dictate the choice(s) of the eigenvector(s), alone or summed, which can then be used as templates for the construction of mode-matching peptides. The template then may be used in the manner described below to generate peptide ligands having a high probability of binding to and/or otherwise modulating the activity of the target polypeptide or protein.

The array of potential target peptides, polypeptides, or proteins may include, without limitation, cell membrane receptors, nuclear membrane receptors, circulating receptors, enzymes, membrane and circulating transporters, membrane proteins involved in the translocation of viral and other infective agents into the cell, chaperonins and chaperonin-like proteins, monoclonal antibodies and antibody derivatives, such as Fc, Fab', F(ab')$_2$, Fv or scFv fragments; and generally any protein, polypeptide or peptide involved in peptide-protein and/or protein-protein interactions.

Generally, the first method of the present invention involves the linear decomposition of M-lagged, autocovariance matrices, $C_M$, constructed from the sequentially lagged data matrix of $H_{i,i=1\ldots N}$'S of N-length membrane proteins. M is often (but not always) chosen to optimize the least squares fit of the protein's leading eigenfunction with its hydropathy plot, because, particularly in the case of the seven-transmembrane receptors, the graphs of the leading eigenfunctions closely resemble those of the target protein's smoothed hydropathy sequence, created by the repeated application of nearest neighbor averaging of the $H_{i,i=1\ldots N}$. From the set of ordered eigenvalues, $\{v_i\}_{i=1\ldots M}$ of the $C_M$, the corresponding set of ordered eigenvectors, $X_{i,i=1\ldots M}$ are computed and serially convolved with $H_{i,i=1\ldots N}$ to form an ordered set of hydrophobic free energy eigenfunctions, $\Psi_{i,i=1\ldots M}$, each of length N−M+1. An alternative eigenfunction computation, described below, results in eigenfunctions of length N. The ordered eigenvalue spectra generally decay quickly after the first few leading ordered values, such that most if not all of the transmembrane and peptide binding/modulating mode information is captured in the first few eigenvalues, i.e., $\{v_i\}_{i=1\ldots 4}$, although 8<M<25 may be employed as required for adequate separation and resolution.

Next, the hydrophobic mode content of the $\Psi_i$'s containing the peptide-binding/modulating inverse spatial frequency mode (expressed as a wavenumber, $\omega^{-1}$, in units of amino acids) is identified using all poles, maximum entropy power spectral transformations $S(\omega)$ and/or wavelet transformations $W(a,b)$. These methods revealed sets of statistical wavenumber matches between peptide ligands and their corresponding membrane receptor proteins, ranging from $\omega^{-1} \approx 2-14$ amino acids across examples. Estimating the dominant wavenumber content of secondary eigenfunctions, $\Psi_2$, using all poles, maximum entropy power spectral transformations, $S(\omega)$, and/or discrete and continuous wavelet and one dimensional wavelet packet transformations $W(a,b)$, led to clearly resolved mode matches between peptide ligands and their receptors, and predicted kinetic interactions between $\Delta G_{hp}$ sequential mode-matched peptide ligands and the receptors. Matches as statistical patterns in $\Delta G_{hp}$ modes were found between peptide ligands and their membrane receptors, including kappa, mu, delta and orphan opiate receptors, corticotropin releasing factor receptor, cholecystokinin receptor, neuropeptide Y receptor, somatostatin receptor, bombesin receptor, and neurotensin receptor. $\Delta G_{hp}$ mode matches, such as those found between the dopamine co-localized neuropeptide neurotensin and the D$_2$ dopamine membrane receptor, D$_2$DA, and those found between the gastrointestinal and brain peptide cholecystokinin and the dopamine membrane transporter, DAT, predicted the differential binding of the pharmacologically active ligands to their respective responsive dopamine membrane receptors and, correspondingly, their lack of binding to the opposing, pharmacologically unresponsive dopamine membrane receptors.

While the present invention is described below by employing the hydrophobic free energies ($\Delta G_{hp}$) of the twenty naturally-occurring amino acids, in generating potential receptor binding and/or modulating peptides other quantifiable physicochemical properties that can order the amino acids along a particular physicochemical dimension of varying continuity may be used in place of the hydrophobic free energies. Other amino acid physicochemical properties that may be considered in choosing the appropriate physicochemical property include, without limitation, relative vapor pressure, relative free energy of amino acid transfer into bulk phases, amino acid partition coefficients in other solvent systems, diffusivity, frictional coefficient, aqueous cavity surface area, aqueous molar volume, partial specific volume, accessible surface area, charge, mass (in daltons), volume, $pK_a$ of ionizing side chain, chromatographic mobility, electrophoretic mobility, chemical categorical membership (nonpolar aliphatic, nonpolar aromatic, polar uncharged, polar charged, basic-positively charged, acidic-negatively charged, sulfur-containing), structure breakers (proline, glycine), and relative occurrence in specific or groups of proteins (as percents). Other published properties are known to those in the art and available, for example, on the World Wide Web site http:/www.expasy.ch. It is generally known from physicochemical studies that there are relatively high correlations (r=0.6–0.8) among the values for the twenty naturally-occurring amino acids of free energy of transfer from aqueous to hydrophobic solvents (i.e., hydrophobic free energy), relative vapor pressure, aqueous cavity surface area, aqueous molar volume, partial specific volume, solvent accessible surface area, and other physicochemical properties. As a result, the results obtained from any of these quantifiable physicochemical properties would be expected to apply equally to the remainder of the quantifiable physicochemical properties.

The eigenfunctions used in the eigenvector-based method are related to the Karhunen-Loeve, principal components and factor analysis transformations, and are uniquely defined in terms of an eigenvalue decomposition of each hydrophobic free energy data set, resulting in a set of hydrophobic free energy eigenvector-weighted eigenfunctions. Where available, the set of characteristic hydrophobic free energy wavelengths are isolated in the extracellular domains of transmembrane receptors. For example, the leading eigenfunction, $\Psi_1$, associated with the largest eigenvalue of the covariance matrix of a seven-transmembrane receptor sequence locates the same transmembrane segments as are seen in conventional n-block averaged hydropathy plots. However, unlike the case with n-block averaged hydropathy plots, the eigenfunctions generated by the methods of the present invention leave the remaining secondary hydrophobic mode (or modes) unsmoothed and available for further analyses as secondary eigenfunctions (i.e., $\Psi_2$, $\Psi_3$, . . . ). The eigenvectors associated with these secondary eigenfunctions may then be used as templates for the construction of mode-matched peptides or peptide-like molecules that then may be tested for their ability to bind to and modulate, activate and/or inhibit the function of the seven-transmembrane receptors. For other, non-seven-transmembrane receptor sequences, such as, for example, the human NGF receptor, the eigenvectors associated with the leading eigenfunctions may be suitable for use as peptide construction templates, since these hydrophobic modes are not likely to be dominated by transmembrane segments, as in the case of seven-transmembrane receptors.

Alternatively, templates may be created using other methods which incorporate the results of discrete or continuous wavelet transformations, one-dimensional wavelet packet transformations or the convolution of the coefficients of two or more wavelet transformations. These transformations locate one or more subsequences of the target polypeptide that can serve as a symbolic or literal wavelet template, derived directly from the subsequences so selected or through the decomposition of single or multiple concatenated subsequences to create an eigenvector template. Still other templates may be created through the identification of symbolic or literal amino acid redundant subsequences in the polypeptide and peptides or peptide-like molecules known or believed to bind to and/or otherwise modulate the target polypeptide.

The methods of the present invention are described in detail below, using the example of hydrophobic free energy as.the physicochemical property. As noted above, the correlations among the various physicochemical parameters enable general use of the methods of the present invention with other physicochemical properties, and one of ordinary skill in the art would appreciate that no undue experimentation would be required to perform the methods of the present invention using other physicochemical properties.

A hydrophobic free energy series, $H_i$, is established for the twenty naturally-occurring amino acids. The values are normalized such that the reference amino acid, glycine, without a secondary structure-forming side chain, is set equal to 0.00. The values for $H_i$ of each of the twenty naturally occurring amino acids cluster naturally into four groups, as shown in Table 1.

TABLE 1

| Group I | | Group II | | Group III | | Group IV | |
| --- | --- | --- | --- | --- | --- | --- | --- |
| Amino Acid/Symbol | $H_i$ (kcal/mol) | Amino Acid/Symbol | $H_i$ (kcal/mol) | Amino Acid/Symbol | $H_i$ (kcal/mol) | Amino Acid/Symbol | $H_i$ (kcal/mol) |
| tryptophan/W | 3.77 | cysteine/C | 1.52 | alanine/A | 0.87 | serine/S | 0.07 |
| tyrosine/Y | 2.76 | methionine/M | 1.67 | aspartate/D | 0.66 | threonine/T | 0.07 |
| phenylalanine/F | 2.87 | valine/V | 1.87 | histidine/H | 0.87 | glycine/G | 0.00 |
| isoleucine/I | 3.15 | lysine/K | 1.64 | arginine/R | 0.85 | glutamine/Q | 0.00 |
| proline/P | 2.77 | leucine/L | 2.17 | glutamate/E | 0.67 | asparagine/N | 0.09 |

The set of hydrophobic free energy values naturally clusters into four discontinuous groups, with two exceptions. Proline (P), though having a value of 2.77 kcal/mol which places it in the highest hydrophobicity group, acts as a secondary structure breaker, due to its rigid constraints on rotation about the N—Cα bond and absence of an amide hydrogen for resonance stabilization of its peptide bond or participation in carbonyl-imino H-bonding. Consequently, proline has unusual hydrogen binding inclinations and "breaks" the continuity of one-dimensional hydrophobic waves in the same way as its nucleotide complement partner in the lowest hydrophobicity group, glycine. Therefore, proline is assigned to the lowest hydrophobicity group with glycine and is given the same value (see Table 2). In addition, leucine has many of the properties of the highest hydrophobicity group and is assigned to that group in place of proline. Therefore, the twenty naturally occurring amino acids are divided on the basis of the hydrophobic free energy values into four hydrophobicity groups consisting of the following amino acids: Group I (highest hydrophobicity): L,W,Y,F,I; Group II (second highest hydrophobicity): C,M, V,K; Group III (third highest (second lowest) hydrophobicity): A,D,H,R,E; and Group IV (lowest hydrophobicity): S,T,G,Q,N,P. These groupings are shown in Table 2.

used as multiplicative "weights" to transform the $H_1$, $H_2, \ldots, H_N$ into M statistically weighted eigenfunctions, $\Psi_i(j)$, where $i=1 \ldots M$ labels the eigenfunction and $j=1 \ldots N-M$ indexes its jth component. The $\Psi_i(j)$, for $j-k+1>0$, are given by $$\Psi_i(j) = \sum_{k=1}^{M} X_i(k) H_{j-k+1}$$

TABLE 2

| Group I | | Group II | | Group III | | Group IV | |
| --- | --- | --- | --- | --- | --- | --- | --- |
| Amino Acid/Symbol | $H_i$ (kcal/mol) | Amino Acid/Symbol | $H_i$ (kcal/mol) | Amino Acid/Symbol | $H_i$ (kcal/mol) | Amino Acid/Symbol | $H_i$ (kcal/mol) |
| leucine/L | 2.17 | cysteine/C | 1.52 | alanine/A | 0.87 | serine/S | 0.07 |
| tryptophan/W | 3.77 | methionine/M | 1.67 | aspartate/D | 0.66 | threonine/T | 0.07 |
| tyrosine/Y | 2.76 | valine/V | 1.87 | histidine/H | 0.87 | glycine/G | 0.00 |
| phenylalanine/F | 2.87 | lysine/K | 1.64 | arginine/R | 0.85 | glutamine/Q | 0.00 |
| isoleucine/I | 3.15 | | | glutamate/E | 0.67 | asparagine/N | 0.09 |
| | | | | | | proline/P | 0.00 |

The natural division of $H_i$ into four sets of four to six amino acids each (Tables 1 and 2) is used in assignment of amino acids to the four-partitioned eigenvector templates used in the construction of new candidate peptide ligands, while the values of $H_i$ in Table 2 are used in the transformation of the amino acid sequence of the receptor into a real number $\Delta G_{hp}$ series, as described below. It will be apparent to one of skill in the art that other groupings are potentially appropriate and that as other physicochemical properties are employed, the amino acids may group differently.

Each target polypeptide having an amino acid sequence of length N, comprised of amino acids $A_1, A_2, \ldots A_N$ may be represented as a sequence of hydrophobic free energy values $H_1, H_2 \ldots H_N$, where $H_i$ represents the hydrophobic free energy value of amino acid $A_i$ in the i-th place in the amino acid sequence, using the $H_i$ values listed in Table 2 above. Each target polypeptide sequence, $H_1, H_2, \ldots H_N$, is transformed first into a sequentially lagged data matrix, then into an autocovariance matrix, and finally decomposed into a set of orthogonal functions.

From the data column vectors (T=transpose) $V_1^T=(H_1, H_2 \ldots, H_{n-M})$, $V_2^T=(H_2, H_3, \ldots, H_{n-M+1}), \ldots, V_M^T=(H_M, H_{M+1}, \ldots, H_n)$ and where $K=n-M+1$, the sequence averaged dyadic product, $H_i H_i^T$ is used to obtain the autocovariance matrix, a Hermitean M×M matrix, $C_M=1/K\{H_i H_i^T\}$. M is sometimes chosen to minimize the least squares error of the protein's leading eigenfunction, $\Psi_1$, with their hydropathy plots resulting from the standard technique of nearest-neighbor averaging. As such, values for M are often in the range of about 10 to about 20.

The eigenvalues, $\{v_i\}_{i=1}^{M}$ and the associated eigenvectors, $X_i(j)$, of $C_M$, are calculated wherein $i=1 \ldots M$ and labels the eigenvector, and $j=1 \ldots M$ and refers to the jth component of the eigenvector $X_i(j)$. The eigenvalues $\{v_i\}_{i=1}^{M}$ are ordered from largest to smallest, as are the corresponding eigenvectors $X_i(j)$. The ordered $X_i(j)$ are then Alternatively, N length $\Psi_1(j)$, for $j>0$, are given by $$\Psi_i(j) = \sum_{k=1}^{M} X_i(k) H_j$$

Here $H_1$ is the first hydrophobic free energy value in the sequence. Intuitively, $C_M$ scans for hydrophobic modes across a range of autocorrelation lengths from 1 to M, the range of the lags in the autocovariance matrices. Because $C_M$ is real, symmetric ($H_{ij}=H_{ji}$) and normal ($C_M C_M^T = C_M^T C_M$), its $\{v_i\}_{i=1 \ldots M}$ are real, non-negative and distinct, and its associated eigenvectors, $X_i(j)$, constitute a natural basis for orthonormal projections on $H_1, H_2, \ldots, H_n$. The set of $\Psi_i(j)$ can be regarded as orthonormally decomposed sequences of eigenvector-weighted, moving average values.

The eigenfunctions may be shortened with respect to the receptor sequences by the number of lags M used to construct the covariance matrix. The leading eigenfunction representing the transmembrane segments of receptor proteins is designated as $\Psi^T$, the secondary eigenfunctions containing the peptide-binding/modulating receptor mode or modes as $\Psi^R$, and the leading peptide or peptide-like molecule ligand eigenfunction as $\Psi^L$ (when the peptide or peptide-like molecule is long enough to permit its construction). The eigenvectors serve as weights to generate orthonormally decomposed sequences of moving average values with the potential for finer resolution of mode or modes than that possible in the moving average graph of the hydropathy plot or Fourier transformation of the undecomposed data series.

In the computation of maximum entropy power spectral transformations, $S(\omega)$, the $a_k$ coefficients are calculated directly from the $H_i$ or $\Psi_i$ series, and represent the average over $H_i$ separated by k residues or values in the relevant $\Psi_i$ sequence such that $$a_k = \langle H(i)H(i+k)\rangle = \frac{1}{N-k}\sum_{i=1}^{N-k} H(i)H(i+k)$$

for N−M+1 points in the case of the $\Psi_i$. Where $z=e^{i\omega}$, the conventional Fourier power spectral transformation is inverted such that poles replace the zeros of the usual expansion; i.e., in $$S(\omega) = \frac{1}{\left|1 + \sum_{k=1}^{N-M+1} a_k z^k\right|^2},$$

where the denominator is a minimum, $S(\omega)$ will have peaks. It can be shown, using the method of Lagrange multipliers, that extending beyond the known $a_k$'s for k=−M . . . M into a Gaussian process maximizes the entropy, H, of $S(\omega)$, $H = \int \ln S(\omega)d\omega$ in the all poles power spectral transformation. Here, k is the number of poles chosen for examination and is usually (but not always) held to $\leq 8$ for receptor eigenfunctions derived from receptors having sequence lengths of several hundred amino acids to avoid "splitting" $S(\omega)$ into spurious modes. In the all poles maximum entropy power spectral transformation, $S(\omega)$ is much like an autoregressive, maximum-likelihood spectral estimate in that it is not mode-dependent, but is derived directly from the data of $H_{i,i=1\ldots n}$ and $\Psi$, and behaves like a filter that may yield the one or two leading poles of discrete hydrophobic variation in the hydrophobic free energy eigenfunction.

Wavelet Transformations of Hydrophobic Free Energy Functions

Whereas the $S(\omega)$ of the protein's leading $\Psi^R$ and its ligand's $\Psi^L$ locate the conjectured binding/modulating mode or modes in $\Delta G_{hp}$ wavelength space, their sequence position is lost. In contrast, wavelet transformations yield sequence and wavelength information simultaneously. Discrete wavelet techniques allow cutting smooth windows of differing lengths while preserving orthogonality during pattern identification in W.

Haar, Trigonometric, Meyer, Daubechies, Gabor, Battle-Lemarie, Biorthogonal, Coifman, Grossmann, Morlet, Mexican Hat and other mother wavelet families may be used in wavelet transformations that depict specific proteins as a signatory sequence of hierarchical modules. These functions are called wavelets because they have a local oscillatory form, so that, unlike the sinusoidal waves of Fourier transformation, they decay as $H \to \infty$. There are a wide variety of choices of "mother wavelets" which are systematically dilated, translated and then composed with the original sequence.

With respect to the hierarchical scaling characteristics, unlike the Fourier transform which sacrifices location for knowledge of characteristic wave numbers, the wavelet transformation is well suited to study regions of non-random autocorrelation which appear intermittently across a sequence and with hierarchies of scale. This is exemplified in proteins by the typical patterns of alternating helices, strands and loops as localized coherent structures along longer wavelengths of intermittent patterns of larger autocorrelated sequential structures, such as helical barrels and sheets. These, in turn, are components of still larger autocorrelated sequences in the form of protein domains.

With respect to hydrophobic free energy sequences, we have found that the Dubechies wavelets, and in particular its simplest member, the Haar wavelet, are usually better suited for locating structures in sequence space, while the Morlet, Meyer and Mexican Hat wavelets are best for indexing sequential structures in dilate space. The approach using the Morlet mother wavelet is presented here. However, it will be understood by those of skill in the art that other mother wavelets could also be employed, as desired. The wavelet method of locating, describing mode relevant subsequence and constructing wavelet subsequence templates from which to design peptides for binding, modulation, activation and/or inhibition of a target polypeptide/protein is has not been previously described and is unique to the present invention.

Assuming the protein structural organization that was first suggested by Linderstrøm-Lang and assuming, for example, 64 dilate divisions are in the wavelet graph, some or all of the following kinds of information are available from the Morlet wavelet transformations of an undecomposed $H_i$. First, at relatively small scales, the sequence locations and fundamental sequential hydrophobic inverse spatial frequencies or wavenumbers of the protein's characteristic secondary structures can be determined. For example, α-helices contain from 3.2 to 3.7 amino acids per hydrophobic free energy rotation ($\approx$24–30 dd), while β-strands have rotation numbers which may range between 2.2 to 2.6 amino acids ($\approx$5 to 15 dd). Second, at intermediate scales, the characteristic sequence sizes and locations of singular, hierarchical, secondary structures can be assessed. For example, although there is considerable variability, individual helices in helical bundles generally average in the range of 7 to 15 residues in length ($\approx$48 to 55 dd) and β-strands in sheets or barrels may range from 4 to 8 residues ($\approx$32 to 45 dd). Third, at the next largest scale, the multiresolution capacity of W(a,b) may be exploited to locate another kind of sequence similarity characteristic of the multiscale, hydrophobic sequence content of the longer and shorter loops (called "random coils"), which serve as transitions between more dilate localized secondary modules of helices or sheets. These random coils range generally from 2 to 16 residues, although they can be longer. Lastly, the modular maxima at the largest scales ($\geq 60$ dd) are relatively long hierarchical hydrophobic domains of 40 to 50 amino acids, or more.

The complex Morlet continuous wavelet transformation, W(a,b), of a protein's undecomposed $H_i$ is obtained by dilating (i/a) and translating (i/b) the analyzing wavelet, w. With b representing distance translated down the sequence and a the "scales" or "dilates" as sequential radian frequencies or wavenumbers of w, the "mother wavelet", wavelet transformations, $$W(a,b) = (1/\sqrt{a})\int_0^i H(i)w\left(\frac{i-b}{a}\right)di$$

may be useful in conserving both wavelengths and locations for structural prediction using $H_i$ in polypeptides and proteins. For w we chose a member of the family of continuous, symmetric, $\approx$zero mean, infinitely regular and differentiable, modulated Gaussian Morlet wavelets $$w(x) = \frac{1}{2\pi}\exp\left(\frac{-x^2}{2}\right)\exp(2\pi i f x).$$

Even though this and most of its other applications involve real numbered series, the Morlet continuous wavelet transformation W(a,b) is complex. As such, it has real (modulus) and imaginary (phase) parts. In categorizing proteins into structural families, the physicochemical features (i.e., hydrophobic free energies or other amino acid physical properties listed above) of the sequence locations, wavenumbers and hierarchically scaling transitions are of interest. Both the phase and modulus plots are suited to the detection and location of such features.

Intuitively, the usual three-dimensional wavelet space (not shown) exploits 64 dilate divisions, dd, related to mother wavelengths, $\bar{\omega}$, as a nonlinear function, $$\varpi = f(dd) = \frac{1}{0.5 - (dd)\left(\frac{0.5}{64}\right)}.$$

To prevent aliasing, the shortest $-=1/0.5=2$ amino acids, which is graphed at the bottom end of the y-axis, with $f(dd) \to 1/0 = \infty$ at the top end. The position on the x-axis indexes sequence location; the y-axis indicates the relative dilation of w(x) (composed with $H_i$) in dilate divisions. The modular amplitudes of the wavelet transformations may be graphed as gray-scale shaded, with relative maxima being lighter and relative minima being darker in shading. These absolute amplitudes within each of the 64 dilate ranges were normalized to 100% ("coloration by scale"). This choice of "by scale" versus "across scale" color coding of modular amplitudes does not portray the relative dominance of structures across all dilate ranges (which results in the loss of wavelet structural detail), but rather outlines the relative amplitudes of modular patterns and their locations at each dilate range. A variety of graphing techniques including color coding, gray scale, contour and other ways of indicating moduli and/or amplitudes may be employed, as determined by the particular global polypeptide property that is being addressed.

The wavelet transformation method transforms a one-dimensional $H_i$ series into a two-dimensional wavelet space, resulting in informational redundancy that is inherent in the wavelet transformation technique. Potentially artifactual autocorrelations due to the redundancies can be defined in terms of their average over the entire sequence of observables. It is known, for example, that continuous wavelet graphs of random series can manifest patches of correlated regions which decrease with increasing scale and have their origins in the wavelet of the transform itself. In light of this problem, the Morlet or other wavelength graphs of the eigenfunctions, as opposed to those of the undecomposed sequences, may be used to seek additional information in support of the origins in the data of the structural features of the wavelet graphs.

Wavelet transformations of the receptor and ligand eigenfunctions generate wavelet graphs, $W_R$ and $W^L$. Wavelet transformation, W(a,b) of the receptor eigenfunction $\Psi^R$ is accomplished by decomposing the eigenfunction $\Psi^R$ values into translated $W(n) \to W(n-b)$ and scaled $W(n) \to W(n/a)$ versions of the mother wavelet, w, a waveform having an average value of 0

$$\left(\int_{-\infty}^{\infty} w(n)\,dn = 0\right),$$

of finite length, arbitrary regularity and symmetry, and which is composed as $$W(a, b) = (1/\sqrt{a}) \int_0^i H(i) w\left(\frac{i-b}{a}\right) di,$$

as above for the undecomposed $H_i$. Similarly, wavelet transformation of the ligand eigenfunction $\Psi^L$ is accomplished in the same manner, by decomposing the $\Psi^L$ values into translated $W(n) \to W(n-b)$ and scaled $W(n) \to W(n/a)$ versions of the mother wavelet, w.

Because wavelet transforms preserve sequence position information of the statistical modes' occurrences, the results of any of the variety of wavelet transformations locate one or more subsequences of the polypeptide that can serve as amino acid distribution sources in the design of peptide or peptide-like molecules. The distribution of amino acids within these subsequences can be employed as a guide in the selection of particular amino acids within the physicochemical group of the peptide template, as further discussed below. Similarly, a symbolic or literal template can be created directly from the amino acid subsequences corresponding to the physicochemical subsequence or subsequences so selected or through the decomposition of single or multiple concatenated subsequences to create an eigenvector template.

While the peptides or peptide-like molecules produced by this method almost always share the maximum entropy power spectral modes of their eigenvector template, it is sometimes the case, particularly when the eigenvector template is multimodal, that a mode evident in the maximum entropy power spectrum and wavelet transformations of the eigenfunction or eigenfunctions of interest is not evident in the maximum entropy power spectral transformation of the associated eigenvector or eigenvectors, their template or the peptides produced from the template. Often the spectrally invisible mode has the longer wavelength of multiple modes, and when this is the case, the mode is often detectable as an amplitude-modulated wave in the eigenvector, its template or the peptides produced from the template. This may result from the short length of the eigenvector, its template and the peptides produced from the template and the statistical nature of the power spectral transformation. The eigenvector, its template and the peptides produced from the template are still considered to be mode-matched to the polypeptide, as they contain physicochemical amplitude variations on the mode of interest.

Wavelet Packet Transformations

Wavelet packet analysis may also be used in the identification, localization and characterization of physicochemical modes and mode relevant subsequences and the creation of wavelet subsequence templates. Wavelet packet analysis uses the same set of mother wavelets listed above, but generalizes the technique, allowing a range of representations of the decomposed sequence. In one-dimensional wavelet packet analysis, the physicochemical series, S, is decomposed into its gross and fine scale variation, then each of the resulting gross scale, G, (approximation) and fine scale, F, (detail) series are again decomposed into gross and fine scales. This process is repeated an arbitrary number of times, p, resulting in a binary tree of sequences with p levels as

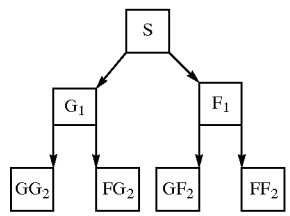

for p=2. The original physicochemical series can then be represented as an expansion of the wavelet packet atoms, each of which is a waveform, e.g., $S=G_1+GF_2+FF_2$. As p increases and trees get more complex, the number of such possible representations is obviously large. To select among these representations of the physicochemical series we employ one of two entropy threshold criteria: Shannon (i.e., $-\Sigma H_i^2 \log(H_i^2)$) and Stein's Unbiased Risk Estimate (SURE) (i.e.,. $\sqrt{2\log_e(n\log_2(n))}$, where n equals the number of points in the physicochemical series). With these criteria we produce "best level" and "best tree" representations, with which we can compare the physicochemical attributes of two or more physicochemical series.

Wavelet packets are relatively easy to compute when using orthogonal mother wavelets. Starting with two filters of length N corresponding to the wavelet, h(n) and g(n), the reversed version of the low-pass decomposition filter and the high-pass decomposition filter are divided by $\sqrt{2}$ respectively. Then we define the system of functions $W_n(x)$, (n=0,1,2 . . . ) as, $$W_{2n}(x) = 2\sum_{k=0}^{2N-1} h(k)W_n(2x-k) \text{ and}$$

$$W_{2n+1}(x) = 2\sum_{k=0}^{2N-1} g(k)W_n(2x-k)$$

where $W_0(x)$ is the scaling function and $W_1(x)$ is the wavelet function.

Starting from the functions $W_n(x)$, n∈N, we consider the family of analyzing functions $W_{j,n,k}(x)=2^{-j/2}W_n(2^{-j}x-k)$, where n∈N and j,k are nonnegative integers. j can be considered a scale parameter and k can be interpreted as the sequence localization parameter. $W_n(x)$ oscillates approximately n times. For fixed j and k, $W_{j,n,k}$ assesses fluctuations of the physicochemical sequence around the position $2^j \cdot k$ at the scale $2^{-j}$ across frequencies/wavenumbers for the accessible values of n. For some basis functions, the naturally n-ordered functions must be reordered so that the number of zero crossings of the wavelet increases monotonically with the order of the function.

The set of functions $W_{j,n,k}(x)$ is the (j,n) wavelet packet, which when j,n are positive integers and k has an integer value, are organized in tree structures. Each node of the tree is of the form

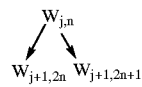

Because $\{(W_{j+1,2n}), (W_{j+1,2n+1})\}$ is an orthogonal basis of the space spanned by $W_{j,n}$, the leaves of every connected binary subtree of the wavelet packet tree correspond to an orthogonal basis of the initial space. For our physicochemical sequences, each wavelet packet basis will provide an exact reconstruction but with a specific spatial frequency subband coding. As a result, a physicochemical series of length $N=2^L$ can be expanded in at most $2^N$ ways with a binary tree of depth L.

As these can be unmanageably large numbers, we choose optimal representations through the application of the two entropy criteria listed above, i.e., Shannon and Stein's Unbiased Risk Estimate, although other criteria could be employed. Other entropy-based criteria usable in the wavelet packet transformations can include the logarithm of the "energies" entropy (i.e., $$\sum_i \log(H_i^2),$$

with the convention that log(0)=0), topological entropy estimate for a finite series (i.e., the asymptotic growth rate of the trace of the recursively exponentiated transfer matrix of each subband), and a fixed entropy threshold. Because they are well suited to quantifying additivity type properties, produce efficient searches in binary tree structures, and describe information carrying properties of the subbands, we favor entropy-based criteria.

In each case, we compute the entropy of the original physicochemical series, then we split the series using the chosen wavelet and recompute the entropy of each resulting piece. If the sum of the entropies of the pieces at a given level is less than the sum of the entropies of the preceding level, the split is considered to be informative. By this method, applied exhaustively to all possible additive representations, entropy-minimizing best level and best tree representations can be defined. These graphs are frequency-ordered (i.e., subband graphs are arranged from those representing lowest to those representing highest frequencies) so as to be maximally interpretable. A variety of graphing techniques, including "by scale" and "across scale" color coding, gray scale, contour and other ways of indicating coefficient values may be employed.

Intersection of Two or More Wavelet Coefficient Arrays

The intersection of two or more wavelet coefficient arrays may also be used in the identification, localization and characterization of physicochemical modes and mode relevant subsequences and the creation of wavelet subsequence templates. Various wavelet techniques are differentially suited to the assessment of specific aspects of the physicochemical protein, polypeptide and peptide or peptide-like molecule series. For example, as noted above, in discrete or continuous wavelet analysis, Haar mother wavelets are particularly suited to localizing coefficients in sequence space, while Meyer, Morlet and Mexican Hat mother wavelets are better suited to dilate space localization. To derive more information in a single representation, and if the matrices of coefficients are of the same order and derived from analyses of the same physicochemical series, we generally apply highpass filters to each wavelet coefficient matrix and then compute their cell-wise intersection. A nonzero cell, $A_{i,j}$, in each and all constituent matrices results in a nonzero corresponding cell in the intersection matrix, $B_{i,j}$, that takes a value equal to the average or median of the values of the corresponding cells in the constituent matrices. Constituent wavelet coefficient arrays can result from the use of discrete or continuous wavelet transforms or wavelet packet analysis, and from any of the above listed mother wavelets, provided the above conditions are met. The intersection matrix serves to evaluate the wavelength and dominant position or positions of physicochemical modes, and also as a method by which to identify one or more amino acid subsequences in the analyzed polypeptide or peptide that are associated with mode-relevant binding and/or modulation. The subsequence or subsequences so identified may be employed individually or together as a source for amino acid probabilities in the creation of peptides or peptide-like molecules. The amino acid or corresponding physicochemical subsequence or subsequences may be used directly or in a coded form as a template for the design of peptides or peptide-like molecules that will bind the polypeptide or peptide on which the analysis was based.

Construction of Peptides by Assignment of Amino Acids to an Eigenvector Template The sequential eigenstructures of the transformations described above may be used to design de novo new peptides that may bind to and/or otherwise modulate and have an influence on various protein or polypeptide activities. To construct new peptide ligands, the sequential $H_i$ (or other physicochemical properties, as above) values of the receptor are normalized and partitioned. Amino acid assignment is dictated by the mode-relevant eigenvector or eigenvector-based template, and is consistent with membership in one of the natural divisions dictated by the physicochemical property, e.g. the four natural divisions of the naturally-occurring amino acid's $\Delta G_{hp}$ values. Furthermore, amino acid assignment may be weighted by any desired means known to those in the art,.such as by the amino acid distribution found in a particular amino acid pool or by accounting for known effects of directed mutations or segment replacements.

Peptide construction from the distinct spectral signature eigenvector-based template begins with the selection of the appropriate eigenvector (or eigenvectors), based on their eigenvalues and the maximum entropy power spectral mode or modes of the associated eigenfunction or eigenfunctions to be represented in the eigenvector template, $X_{temp}$. The y-axis of the graph of $X_{temp}$ is divided into a number of segments, corresponding to the range of $\Delta G_{hp}$ values of each of the various groups of the twenty essential amino acids listed above in Table 1 or Table 2. The index of the eigenvector (graphed on the x-axis of $X_{temp}$) may be any value between 1 and M, and is chosen based on the relevant eigenfunctions that the all poles power spectrum and/or the wavelet transformation have shown contain the receptor's ligand-matching signatory mode or modes. For example, in the cases of the seven-transmembrane receptor superfamily members, the first eigenfunction (i=1) resembles the moving average hydropathy plot, and it is the second (and sometimes additionally a higher eigenfunction) that provides the distinct spectral signature of the protein that may act as the template for the construction of the mode-matched peptide. In the cases of the single transmembrane tyrosine kinase-coupled receptors, and other receptors with a single transmembrane sequence (and other protein families listed above), as well as other proteins, such as transporters, enzymes and chaperones, the first eigenfunction (and again, sometimes additionally a higher eigenfunction) may contain useful spectral signatures. The ordered eigenvalue spectra generally decay quickly after the first few leading ordered values, such that most if not all of the transmembrane and peptide binding/modulating mode or modes information is captured in the first few eigenvalues, i.e., $\{v_j\}_{i=1...4}$, though 8<M<25 may be employ for adequate separation and resolution.

With respect to the substitution process in the M-length eigenvector template $X_{temp}$ associated with the eigenfunction or eigenfunctions of interest, the sequence of values in the x(vector position)–y(vector position) of $X_{temp}$ are plotted, followed by partitioning of the occupied region of they axis into the desired number of parts. While the hydrophobic values of the twenty naturally-occurring amino acids naturally partition into four equal parts (Table 1 and Table 2), the hydrophobic values may also be partitioned into a lesser or greater number of parts, and the partitions may or may not be equal. Furthermore, when other physicochemical properties are used, another number of partitions may be desirable. In the case of hydrophobic free energies, the top region of the partitioned eigenvector template graph is mapped to the highest hydrophobicity (i.e., Group I) amino acids, the next region to the second highest hydrophobicity amino acids (i.e., Group II), etc. down to the lowest hydrophobicity amino acids in the lowest region. Starting at the first of the M points of $X_{temp}$, the amino acid hydrophobicity group to which this point belongs is determined. Then, a member of the amino acids in this group (from the chosen amino acid pool) is randomly assigned to this point. The process then is repeated for the remainder of the points in the eigenvector template to generate an M-length peptide which is considered mode-matched to the receptor. The process may be repeated as often as desired to generate a large number of eigenvector template-defined candidate peptides.

Multiple eigenvectors derived from the same receptor (e.g., $X_1$ and $X_2$), each with distinct spectral properties in the associated eigenfunctions may also be used in combination to generate candidate peptides. In such a case, it is important to preserve multiple aspects of the receptor's eigenfunction mode signature. Accordingly, an eigenivector template vector $\Omega$ of length M is formed. Vector $\Omega$ is the eigenvalue ($\nu$)-weighted sum of the eigenvectors (X) from which the eigenfunctions are derived. That is, $\Omega(j)=\nu_1X_1+\nu_2X_2$. This is possible due to the linear additivity of eigenvectors and their eigenvalue weights. The candidate peptides then are generated as described above, using $\Omega(j)$ in place of the single eigenvector in the assignment of the amino acids from the four amino acid groups. It will be obvious to those of skill in the art that other transformations and composites of multiple eigenvectors can be employed to form M-length eigenvector templates derived from two or more eigenvectors, as desired.

Construction of Peptides by Assignment of Amino Acids Based on Mode-matching to Wavelet Identified Polypeptide Subsequences Like the sequential eigenstructures described above, the results of the variety of wavelet transformations described above may be used to design de novo peptides that may bind to and/or otherwise modulate and have an influence on various protein or polypeptide activities. The wavelet-derived subsequence template, $S_{temp}$, is produced by first performing discrete or continuous wavelet transformations, wavelet packet transformations or multiple convolved wavelet transformations on a polypeptide physicochemical series and on the physicochemical series of a peptide or peptide-like molecule known or suspected to bind the polypeptide. Modes of physicochemical fluctuation are assessed to identify the mode or modes of interest, generally as a mode or modes shared by the polypeptide and the peptide under consideration. Once this mode or modes is identified, it can be localized in the sequence of the polypeptide by selecting an interval around wavelet coefficient peaks in the dilate subband or subbands that correspond to that wavelength. These sequence intervals are then used to select the corresponding sequences of amino acids in the primary polypeptide series. Amino acid subsequences are then coded into group membership on the basis of a physicochemical property and its grouping scheme, and this coded sequence acts as a template for the de novo generation of new peptides, as above.

To construct new peptides, the sequential physicochemical values of the polypeptide or protein and peptides known to bind it, if such exist, are normalized and partitioned. Shared physicochemical mode or modes or mode(s) of interest are identified in the wavelet graphs. The sequence interval at which a mode is dominant in the polypeptide is identified and this subsequence of 100 amino acids or less in length forms a template. Amino acid assignment is dictated by the mode-relevant subsequence-based template, and is consistent with membership in one of the natural divisions dictated by the physicochemical property, e.g. the four natural divisions of amino acid $\Delta G_{hp}$. Furthermore, amino acid assignment may be weighted by any desired means known to those in the art, such as by the amino acid distribution found in a particular amino acid pool, or by accounting for known effects of directed mutations or segment replacements, as described below.

The subsequence-based template, $S_{temp}$, is graphed so that the y-axis of the graph of $S_{temp}$ is divided into a number of segments corresponding to the group memberships of the essential amino acids, listed above in Table 1 or Table 2. The chosen polypeptide amino acid subsequence may be any contiguous interval of 100 amino acids or less in length, and is chosen based on the colocalization in the dilate space shown contain the receptor's ligand-matching signatory mode or modes and the sequence space corresponding to the chosen interval.

With respect to the substitution process in the subsequence template $S_{temp}$ associated with the subsequence or subsequences of interest, the sequence of values in the x(vector position)–y(physicochemical group membership) of $S_{temp}$ are plotted. While the hydrophobic values of the twenty naturally-occurring amino acids naturally partition into four equal parts (Table 1 and Table 2), the physicochemical values associated with the amino acids may also be partitioned into a lesser or greater number of parts, and the partitions may or may not be equal. Furthermore, another number of partitions may be desirable. In the case of hydrophobic free energies, the top region of the partitioned template graph is mapped to the highest hydrophobicity (i.e., Group I) amino acids, the next region to the second highest hydrophobicity amino acids (i.e., Group II), etc. down to the lowest hydrophobicity amino acids in the lowest region. Starting at the first point of $S_{temp}$, the physicochemical value of this point is related to the appropriate hydrophobicity group. Then, a member of the amino acids in this group (from the chosen amino acid pool) is randomly assigned to this point. The process then is repeated for the remainder of the points in the template to generate a peptide which is considered mode-matched to the receptor. The process may be repeated as often as desired to generate a large number of subsequence template-defined candidate peptides.

Construction of Peptides by Assignment of Amino Acids Based on Redundant Polypeptide Amino Acid Subsequences An alternative template based on symbolic dynamics may also be used to design de novo peptides that may bind to and/or otherwise modulate and have an influence on various protein or polypeptide activities. A redundant subsequence template, $R_{temp}$, results from the evaluation of the symbolically-coded amino acid sequence of a target polypeptide and/or protein. The polypeptide amino acid sequence of length N is either retained as a string vector of amino acid one-letter representations or is transformed into a symbol sequence by replacing each amino acid with a value representing its group membership associated with a physicochemical property and a grouping scheme. In either case, the N length sequence, $D_{i,i=1,2, \ldots N,}$ is treated as a string vector and examined for redundant substrings.

Starting at the first points of the sequence, a search is made for the largest possible repeated substring, of length N/2, that is, points D[1,2, . . . N/2]. Next the search sequence size is reduced by 1, and starting again at the first point, the first N/2−1 characters are assigned as a search string and all identical non-overlapping substrings are identified as the algorithm looks down the entire N length series. When this search is complete, the search string is reassigned as points corresponding to points D[2,3 . . . , N/2] and all non-overlapping substrings identical to the search string are identified as the algorithm looks down the entire N length series from $D_{N/2+1}$ to $D_N$. When this search is complete, the search string is reassigned as points corresponding to points D[3,4 . . . , N/2+1], and soon. When all possible non-overlapping redundant substrings of a given length have been identified, the search string length is reduced by one and the search is resumed. This recursive search terminates when the search string is only one character long. Redundant substrings of three or more characters must be repeated at least twice to be considered, while substrings of two characters must be repeated at least three times.

All non-overlapping substrings (i.e., those with at least two distinct occurrences in $D_i$) are saved and displayed with their corresponding frequencies of occurrence and starting positions in the $D_i$. $R_{temp}$ may be composed of a single or multiple redundant substrings so identified. When multiple substrings, or redundant substrings, are employed the multiple substrings are concatenated to form $R_{temp}$. Preference is generally given to long subsequences in the creation of $R_{temp}$. However, the choice of redundant substring or substrings represented in the $R_{temp}$ may be modified by knowledge of the results of studies of point mutations and/or peptide segment exchanges that affect binding/and or activity of ligands for the receptor, and/or specific subsequence physicochemical attributes from the literature.

With respect to the substitution process in the redundant subsequence template $R_{temp}$ associated with the subsequence or subsequences of interest, the sequence of values in the x(vector position)–y(physicochemical group membership) are plotted. While the hydrophobic values of the twenty naturally-occurring amino acids naturally partition into four equal parts (Table 1 and Table 2), these or other physicochemical values associated with the amino acids may also be partitioned into a lesser or greater number of parts, and the partitions may or may not be equal. Furthermore, another number of partitions may be desirable. In the case of hydrophobic free energies, the top region of the partitioned template graph is mapped to the highest hydrophobicity (i.e., Group I) amino acids, the next region to the second highest hydrophobicity amino acids (i.e., Group II), etc. down to the lowest hydrophobicity amino acids in the lowest region. Starting at the first point of $R_{temp}$, the physicochemical value of this point is related to the appropriate hydrophobicity group. Then, a member of the amino acids in this group (from the chosen amino acid pool)

is randomly assigned to this point. The process then is repeated for the remainder of the points in the template to generate a peptide which is considered mode or modes-matched to the receptor. The process may be repeated as often as desired to generate a large number of subsequence template-defined candidate peptides.

As an example of redundant substring template generation, consider the following short amino acid sequence retained as a string vector of amino acid one letter representations:

AIRCKSMLRYGHAMQLREWVCCMHAMQVYRLM (SEQ ID NO:94)

If we chose to apply the template-generating algorithm directly to this series, the search algorithm would begin by looking for two copies of the first half of the series, AIRCKSMLRYGHAMQL (SEQ ID NO:95). Next it would assess the starting positions and frequency of occurrence of the substring from which the last amino acid, L has been dropped, i.e., AIRCKSMLRYGHAMQ (SEQ ID NO: 96), and so on, looking at each possible substring in the first half of the sequence. The algorithm finds one redundant substring, HAMQ, occurring twice starting at positions 12 and 24. A generalization of this method also allows for the search of substrings that are both "backward" and "forward" in orientation in the original sequence. Such a search of our example string also turns up the twice repeated substring MLRY, appearing at starting position 7 in a "forward" orientation and at starting position 29 in a "backward" orientation. Our $R_{temp}$ might then equal one or both of these specific amino acid substrings in some order and orientation.

Transforming the amino acid sequence into a symbolic vector in which each point represents the hydrophobic free energy group membership of the corresponding amino acid sequence, we get: 3132242231433242331222232421322. A search of this string for redundant substrings yields: 33242 (which appears twice starting at positions 12 and 24), 1322 (which appears twice at starting positions 2 and 29, and corresponds to the MLRY sequence described above) and 22 (appearing three times that do not overlap the longer coded subsequences at positions 7, 20 and 22). Our $R_{temp}$ might then include one or any combination of these substrings representing hydrophobic free energy groups. Examples of appropriate sample subsequence templates might then include 33242221322, 13222233242, and 2233242221322, among others.

Reduction of the Number of Potential Mode-matched Peptide Candidates

The large number of potential candidate peptides generated in this fashion can be reduced in a number of ways. First, all poles power spectral analyses or wavelet transformations of the peptides may be performed to determine those peptides having the best mode-match to the receptor. In addition, the probability of occurrence of the amino acid members of each of the four $\Delta G_{hp}$ groups in the general amino acid pools available to the particular organ or organism may be determined, and the assignment of the amino acids may be weighted accordingly. Finally, the results of studies of point mutations and/or peptide segment exchanges that affect binding and/or activity of ligands for the receptor from the literature may lead to empirical attempts to optimize the sequences of the candidate peptides. The distributions of amino acids from which random selection by partition memberships may be made include the amino acid compositions of relevant proteins, free amino acid pools from brain, liver and/or other organs, bound and/or free amino acids in plasma and/or spinal fluid, extracellular, intracellular and/or other free amino acid pools, or may be derived from a subsequence or subsequences of amino acids located through the application of wavelet transformations or through the calculation of redundant substrings of amino acids. Furthermore, any combination of these procedures may be employed to optimize the sequences of the candidate peptides and reduce the probability of generating nonfunctional peptide ligands.

In addition to the use of the twenty naturally occurring amino acids, other potential peptide or peptide analogue molecule elements may be used that can be put in relationship to the sequence patterns of physical properties determined using the methods indicated. For example, D-amino acids or modified and/or pseudo amino acids (e.g., amino acids bearing acetyl, glycosyl, thiol, chorine, flourine, bromine, alkoxyl, amino alkyl, or sulfoximine groups, further including those that are alkylated, acylated, methylated and further including those pseudoamino acids that are polycarbonate, polyesters, phosphinic, cyclic and others with peptide bonds replaced by a variety of other linkages) may be included in the pool of components used to generate the candidate peptides. Furthermore, other, non-naturally occurring amino acids, dipeptides, tripeptides, and the like may be used, as well as non-amino acid compounds. Examples of the non-naturally occurring amino acids include, for example, anserine, citrulline, cystathionine, homocysteine, δ-hydroxylysine, hydroxyproline, methylhistidine, norleucine, ornithine, phosphoserine, sarcosine, taurine, hypotaurine and other rare amino acids. In addition, compounds that involve non-peptide bonds between the constituents may be employed if they produce a desirable result, such as increased stability, resistance to proteolysis, or increased binding, modulation, activation and/or inhibition of the target polypeptide. The only requirements for use of these amino acids and non-amino acid components in a manner similar to that of the twenty naturally occurring amino acids in the methods of the present invention are that, first, incorporation of the modified amino acids and/or components into a linear amino acid chain must be possible, and second, that the values for the free energy of transfer of the components (or other of the above listed and possible ordered physical properties) must be computable, have quantitatively orderable properties relative to one another and be consonant with their assignment as dictated by the sequential pattern descriptors such as eigenvector weighting partitions such that the component may be assigned to its proper physicochemical group.

The present invention is illustrated in terms of the following examples, which are intended to be descriptive only and is not intended to limit the invention in any way.

EXAMPLE 1

The 443-amino acid long isoform of the human dopamine $D_2$ ($D_2DA$) receptor was transformed into a real numbered $\Delta G_{hp}$ series, $H_i$, using the Eyring-Tanford hydrophobicity scale. This $H_i$ series (and its all poles maximum entropy power spectral transformation, $S(\omega)$, see below) demonstrated a multimodal distribution (FIG. 2A). In place of the a priori selection of orthonormal transformations such as Fourier or Bessel functions with which to decompose the receptor's $H_i$, i=1 . . . 443, orthogonal functions were generated from the receptor's $H_i$ directly using the Broomhead-King ("B-K") dccomposition derivative of methods often named after Karhuenen and Loeve ("K-L"). A K-L decomposition of the $H_i$ series of the $D_2DA$ receptor involves the autocorrelation matrix, $A_{ij}$, of the entire $H_i$, i=1 . . . 443 series, yielding an eigenvector template for $D_2DA$ targeted peptides as long as the receptor itself. In the B-K procedure, the $H_i$ sequences were used to generate an empirically chosen M-lagged data matrix, from which M×M covariance matrices, $C_M$, were computed and decomposed into sets of 1 orthogonal eigenfunctions, $\Psi_l(j)$, where l=1 ... M, j=1 ... M. As seen below, this linear decomposition yielded eigenvector templates for amino acid assignment of length M.

Figure 2:
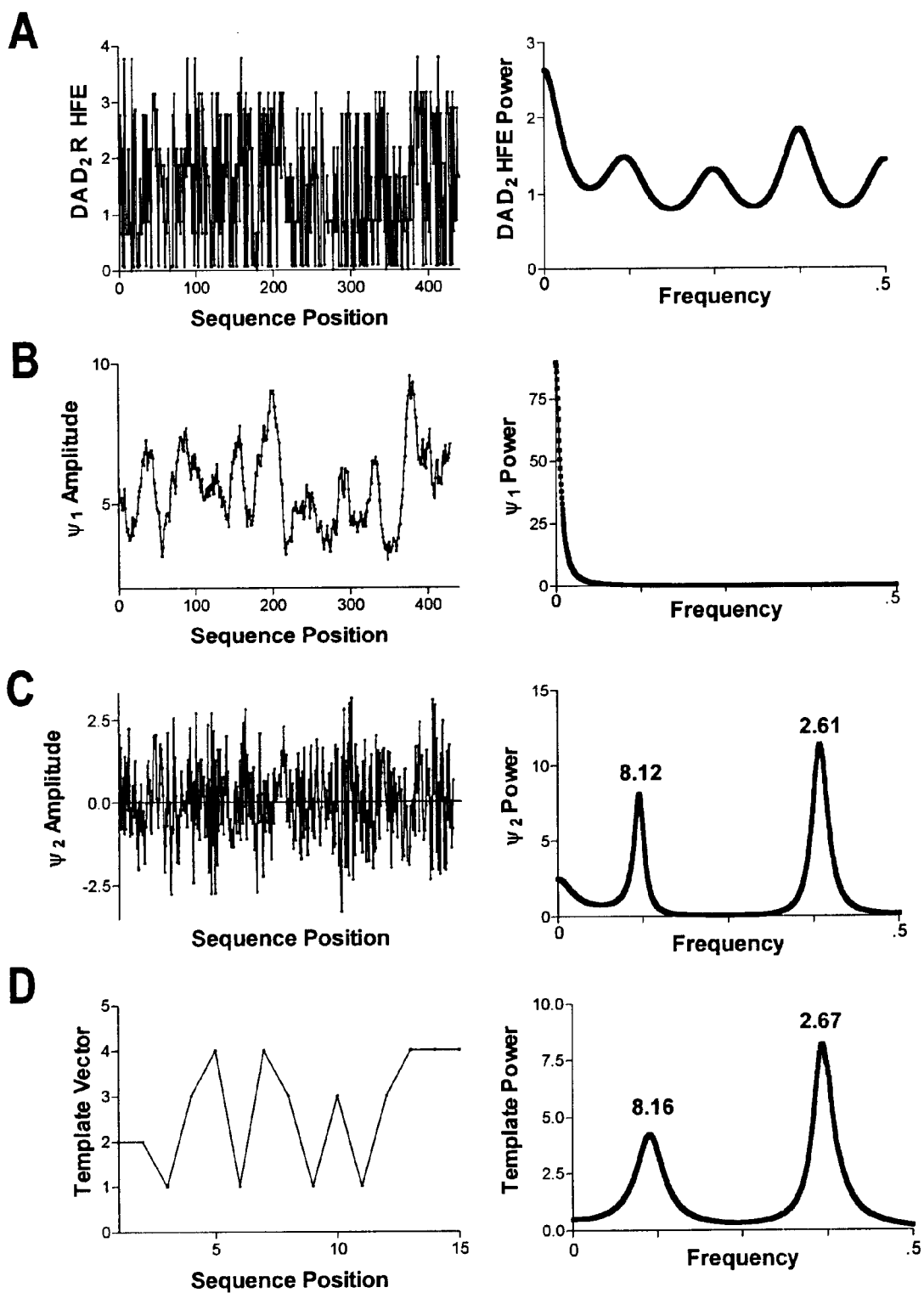
FIG. 2A (left) is a graph of the hydrophobic free energy series, $H_i$, of the human $D_2DA$ receptor and (right) its broad band, multimodal all poles, maximum entropy power spectral transformation $S(\omega)$.
FIG. 2B (left) is a graph of the human $D_2DA$ receptor's dominant eigenfunction, $\Psi_1$, demonstrating the ≈7 peaks characteristic of the leading receptor eigenfunction of members of the seven-transmembrane receptor superfamily and (right) the associated long wavelength peak (>50 residues) in the $S(\omega)$.
FIG. 2C (left) is a graph of the human $D_2DA$ receptor's secondary eigenfunction, $\Psi_2$, and (right) its associated peaks in the $S(\omega)$ at wavelengths of 8.12 and 2.61 residues.
FIG. 2D (left) is a graph of the human $D_2DA$ receptor's secondary eigenvector, $X_2$, used in the design of new peptides, and (right) its associated peaks in the $S(\omega)$ at wavelengths of 8.16 and 2.67 residues.

From the lagged data vectors, and where k=N−M+1, the sequence-averaged dyadic product, $\{H_iH_i^T\}$, was used to obtain the autocovariance matrix, a M×M matrix, $C_M=1/k\{H_iH_i^T\}$, using M=15. We computed the ordered eigenvalues, $\{v_i\}_{i=1,\ldots M}$ and the associated eigenvectors, $X_i(j)$, of $C_M$, where i=1 ... M and labels the eigenvector, and j=1 ... M refers to the jth component of the eigenvector $X_i$. The eigenvalues, $\{v_i\}_{i=1\ldots M}$, were ordered from largest to smallest and constituted the eigenvalue spectrum of $C_M$. The similarly ordered and associated eigenvectors, $X_i(j)$, were convolved with $H_1, H_2, \ldots, H_N$ generating 105 $_l(j)$ where l=1 ... M labels the eigenvector and the j=1 ... N−M+1 (or j=1 ... N using the alternate computational form of $\Psi_l(j)$ indexed the eigenfunction's jth component. The convolution of each of the leading eigenvectors with the $H_i$ series was performed by computing the sums of the scalar products of the M-length eigenvector with an M-length of the $H_i$ series to produce a point in the eigenfunction. Similarly, we can sum the scalar products of the eigenvector and a point in the $H_i$ series, giving our alternate computation. Either process was translated down the $H_i$ series by one step and repeated to generate each of the sequential points of the eigenfunction that corresponds to its ordered eigenvalue-associated eigenvector in the computation. We have found that when M≈15, the least squares error was minimized in a fit of the leading eigenfunction, $\Psi_1$, dominated by the $D_2DA$ receptor's hydrophobic TMs, to the n-block averaged pattern of hydrophobic variation, usually called the hydropathy plot. This leading eigenfunction demonstrated approximately seven transmembrane segments, and its all poles maximum entropy power spectral transformation (S(ω)) demonstrated an average amino acid wavelength peak of >50 amino acids (FIG. 2B). A data matrix of M≈15 also contained sufficient information such that the secondary $D_2DA$ receptor eigenfunction, $\Psi_2$, could be determined to exhibit two putative receptor $\Delta G_{hp}$ binding/modulating mode or modes of 8.12 and 2.61 amino acids, as seen in its S(ω) (FIG. 2C). The eigenvector associated with the secondary eigenfunction, $X_2$, demonstrated all poles, maximum entropy power spectra, S(ω), with putative $D_2DA$ receptor $\Delta G_{hp}$ binding/modulating modes of 8.16 and 2.67 amino acids, as seen in its S(ω) (FIG. 1D). These binding/modulating modes were closely matched with the modes of the $D_2DA$ receptor native peptide ligands, such as neurotensin, which has an S(ω) peak of 8.13 amino acids. M=15 is within the middle of the ≈5–30 amino acid length range of most physiologically active peptides. Most peptides with the capacity to bind antibodies and elicit an antibody response are also in the range of about 5–30 amino acids in length.

Figure 3:
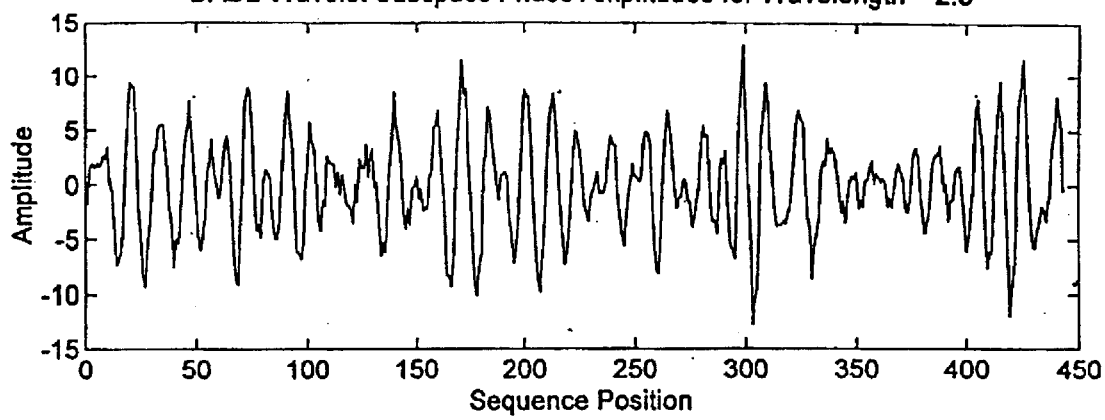
FIG. 3A is a graph of the wavelet subspace transformation of the $H_i$ of the $D_2DA$ receptor, wherein $\bar{\omega}=f(dd) \cong 2.3$ residues. Sequence position is graphed along the x-axis and phase amplitude along the y-axis.
FIG. 3B is a graph of the wavelet subspace transformation of the $H_i$ of the $D_2DA$ receptor, wherein $\bar{\omega}=f(dd) \cong 8.1$ residues. Sequence position is graphed along the x-axis and phase amplitude along the y-axis.
Figure 3:
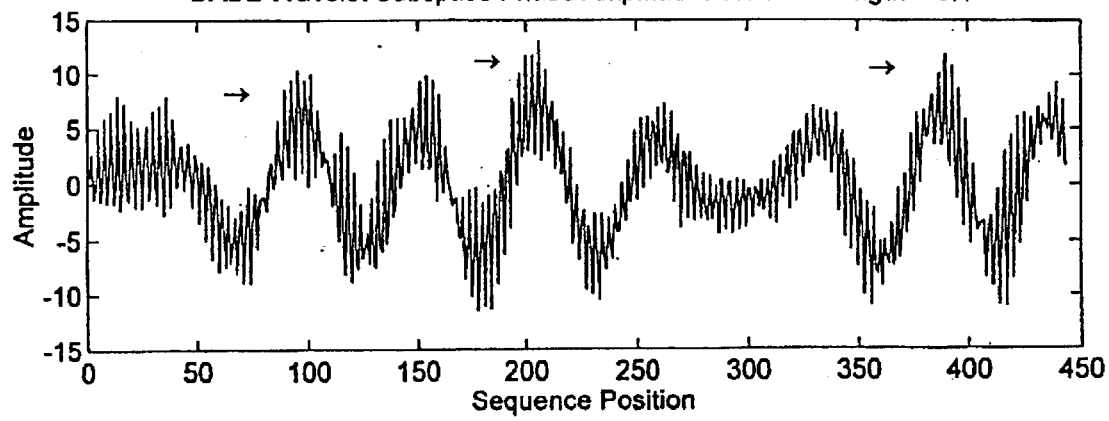
Figure 4:
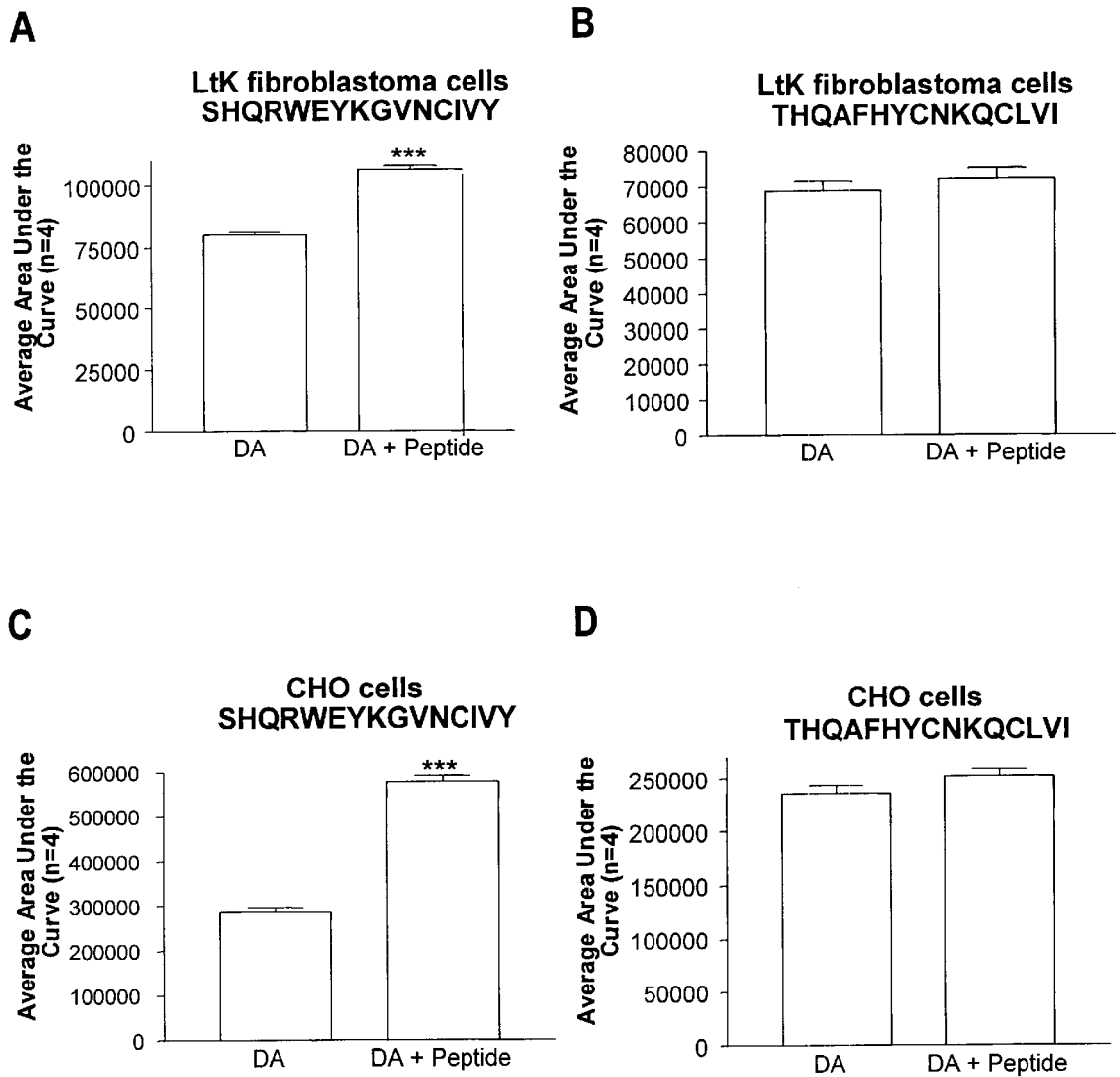
FIG. 4A is a graph showing the effects of the SHQR peptide (SEQ ID NO:1) on the EAR responses of the human $D_2DA$-transfected mouse LtK cell system to dopamine infusion. DA=control with dopamine alone.
FIG. 4B is a graph showing the effects of the THQA (SEQ ID NO:2) peptide on the EAR responses of the human $D_2DA$-transfected mouse LtK cell system to dopamine infusion. DA=control with dopamine alone.
FIG. 4C is a graph showing the effects of the SHQR (SEQ ID NO:1) peptide on the EAR responses of the human $D_2DA$-transfected mouse CHO cell system to dopamine infusion. DA=control with dopamine alone.
FIG. 4D is a graph showing the effects of the THQA (SEQ ID NO:2) peptide on the EAR responses of the human $D_2DA$-transfected mouse CHO-cell system to dopamine infusion. DA=control with dopamine alone.
Figure 5:
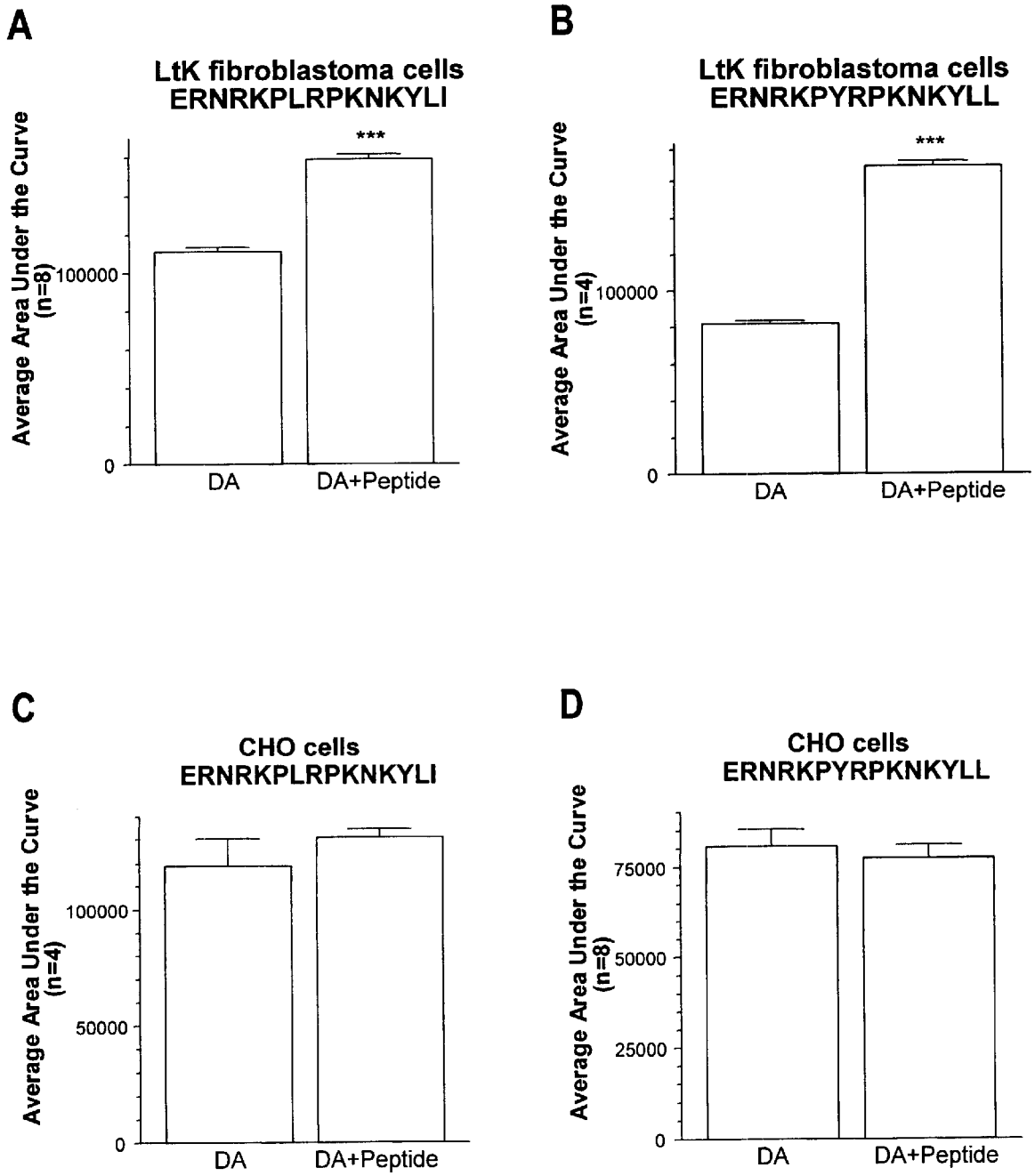
FIG. 5A is a graph showing the effects of the E . . . PL (SEQ ID NO:3) peptide on the EAR responses of the human $D_2DA$-transfected mouse LtK cell system to dopamine infusion. DA=control with dopamine alone.
FIG. 5B is a graph showing the effects of the E . . . PY (SEQ ID NO:4) peptide on the EAR responses of the human $D_2DA$-transfected mouse LtK cell system to dopamine infusion. DA=control with dopamine alone.
FIG. 5C is a graph showing the effects of the E . . . PL (SEQ ID NO:3) peptide on the EAR responses of the human $D_2DA$-transfected mouse CHO cell system to dopamine infusion. DA=control with dopamine alone.
FIG. 5D is a graph showing the effects of the E . . . PY peptide (SEQ ID NO:4) on the EAR responses of the human $D_2DA$-transfected mouse CHO cell system to dopamine infusion. DA=control with dopamine alone.

FIGS. 3A and 3B are two-dimensional graphical representations of the Morlet wavelet W(a,b) transformation of the $H_i$ of the $D_2DA$ receptor. In these graphs, sequence position is graphed along the x-axis, phase amplitudes along the y-axis and $\bar{\omega}=f(dd)$ is fixed at the two characteristic peaks (hydrophobic free energy binding/modulating mode or modes) of the S(ω) transformation of $\Psi_2$, as well as at the highest phase amplitudes of the W(a,b) transformations of the $H_i$ of the $D_2DA$ receptor, at $\bar{\omega}$, ω≈2.3 and 8.1 amino acid residues. FIGS. 2A and 2B demonstrate that although both the 2.3 amino acid and the 8.1 amino acid wavelengths of the $D_2DA$ receptor have phase amplitude peaks that are distributed throughout the $H_i$ length of $D_2DA$, the most prominent of the 8.1 amino acid phase amplitude sequence locations (marked by arrows) correspond to the extracellular loops EL-I, between $TM_2$ and $TM_3$ (residues 85–105); EL-II, between $TM_4$ and $TM_5$ ((≈residues 190–210); and EL-III, between $TM_6$ and $TM_7$ (≈residues 390–410). The brain peptide neurotensin is believed to mediate its actions through the $D_2DA$ receptor, and neurotensin exhibits an S(ω) peak of $\omega^{-1}$≈8.13 amino acids, which matches well with that of the $D_2DA$ receptor.

Peptide construction from the eigenvector template derived from the $D_2DA$ receptor was performed with the y-axis of $X_2$ as graphed in FIG. 2D (left) being divided into four equal segments corresponding to the natural 4-partition of the $\Delta G_{hp}$ values of the twenty naturally occurring essential amino acids listed above in Tables 1 and 2. Probability weightings for amino acid members of each of the four $\Delta G_{hp}$ groups were assigned on the basis of their relative occurrences in human cerebrospinal fluid (CSF), reflecting the brain's amino acid pool available for peptide synthesis. In addition, probability weightings were assigned on the basis of the amino acid distribution in each of the four groups of neurotensin, which we have shown previously to modulate the kinetics of binding by the human $D_2DA$ receptor. Based on these distributions, weighted random assignment of amino acids to each of the 15 points of the 4-equipartitioned $X_2$ generated the new peptides. The first two peptides were derived from the CSF pool probabilities, SHQRWEYKGVNCIVY ("SHQR"; SEQ ID NO:1) and THQAFHYCNKQCLVI ("THQA"; SEQ ID NO:2) (Table 3), and were synthesized to ≧95% purity (as determined by HPLC and mass spectrometry) by Multiple Peptide Systems (La Jolla, Calif.). Two additional peptides using an idealized $X_2$ and with probability weightings derived from the amino acid composition of neurotensin rather than human CSF, ERNRKPLRPKNKYLI ("E . . . PL"; SEQ ID NO:3) and ERNRKPYRPKNKYLL ("E . . . PY"; SEQ ID NO:4) (Table 3), were also designed and synthesized for microphysiometric testing. The last eight $D_2DA$ targeted algorithmically-derived peptides were produced using the $X_2$ eigenvector of the M=15 covariance matrix, $C_M$, of the human, long isoform, $D_2DA$ receptor as the template for amino acid assignment.

As an example of one of many possible physiological assays that may be used to evaluate the actions and potencies of designed peptides, two independently derived cell systems were examined with respect to the peptide action and/or modulation of their external acidification rate ("EAR") to dopamine. The mouse LtK fibroblastoma cell system was generously provided by Frederick Monsma (Hoffman-LaRoche, Basil, Switzerland). The CHO (Chinese hamster ovary) cell system was generously provided by Richard Mailman (Univ. of North Carolina, Chapel Hill, N.C.). Both cell systems were stably transfected with human long isoform $D_2DA$ receptor cDNA, which had been isolated from a human striatal cDNA library, sequenced and subcloned into the expression vector pRC/RSV (Invitrogen). The transformed Ltk system was characterized by lower baseline responsivity to its native agonist, dopamine, as measured in total milli-pH units (mpH). In contrast, the transformed CHO system manifested a higher baseline responsiveness to dopamine. Both systems were grown to confluence in DMEM containing 10% FBS. The cells were serum-starved 18–24 hours prior to use, and then assayed for EAR using a microphysiometer (Cytosensor; Molecular Devices, Sunnyvale, Calif.) in low buffering DMEM with 0.1% culture grade BSA.

The determination of EAR by microphysiometry involves a proton-sensitive silicon semiconductor photocurrent-driven sensor which measures changes in EAR resulting from effector-evoked alterations in cellular glycolytic and respiratory energy metabolism and/or alterations in sodium-hydrogen exchanges across cellular membranes. Protonic $H^+$, generated by such energy metabolism or exchanges, neutralizes the charge on the surface of the semiconductor, reducing the photocurrent produced at a rate linearly related to $H^+$ production.

The microphysiometer monitors pH in flow-through chambers containing the receptor-transfected cells. Generally, if the cells lines used are adherent cell lines, the cells are seeded into "capsule cups". If the cell lines are non-adherent cell lines, then the cells are immobilized in a fibrin matrix. For all microphysiometer runs, modified low buffering DMEM containing 0.1% BSA is pumped across the cells at a rate of approximately 100 $\mu$l/min, during which time the pH of the microenvironment surrounding the sensor surface is maintained at a relatively constant value. The measurement of the acid output rate of the cells, termed the acidification rate, is made when the fluid flow is periodically halted to allow buildup of acidic metabolites in the chamber, resulting in an alteration in the pH of the fluid. The pH is measured in millivolts, and converted to milli-pH units. The changes in pH are expressed as changes in milli-pH units per minute following the linear, time-dependent buildup of $H^+$ during intermittent periods of pump arrest followed by washout: Integration of the EARs over the time of action of dopamine yields an estimate of the total milli-pH units (measured as the area under the curve by trapezoidal approximation) generated during the action of the natural ligand alone, compared with that of the ligand when preceded by the infusion of the algorithmic peptide. This data is plotted as average sensitivity in the range of 0.001 pH units, and changes as little as 2% of the control are reproducibly detectable. Ligand induced, receptor-mediated increases in cell metabolic and $Na^+$-$H^+$ membrane regulatory activity is seen as an increase in the acidification rate.

Dopamine was infused at concentrations approximating its $EC_{50}$ in this system, that is, $\approx$1 $\mu$M. Following pilot studies which indicated a consistency in sensitivity and direction of effect, the twelve peptides were surveyed at 1 $\mu$M concentrations. Small Kolmogorov-Smirnov distances supported the assumption of normality in all of the data sets, so within chamber-paired, one-tailed t-tests with a significance criterion of p=0.05 were used.

FIGS. 4A–4D summarize the EAR responses to dopamine infusion with respect to the influence of SHQR (SEQ ID NO:1) and THQA (SEQ ID NO:2) in the two $D_2DA$ receptor-transfected cell systems, in which the former significantly potentiated the dopamine-induced increment in total milli-pH units in both cell systems. We report the results of one-tailed t-tests with pairing within chamber as $t_{(\#)}$, where # represents the degrees of freedom of the paired comparison and $\rho$ denotes the probability of such results occurring by chance. For the SHQR peptide (SEQ ID NO:1) in the LtK system, $t_{(3)}$=13.28, $\rho$=0.0009, and for the SHQR peptide (SEQ ID NO:1) in the CHO cell system, $t_{(3)}$=28.06, $\rho$<0.0001. THQA (SEQ ID NO:2) did not significantly potentiate the dopamine response in either system, $t_{(3)}$= 0.620 and $t_{(3)}$=1.309, $\rho$>0.05, respectively. FIGS. 5A–5D contain graphs of the influence of the peptides E . . . PL (SEQ ID NO:3) and E . . . PY (SEQ ID NO:4) on the EAR response to dopamine in the two $D_2DA$ receptor-transfected cell systems. Both peptides demonstrated statistically significant activation, $t_{(7)}$=25.47, $\rho$<0.0001 and $t_{(3)}$=69.830, $\rho$<0.0001, respectively, in the LtK system. However, neither of the E . . . PL (SEQ ID NO:3) and E . . . PY (SEQ ID NO:4) peptides influenced the dopamine-induced EAR of the CHO cells significantly, with $t_{(3)}$=1.542, $\rho$>0.05 and $t_{(7)}$=1.283, $\rho$>0.05, respectively. Three remaining eight peptides exhibited statistically significant effects on at least one of the two receptor-transfected cell systems (Table 3). The overall "hit rate", as measured by modulation of the kinetics of the EAR of two transfected cell lines to dopamine, for these peptides was thus 50% (i.e., six of twelve peptide candidates that were synthesized and tested statistically significantly altered EAR in one or both of the $D_2DA$ receptor-transfected cell systems used). All $D_2DA$ targeted peptides whose effects reached significance increased EAR.

A set of EAR dose response curves were computed for the SHQR peptide (SEQ ID NO:1) across concentrations of dopamine ($10^{-8.5}$ M to $10^{-5.5}$ M) and the SQHR peptide (SEQ ID NO: 1; 10 nM to 3 $\mu$M) (not shown). LtK cells were used for these experiments. The resulting dose response curves manifested asymptotic sigmoidal kinetics, suggestive of positive cooperativity.

Tables 3, 4, and 5 show the sequences of the various peptides synthesized by the methods of the present invention and their effects on the cell test systems.

TABLE 3

HUMAN DOPAMINE $D_2$ ($D_2DA$) RECEPTOR TARGETED PEPTIDES

| SEQUENCE | SEQ ID NO | DIRECT EFFECT CHO | DIRECT EFFECT LtK | MODULATORY EFFECT CHO | MODULATORY EFFECT LtK |
|---|---|---|---|---|---|
| H-SHQRWEYKGVNCIVY-OH | 1 | *** | *** | *** | *** |
| H-THQAFHYCNKQCLVI-OH | 2 | ? | ? | ns | ns |
| H-ERNRKPYRPKNKYLL-OH | 3 | ? | ? | ns | *** |
| H-ERNKLNYKNKNKYIL-OH | 4 | ? | ? | ns | *** |
| H-SHTAYHWMSCGKIVI-OH | 5 | ns | ns | *** | * |
| H-SRQAFHYKNVQVLVL-OH | 6 | ? | ? | ns | ns |
| H-SHQAWRYKNVNCYVI-OH | 7 | ? | ns | ? | *** |
| H-GETAFRYVNCNVYVYI-OH | 8 | ** | *** | ns | ns |
| H-GHSAWRWKSKNVYMI-OH | 9 | ns | ns | ns | ns |
| H-NASALHLVGVQCWVY-OH | 10 | ? | ns | ? | ns |
| H-SWQAIRICQKGVLMY-OH | 11 | ? | ns | ? | ns |
| H-SHSRWRIVSVNVLCY-OH | 12 | ? | ns | ? | ns |

*0.01 < $\rho$ $\leq$ 0.05,
**0.001 < $\rho$ $\leq$ 0.01,
***$\rho$ $\leq$ 0.001.
? = not yet tested,
ns = not significant.

EXAMPLE 2

Peptides derived from receptor protein systems other than the $D_2DA$ receptor were also tested for their effects on their respective receptors. For the human muscarinic M1 receptor, CHO cells were transfected with the muscarinic M1 receptor cDNA derived from a human cDNA library essentially as described by Buckley et al. (*Mol. Pharmacol.* 1989 35:469–476). Briefly, the coding region of the M1 receptor was obtained from a human cDNA library and cloned into the expression vector pcDNA3 (Invitrogen, San Diego, Calif.). CHO-K1 cells were transformed with the construct, using the calcium phosphate method. Stably expressing transformants were obtained in the presence of 250 $\mu$g/ml geneticin. Transformed cell lines expressing the human NGF receptor also were obtained. The effects of the peptides derived by the methods of the present invention on the activities of the corresponding receptors in the transformed cell lines were evaluated in the same manner as described above for the $D_2DA$ -targeted algorithmically derived peptides, using the EAR test system.

Figure 6:
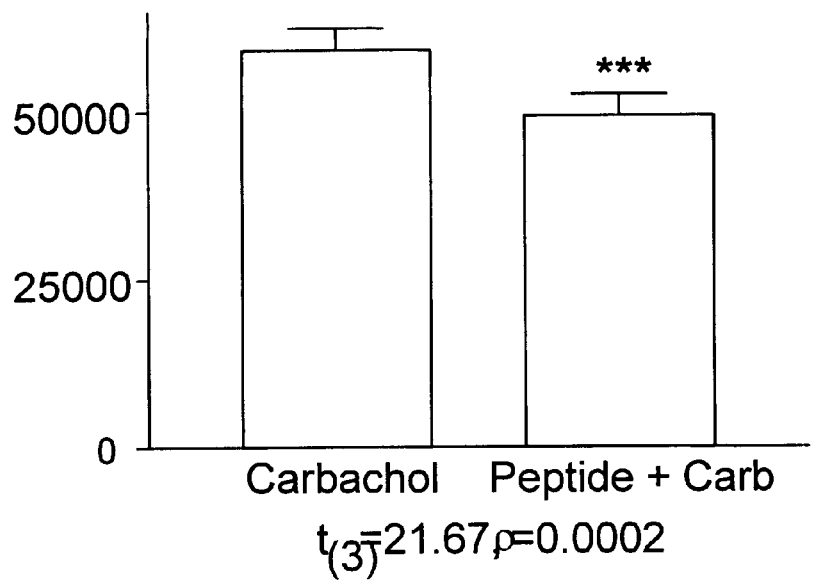
FIG. 6A is a graph showing the effects of the M1 receptor-derived peptide ITFT (SEQ ID NO:9) on the EAR responses of the human M1 receptor-transfected CHO cell system to carbachol infusion left, control with carbachol alone, right, carbachol plus ITFT peptide.
FIG. 6B is a graph showing the effects of the M1 receptor-derived peptide FSFQ (SEQ ID NO:7) on the EAR responses of the human M1 receptor-transfected CHO cell system to carbachol infusion left, control with carbachol alone, right, carbachol plus FSFQ peptide.
Figure 6:
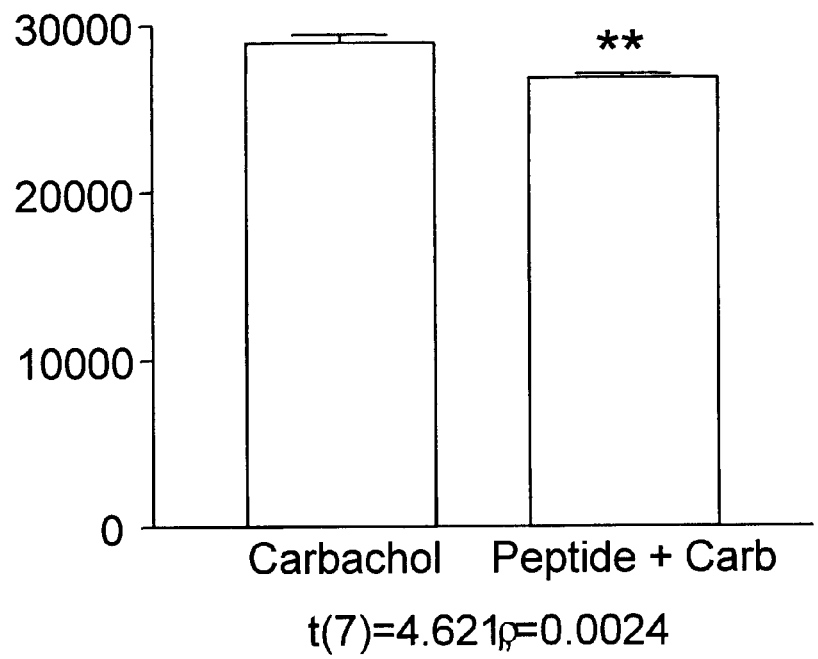

In the case of the MI receptor, ten peptides were obtained, using the methods of the present invention. Of these ten peptides, five (50%) had a statistically significant effect on the EAR due to carbachol in the M1 receptor-transfected CHOK1 cells (e.g., FIGS. 6A–6B, Table 4). All these effects were direct or modulatory decreases in EAR. This contrasts with the positive direct or modulatory effects of the tested peptides on the EAR to dopamine in $D_2DA$ receptor-transfected cell lines.

TABLE 4

HUMAN MUSCARINIC M1 RECEPTOR TARGETED PEPTIDES

| SEQUENCE | SEQ ID NO | DIRECT EFFECT | MODULATORY EFFECT |
|---|---|---|---|
| H-FSFQCKSINYEALGY-OH | 13 | ** | ** |
| H-FSFGVKSWQYHALGY-OH | 14 | ns | * |
| H-ITFTVKGLTLAAFTY-OH | 15 | ? | *** |
| H-ISFNKCTWSFERYSL-OH | 16 | ns | * |
| H-FNLSVKQWNYRAYNL-OH | 17 | ns | ** |
| H-LNYQKKQYTYAAWQF-OH | 18 | ns | ns |
| H-LTYGVMNYGFAAFGF-OH | 19 | ns | ns |
| H-LGFSVCPITLAELTY-OH | 20 | ns | ns |
| H-LGLGVCPINLAALTW-OH | 21 | ? | ns |
| H-LTWNVKTYSLHELPL-OH | 22 | ns | ns |

*$0.01 < \rho \leq 0.05$,
**$0.001 < \rho \leq 0.01$,
***$\rho \leq 0.001$.
? = not yet tested,
ns = not significant.

For the NGF receptor, 11 peptides were obtained, using the methods of the present invention. Of these 11 peptides, eight (73%) exhibited a statistically significant change in EAR (Table 5).

TABLE 5

HUMAN NERVE GROWTH FACTOR RECEPTOR TARGETED PEPTIDES

| SEQUENCE | SEQ ID NO | DIRECT EFFECT | MODULATORY EFFECT |
|---|---|---|---|
| H-DLCRSARSDIEVTEY-OH | 23 | ** | *** |
| H-RFVASAATEIEVNRL-OH | 24 | ns | ** |
| H-HYCASADPRIHKNAL-OH | 25 | ns | *** |
| H-DFVDGAAGRLHKGEY-OH | 26 | ns | ** |
| H-DIKATEATDIEKGHL-OH | 27 | ns | *** |
| H-RFVDNDATDIEKGRI-OH | 28 | * | *** |
| H-RFVRGDRNHFDCGEL-OH | 29 | * | *** |
| H-HFVRNERTHFDVSAL-OH | 30 | * | * |
| H-AYKHNEATDIEKGDF-OH | 31 | ns | ns |
| H-HIKRKEATHIEKSAL-OH | 32 | ns | ns |
| H-HIVEGRAPEIACGEY-OH | 33 | ns | ns |

*$0.01 < \rho \leq 0.05$,
**$0.001 < \rho \leq 0.01$,
***$\rho \leq 0.001$.
? = not yet tested,
ns = not significant.

Thus, 33 total peptides obtained using the methods of the present invention, for all of the receptor systems tested. Of these, 19 had a significant effect on the EAR of the transformed cell lines directly or in response to the native ligand, resulting in an overall hit rate of 57.6%. At a rate of 5 per 100,000, p(B)=0.00005, as the random combinatorial prior probability of hits, and 2 per 4, p(A)=0.5 as the probability of physiological action observed of eigenvector template-generated peptides, a Bayesian theorem says that the latter would occur under conditions of the former like:

$$\frac{p(A|B)p(B)}{p(A)} = \frac{0.000025 \times 0.00005}{0.5} = 0.25 \times 10^{-8}.$$

Thus, an overall average hit rate of 57.6% achieved by the receptor-targeted algorithmically-derived peptides produced by the methods of the present invention appears to be orders of magnitude more efficient for lead peptide generation when compared to the conventional methods of randomly generated peptide libraries.

Cross-over experiments were performed to determine the specificity of the active peptides for the receptor protein from which they were derived. When the $D_2DA$ targeted algorithmically-derived peptides that had a significant effect on EAR to dopamine in $D_2DA$ receptor-transfected cell lines in were tested for their influence on the EAR to carbachol in M1 receptor-transfected CHO-K1 cells, no effect was observed. Similarly, no effect on the EAR to dopamine in $D_2DA$ receptor-transfected cell lines was observed in the presence of the peptides that exhibited a negative allosteric effect in the M1 receptor-transfected cell lines. Therefore, the peptides appear to be selective for the mode-matching receptor proteins from which they are derived.

EXAMPLE 3

Using the redundant subsequence template method described above, peptides were derived from the known polypeptide calcitonin. The parent family of known calcitonins are 31 amino acids in length, which was reduced to 10 amino acids using the redundant subsequence template method to produce the peptides listed in Table 7. The redundant subsequences were generated by examination of the calcitonin sequences of eight different species (Table 6).

TABLE 6

| Species | Four-number Hydrophobic Free Energy Codes | Nonoverlapping Repeated Subsequences |
|---|---|---|
| Human | 3113113331141124134214411241312 | 4112413; 311 |
| Swine | 3113113331244213114224113141421 | 1131; 421 |
| Cow | 3113113331244323114224113141421 | 1131; 142 |
| Sheep | 3113113331244323114224113141421 | 1131; 142 |
| Rat | 3113113331141123134214411141312 | 1141; 3112 |
| Eel | 3113113331331123233114421231211 | 3311; 311 |
| Salmon | 3113113331331123233114421111111 | 3311; 311; 111 |

Conventionally, calcitonin is administered by daily injections to post-menopausal women suffering from osteoporosis. By reducing the peptide length from 31 to 10 amino acids, the resulting peptides are more easily administered by transdermal and inhalation methods. The peptides listed in Table 7 are examples of peptides generated from a human non-overlapping redundant subsequence template (i.e., 3114112413), and are weighted by the amino acid distribution of the human calcitonin receptor.

Examples of Human Calcitonin-Targeted Peptides from Non-Overlapping Redundant Substring Template of Human Calcitonin

| SEQ ID | Sequence |
|---|---|
| 34 | KPNLPNELNK |
| 35 | VTNLGNHIGV |
| 36 | CNNFSPDITV |
| 37 | MQQITTHFQC |

Examples of Human Calcitonin-Targeted Peptides from
Non-Overlapping Redundant
Substring Template of Human Calcitonin

| SEQ ID | Sequence |
|---|---|
| 38 | VNTFGTELSC |
| 39 | CNNIGNRLSC |
| 40 | KGNFTPEWPC |
| 41 | MGPLPQAFQC |
| 42 | KSNIGPALTM |
| 43 | VSQYGQELQV |
| 44 | VSPYQSHFNV |
| 45 | MGGWGPALNC |
| 46 | CTGYTNAIQM |
| 47 | MNTLQQAYPK |
| 48 | VQPYNGELNM |
| 49 | VTNWNGRINK |
| 50 | MQNFPTAINV |
| 51 | VPSIQGHYGM |
| 52 | VGNLTQHYTK |
| 53 | VPPFTNHWQK |
| 54 | VGTLNPAFSV |
| 55 | CGNYGTRFSK |
| 56 | CSSLQQALTV |
| 57 | MPSIPTHLNK |
| 58 | KNNYGQAFTV |
| 59 | KNQLNTEINC |
| 60 | KNPLNNHLNM |
| 61 | VNGIGQAINV |
| 62 | CPGITGDFQK |
| 63 | MTQFQSHITV |
| 64 | VQTYPPHFPV |
| 65 | KGNLNTDLNM |
| 66 | VTPLSSAINK |
| 67 | VNNLSSEYNV |
| 68 | MPPWPSDYPC |
| 69 | KQSFQSELNK |
| 70 | VPSLTTRLQV |
| 71 | VQPLQGHLPV |
| 72 | VSQFNQAWGV |
| 73 | VPSLNSALGV |
| 74 | MNSIQTDFTM |
| 75 | VQSLTNDISK |
| 76 | KGNINPAYNV |
| 77 | KTGLNNEINV |
| 78 | VQSFTNEIQC |
| 79 | KTTINGHISK |
| 80 | VGGYGTDYNM |
| 81 | MQGYTNDIPV |
| 82 | VNQWQNHYTM |
| 83 | KPTFSNAYNV |
| 84 | VTNFSNALSM |
| 85 | VTPINSEFPC |
| 86 | KNQLNTHIGK |
| 87 | VQSINNAIGK |
| 88 | MGTFQPDWQV |
| 89 | VQTISSRWGK |
| 90 | MGNITQDLQC |
| 91 | KGSYTTELGV |
| 92 | KNSYSPELTV |
| 93 | CNSYTPEFPC |

The methods of the present invention may be used to produce peptides useful in variety of investigative, therapeutic and diagnostic applications as listed in part in the examples listed above. In addition to these applications, the peptides may be used in the detection and/or treatment of cancerous tumors. The peptides may also be used in the detection and/or treatment of various other disease conditions, and may also be useful in the detection of contaminants in food, water or soil. It will be appreciated that if the sequence of a particular polypeptide that is specifically or exclusively associated with the disease condition, tumor, or contaminant is known, then peptides that will bind, modulate the function of, activate or inhibit those polypeptides may be synthesized by using the methods of the present invention. When used to treat a tumor, the peptide may be conjugated to or incorporate a cytotoxic agent, such as a radioisotope or a toxin. When used for detection, the peptides may be conjugated to a molecule that can be visualized or otherwise detected, such as a radioisotope, a chromophore or a fluorophore. The peptides of the present invention may be used to screen bodily samples for the presence or absence of a particular polypeptide. Examples of such bodily samples include blood, plasma, blood products, urine samples, fecal samples, tissue biopsy samples, skin samples, semen samples, and epithelial cell samples. When used to screen for tumors or disease conditions, or when used as a therapeutic, the peptides may be included as a component in a diagnostic or therapeutic kit, respectively. The peptides may also be used in areas of research, such as molecular biology, pharmacology, neurobiology, intracellular signaling and the like, to explore the functions and pharmacological responsivities of proteins, polypeptides or peptides of unknown functions. For example, a tissue culture cell line transfected with a cloned orphan receptor may be incubated with various mode-matched peptides and tested for any number of cellular activities that may be associated with that receptor. The use of peptides in general in such applications are well known to those in the art; therefore the peptides produced by the methods of the present invention may be used in the above-cited applications in the usual manner, without the need for undue experimentation.

Although the invention herein has been described with reference to particular embodiments, it is to be understood that these embodiments are merely illustrative of various aspects of the three template generating methods and the amino acid assignment methods of the invention. Thus, it is to be understood that numerous modifications may be made in the illustrative embodiments and other arrangements may be devised without departing from the spirit and scope of the invention. Throughout this application various publications may be cited. Where cited, the contents of these publications are hereby incorporated by reference into the present application.

What is claimed is:

1. A method for synthesizing a peptide or a peptide-like molecule based on matching a physicochemical mode of a target polypeptide or protein to the same physicochemical mode of said peptide or peptide-like molecule, comprising the steps of:

assigning to each member of a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each peptide constituent group encompasses a range of said ordered numerical values, and each member of said set of peptide constituents belongs to only one peptide constitutent group;

creating a polypeptide physicochemical data series by replacing each amino acid in an amino acid sequence of said target polypeptide or protein with said numerical value corresponding to said each amino acid in said amino acid sequence of said target polypeptide or protein;

calculating one or more polypeptide eigenvalues and a corresponding polypeptide eigenvector associated with each of said one or more polypeptide eigenvalues by linear decomposition of an autocovariance matrix formed from a sequentially lagged data matrix of said polypeptide physicochemical data series;

ordering said one or more polypeptide eigenvalues and said corresponding polypeptide eigenvectors from largest to smallest;

selecting one or more of said polypeptide eigenvectors; transforming said one or more of said polypeptide eigenvectors into an eigenvector template;

forming a graph of said eigenvector template, wherein said numerical values are graphed along the y-axis of said graph and ordered position in said eigenvector template is graphed along the x-axis of said graph;

partitioning said graph along said y-axis according to said ranges of said numerical values defining said peptide constituent groups, to form a plurality of y-axis ranges;

assigning one of said peptide constituents to each position in said peptide or peptide-like molecule by using said graph as a template, wherein at each ordered position in said eigenvector template along said x-axis of said graph, said one of said peptide constituents assigned to said ordered position has a numerical value that is within said y-axis range of said ordered point; and synthesizing said peptide or peptide-like molecule.

2. The method of claim 1, wherein said peptide constituents are the twenty naturally occurring amino acids.

3. The method of claim 1, wherein said peptide constituent chosen in said step of assigning one of said peptide constituents to each position in said peptide or a peptide-like molecule is chosen randomly from among the members of said peptide constituent group.

4. The method of claim 3, further comprising weighting each of said members of said set of peptide constituents on the basis of an amino acid distribution in a selected amino acid pool.

5. The method of claim 4, wherein said selected amino acid pool is derived from one or more of a biological fluid, a biological organ, a protein, a polypeptide, a peptide, and a wavelet or redundant amino acid substring analysis of a peptide or polypeptide.

6. The method of claim 1, further comprising:

(i) transforming said amino acid sequence of said target polypeptide or protein of length N and comprised of amino acids $A_1, A_2, \ldots A_N$ into a polypeptide hydrophobic free energy series $H_1, H_2, \ldots H_N$, where $H_1$ represents the hydrophobic free energy value of amino acid $A_1$ in the Ith position in said amino acid sequence;

(ii) forming an M×M autocovariance matrix from data column vectors $V_1^T=(H_1, H_2 \ldots, H_{n-M})$, $V_2^T=(H_2, H_3, \ldots, H_{n-M+1}), \ldots, V_M^T=(H_M, H_{M+1}, \ldots, H_n)$ such that $C_M=1/K\{H_iH_i^T\}$, where $K=n-M+1$, and M is chosen to maximize a least squares fit of a leading eigenfunction of said target polypeptide or protein with a hydropathy plot of said target polypeptide or protein;

(iii) calculating said polypeptide eigenvalues and said corresponding polypeptide eigenvectors, $X_i^R(j)$, of $C_M$, wherein $i=1 \ldots M$ and labels said polypeptide eigenvector, and $j=1 \ldots M$ and refers to a jth component of said corresponding eigenvector;

iv) using said polypeptide eigenvectors as multiplicative weights to transform said polypeptide hydrophobic free energy series into M statistically weighted polypeptide eigenfunctions, expressed as $\Psi_i^R(j)$, where $i=1 \ldots M$ labels the polypeptide eigenvector and $j=1 \ldots N-M$ indexes a jth component of said polypeptide eigenfunction, as $$\Psi_i^R(j) = \sum_{k=1}^{M} X_i(k)H_{j-k+1} \text{ or}$$

$$\Psi_i^R(j) = \sum_{k=1}^{M} X_i(k)H_j$$

for $j-k+1>0$, and where $\Psi_1^R$ is said leading eigenfunction; and (v) choosing one or more of said polypeptide eigenvectors for graphing.

7. The method of claim 6, wherein M is $\leq 50$.

8. The method of claim 6, wherein said eigenvector is graphed along an x-axis from 1 to M.

9. The method of claim 6, wherein i of $X_i^R(j)$ is between 1 and 4.

10. The method of claim 6, wherein i of $X_i^R(j)$ is $\geq 2$.

11. A method for synthesizing a peptide or a peptide-like molecule based on matching a physicochemical mode of a peptide or a peptide-like molecule to the same physicochemical mode of a target polypeptide or protein, comprising the steps of:

assigning to each member of a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each peptide constituent group encompasses a range of said ordered numerical values, and each member of said set of peptide constituents belongs to only one peptide constituent group;

creating a polypeptide physicochemical data series by replacing each amino acid in an amino acid sequence with said numerical value corresponding to said each amino acid in said amino acid sequence;

calculating one or more polypeptide eigenvalues and a corresponding polypeptide eigenvector associated with each of said one or more polypeptide eigenvalues by linear decomposition of an autocovariance matrix formed from a sequentially lagged data matrix of said polypeptide physicochemical data series;

ordering said one or more polypeptide eigenvalues and said corresponding polypeptide eigenvectors from largest to smallest;

selecting one or more of said polypeptide eigenvectors;

forming a vector, said vector being a sum of the products of each of said plurality of said polypeptide eigenvectors multiplied by the corresponding eigenvalue;

forming a graph of said vector, wherein said numerical values are graphed along the y-axis of said graph, and ordered position in said eigenvector template is graphed along the x-axis of said graph;

partitioning said graph along said y-axis according to said range of said numerical values defining said peptide constituent groups, to form a plurality of y-axis ranges;

assigning one of said peptide constituents to each position in said peptide or a peptide-like molecule by using said graph of said vector as a template, wherein at each ordered position in said eigenvector template along said x-axis of said graph, said one of said peptide constituents assigned to said ordered position has a numerical value that is within said y-axis range of said ordered position; and synthesizing said peptide or peptide-like molecule.

12. The method of claim 11, wherein said peptide constituents are the twenty naturally occurring amino acids.

13. The method of claim 11, wherein said member of said peptide constituent group chosen in said step of assigning one of said peptide constituents to each position in said peptide or a peptide-like molecule is chosen randomly from among the members of said peptide constituent group.

14. The method of claim 13, further comprising weighting each of said members of said set of peptide constituents on the basis of an amino acid distribution in a selected amino acid pool.

15. The method of claim 14, wherein said selected amino acid pool is derived from one or more of a biological fluid, a biological organ, a protein, a polypeptide, a peptide, and a wavelet or redundant amino acid substring analysis of a peptide or polypeptide.

16. The method of claim 11, further comprising:
(i) transforming said amino acid sequence of said target polypeptide or protein of length N and comprised of amino acids $A_1, A_2, \ldots A_N$ into a polypeptide hydrophobic free energy series $H_1, H_2, \ldots H_N$ where $H_1$ represents the hydrophobic free energy value of amino acid $A_1$ in the Ith position in said polypeptide amino acid sequence;
(ii) forming an M×M autocovariance matrix from the data column vectors $V_1^T=(H_1, H_2, \ldots, H_{n-M})$, $V_2^T=(H_2, H_3, \ldots, H_{n-M+1}), \ldots, V_M^T=(H_M, H_{M+1}, \ldots, H_n)$ such that $C_M=1/K\{H_i H_i^T\}$, where $K=n-M+1$, and M is chosen to maximize a least squares fit of said leading eigenfunction of said target polypeptide or protein with a hydropathy plot of said target polypeptide or protein;
(iii) calculating said polypeptide eigenvalues and said corresponding polypeptide eigenvectors, $X_i^R(j)$ of $C_M$, wherein $i=1 \ldots M$ and labels said polypeptide eigenvector, and $j=1 \ldots M$ and refers to a jth component of said corresponding eigenvector;
(iv) using said polypeptide eigenvectors as multiplicative weights to transform said polypeptide hydrophobic free energy series into M statistically weighted polypeptides, expressed as $X_i^R(j)$, where $i=1 \ldots M$ labels the polypeptide eigenvector and $j=1 \ldots N-M$ (or $j=1 \ldots N$) indexes a jth component of said polypeptide eigenfunction, as $$\Psi_i^R(j) = \sum_{k=1}^{M} X_i^R(k) H_{j-k+1} \text{ or}$$

$$\Psi_i^R(j) = \sum_{k=1}^{M} X_i(k) H_j$$

for $j-k+1>0$ (or $j>0$), and where $\Psi_1^R$ is said leading eigenfunction; and
(v) choosing a plurality of said polypeptide eigenvectors for graphing.

17. The method of claim 16, wherein M is $\leq 50$.

18. The method of claim 16, wherein said eigenvector is graphed along an x-axis from 1 to M.

19. The method of claim 16, wherein i of $X_i^R(j)$ is between 1 and 4.

20. The method of claim 16, wherein i of $X_i^R(j)$ is $\geq 2$.

21. A method for designing a peptide or a peptide-like molecule based on matching a physicochemical mode of a target polypeptide or protein to the same physicochemical mode of said peptide or peptide-like molecule, comprising the steps of:

assigning to each member of a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each peptide constituent group encompasses a range of said ordered numerical values, and each member of said set of peptide constituents belongs to only one peptide constituent group;

creating a polypeptide physicochemical data series by replacing each amino acid in an amino acid sequence of said target polypeptide or protein with said numerical value corresponding to said each amino acid in said amino acid sequence;

decomposing said polypeptide physicochemical data series into translated and scaled version of a mother wavelet, w, as $$W^R(a, b) = (1/\sqrt{a}) \int_0^i H(i) w\left(\frac{i-b}{a}\right) di$$

wherein w denotes a mother wavelet function;

separating $W^R(a,b)$ into polypeptide modulus parts and polypeptide phase parts;

graphing said polypeptide phase parts on a polypeptide phase graph, wherein the x-axis of said polypeptide phase graph indexes sequence position and the y-axis of said polypeptide phase graph is numbered in units of one of relative dilation (dd) and wavelet wavelengths ($\overline{\omega}$);

graphing said polypeptide modulus parts on a polypeptide modulus graph, wherein the x-axis of said polypeptide modulus graph indexes sequence position and the y-axis of said polypeptide modulus graph is numbered in units of one of relative dilation (dd) and wavelet wavelengths ($\overline{\omega}$);

identifying a plurality of polypeptide maximal phase amplitudes in said polypeptide phase graph and a plurality of polypeptide moduli in said polypeptide modulus graph, respectively;

creating a peptide physicochemical data series by replacing each peptide constituent in a peptide sequence of the peptide or peptide-like molecule with the numerical value corresponding to said each peptide constituents in said peptide sequence;

decomposing said peptide physicochemical data series into translated and scaled version of a mother wavelet, w, as $$W^L(a, b) = (1/\sqrt{a}) \int_0^i H(i) w\left(\frac{i-b}{a}\right) di$$

wherein w denotes a mother wavelet function;

separating $W^L(a,b)$ into peptide modulus parts and peptide phase parts;

graphing said peptide phase parts on a peptide phase graph, wherein the x-axis of said peptide phase graph indexes sequence position and the y-axis of said peptide phase graph is numbered in units of one of relative dilation (dd) and wavelet wavelengths ($\overline{\omega}$);

graphing said peptide modulus parts on a peptide modulus graph, wherein the x-axis of said peptide modulus graph indexes sequence position and the y-axis of said peptide modulus graph is numbered in units of one of relative dilation (dd) and wavelet wavelengths ($\overline{\omega}$);

identifying a plurality of peptide maximal phase amplitudes in said peptide phase graph and a plurality of peptide moduli in said peptide modulus graph, respectively;

comparing said plurality of polypeptide maximal phase amplitudes to said plurality of peptide maximal phase amplitudes to determine if said plurality of polypeptide maximal phase amplitudes match said plurality of peptide maximal phase amplitudes;

comparing said plurality of polypeptide moduli in said polypeptide modulus graph to said plurality of peptide moduli in said peptide modulus graph to determine if said plurality of polypeptide moduli match said plurality of peptide moduli, wherein a match between said plurality of polypeptide maximal phase amplitudes and said plurality of peptide maximal phase amplitudes, and a match between said plurality of polypeptide moduli and said plurality of peptide moduli, indicates said peptide or peptide-like molecule may bind to and/or otherwise modulate said polypeptide;

identifying one or more amino acid subsequences of said amino acid sequence of said target polypeptide or protein, said one or more amino acid subsequences corresponding to said polypeptide physicochemical data series that are mode-matched to said peptide physicochemical data series and further being colocalized in the dilate and sequence spaces of one or both of said peptide phase graph and said peptide modulus graph;

forming a graph of each of said one or more amino acid subsequences, wherein said numerical values are graphed along the y-axis of said graph and ordered position in each of said one or more amino acid subsequences are graphed along the x-axis;

partitioning said graph along said y-axis according to said range of said numerical values defining said peptide constituent groups to form a plurality of y-axis ranges; and assigning a member of said peptide constituent group to each position in said peptide or peptide-like molecule by using said graph of each of said one or more amino acid subsequences as a template, wherein at each ordered position in said template along the x-axis of said graph, said member of said peptide constituent group assigned to said ordered position has a numerical value that is within said y-axis range of said ordered position.

22. The method of claim 21, wherein said peptide constituents are the twenty naturally occurring amino acids.

23. The method of claim 21, wherein said peptide constituent chosen in said step of assigning one of said peptide constituents to each position in said peptide or a peptide-like molecule is chosen randomly from among the members of said peptide constituent group.

24. The method of claim 23, further comprising weighting each of said members of said set of peptide constituents on the basis of an amino acid distribution in a selected amino acid pool.

25. The method of claim 24, wherein said selected amino acid pool is derived from one or more of a biological fluid, a biological organ, a protein, a polypeptide, a peptide, and a wavelet or redundant amino acid substring analysis of a peptide or polypeptide.

26. A method for designing a peptide or a peptide-like molecule based on matching a physicochemical mode of a target polypeptide and/or protein to the same physicochemical mode of said peptide or peptide-like molecule, comprising the steps of:

assigning to each member of a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each peptide constituent group encompasses a range of said ordered numerical values, and each member of said set of peptide constituents belongs to only one peptide constituent group;

creating a polypeptide physicochemical data series by replacing each amino acid in an amino acid sequence of said target polypeptide or protein with said numerical value corresponding to said each amino acid in said amino acid sequence;

decomposing said polypeptide physicochemical data series with a family of functions $W_{j,n,k}(x)=2^{-j/2}W_n(2^{-j}x-k)$ which when j,n are positive integers and k has an integer value, are organized in one or more tree structures, each of said one or more tree structures being being composed of a plurality of nodes, each of said nodes being in the form of:

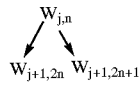

wherein $W_{j,n,k}(x)$ is computed for a mother wavelet function;

computing and frequency-ordering best level and best tree representations of a physicochemical polypeptide series based on SURE and Shannon entropy criteria;

graphing said frequency-ordered best level representation on a polypeptide best level graph, wherein the x-axis of said polypeptide best level graph indexes sequence position and the y-axis of said polypeptide best level graph is numbered in units of wavelet wavelengths, $\bar{\omega}$;

graphing said frequency-ordered best tree representation, wherein the x-axis of said polypeptide best tree graph indexes sequence position and the y-axis of said best tree graph is numbered in units of one of relative dilation (dd) and wavelet wavelengths, $\bar{\omega}$;

identifying a plurality of polypeptide maximal coefficient amplitudes, each of said plurality of polypeptide maximal coefficient amplitudes being derived from said polypeptide best level graph and said polypeptide best tree graph;

creating a peptide physicochemical data series by replacing each peptide constituent in a peptide sequence of said peptide or a peptide-like molecule with said numerical value corresponding to said peptide constituent in said peptide sequence;

decomposing said peptide physicochemical data series with a family of functions $W_{j,n,k}(x)=2^{-j/2}W_n(2^{-j}x-k)$, which when j,n are positive integers and k has an integer value, are organized in one or more tree structures, each of said one or more tree structures being composed of a plurality of nodes, each of said nodes being in the form of:

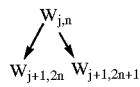

wherein $W_{j,n,k}(x)$ is computed for a mother wavelet function;

computing and frequency-ordering best level and best tree representations of a physicochemical peptide series based on SURE and Shannon entropy criteria;

graphing said frequency-ordered best level representation on a peptide best level graph, wherein the x-axis of said peptide best level graph indexes sequence position and the y-axis of said peptide best level graph is numbered in units of wavelet wavelengths, $\bar{\omega}$;

graphing said frequency-ordered best tree representation, wherein the x-axis of said peptide best tree graph indexes sequence position and the y-axis of said best tree graph is numbered in units of one of relative dilation (dd) and wavelet wavelengths, $\bar{\omega}$;

identifying a plurality of peptide maximal coefficient amplitudes, each of said plurality of peptide maximal coefficient amplitudes being derived from said peptide best level graph and said peptide best tree graph;

comparing said plurality of polypeptide maximal coefficient amplitudes to said plurality of peptide maximal coefficient amplitudes to determine if said plurality of polypeptide maximal coefficient amplitudes match said plurality of peptide maximal coefficient amplitudes;

comparing said plurality of polypeptide moduli in said polypeptide modulus graph to said plurality of peptide moduli in said peptide modulus graph to determine if said plurality of polypeptide moduli match said plurality of peptide moduli, wherein a match between said plurality of polypeptide maximal coefficient amplitudes and said plurality of peptide maximal coefficient amplitudes indicates said peptide or peptide-like molecule may bind to and/or otherwise activate or inhibit the function of said target polypeptide or protein;

identifying one or more amino acid subsequences of said amino acid sequence of said target polypeptide or protein, said one or more amino acid subsequences corresponding to said polypeptide physicochemical data series that are mode-matched to said peptide physicochemical data series and further being colocalized in the dilate and sequence spaces of one or both of said peptide phase graph and said peptide modulus graph;

forming a graph of each of said one or more amino acid subsequences, wherein said numerical values are graphed along the y-axis of said graph and ordered position in each of said one or more amino acid subsequences are graphed along the x-axis;

partitioning said graph along said y-axis according to said range of said numerical values defining said peptide constituent groups to form a plurality of y-axis ranges; and assigning a member of said peptide constituent group to each position in said peptide or peptide-like molecule by using said graph of each of said one or more amino acid subsequences as an eigenvector template, wherein at each ordered position in said template along the x-axis of said graph, said member of said peptide constituent group assigned to said ordered position has a value that is within said y-axis range of said ordered position.

27. The method of claim 26, wherein said peptide constituents are the twenty naturally occurring amino acids.

28. The method of claim 27, wherein said peptide constituent chosen in said step of assigning one of said peptide constituents to each position in said peptide or a peptide-like molecule is chosen randomly from among the members of said peptide constituent group.

29. The method of claim 28, further comprising weighting each of said members of said set of peptide constituents on the basis of an amino acid distribution in a selected amino acid pool.

30. The method of claim 29, wherein said selected amino acid pool is derived from one or more of a biological fluid, a biological organ, a protein, a polypeptide, a peptide, and a wavelet or redundant amino acid substring analysis of a peptide or polypeptide.

31. A method for designing a peptide or a peptide-like molecule based on matching a physicochemical mode of a target polypeptide or protein to the same physicochemical mode of said peptide or peptide-like molecule, comprising the steps of:

assigning to each member of a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each peptide constituent group encompasses a range of said ordered numerical values, and each member of said set of peptide constituents belonging to only one peptide constituent group;

assigning a different character to each of said plurality of peptide constituent groups;

creating a symbolic polypeptide or protein physicochemical data series by replacing each amino acid in an amino acid sequence of said target polypeptide or protein with one of said characters, said character corresponding to said peptide constituent group to which said amino acid is assigned;

computing all non-overlapping redundant subsequences of said characters in said symbolic polypeptide physicochemical data series, selecting first the longest and leftmost such subsequences in the symbolic polypeptide physicochemical data series, wherein said non-overlapping redundant subsequences of three or more characters are repeated at least twice and such non-overlapping redundant subsequences of two characters are repeated at least three times;

creating a symbolic peptide physicochemical data series by replacing each amino acid in a peptide sequence with one of said characters, said character corresponding to said peptide constituent group to which said amino acid in said amino acid sequence of said target polypeptide or protein is assigned;

computing all non-overlapping redundant subsequences of said characters in said symbolic peptide physicochemical data series, selecting first the longest and leftmost such subsequences in the symbolic peptide physicochemical data series, wherein said non-overlapping redundant subsequences of three or more characters are repeated at least twice and said non-overlapping redundant subsequences of two characters are repeated at least three times;

selecting one or more concatenated of said non-overlapping redundant subsequences of said target polypeptide or peptide to form a redundant subsequence template;

assigning one of said peptide constituents to each position in said redundant subsequence template, each position containing one character, wherein at each position in said redundant subsequence template, said peptide constituent assigned to said position belongs to the same peptide constituent group as said character.

32. The method of claim 31, wherein said peptide constituents are the twenty naturally occurring amino acids.

33. The method of claim 31, wherein said peptide constituent chosen in said step of assigning one of said peptide constituents to each position in redundant subsequence template is chosen randomly from among the members of said peptide constituent group.

34. The method of claim 33, further comprising weighting each of said members of said peptide constituents on the basis of an amino acid distribution in a selected amino acid pool.

35. The method of claim 34, wherein said selected amino acid pool is derived from one or more of a biological fluid, a biological organ, a protein, a polypeptide, a peptide, and a wavelet or redundant amino acid substring analysis of a peptide or polypeptide.

36. A method for matching a physicochemical mode of a peptide or a peptide-like molecule to a physicochemical mode of a target polypeptide or protein to determine if said peptide will bind to and/or otherwise activate and/or inhibit the function of said target polypeptide or protein, comprising the steps of:

assigning to each member of a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each peptide constituent group encompasses a range of said ordered numerical values, and each member of said set of peptide constituents belongs to only one peptide constituent group;

creating a polypeptide physicochemical data series by replacing each amino acid in an amino acid sequence of said target polypeptide or protein with said numerical value corresponding to said each amino acid in said amino acid sequence of said target polypeptide or protein;

calculating one or more polypeptide eigenvalues and a corresponding polypeptide eigenvector associated with each of said one or more polypeptide eigenvalues by linear decomposition of an autocovariance matrix formed from a sequentially lagged data matrix of said polypeptide physicochemical data series;

ordering said one or more polypeptide eigenvalues and said corresponding polypeptide eigenvectors from largest to smallest;

transforming said polypeptide physicochemical data series into one or more polypeptide eigenfunctions, using said ordered polypeptide eigenvectors as multiplicative weights;

transforming said one or more polypeptide eigenfunctions into dominant wavenumbers, using all poles maximum entropy power spectra, to produce polypeptide spectral power peaks;

identifying said polypeptide power spectral peaks;

creating a peptide physicochemical data series by replacing each peptide constituent in a peptide sequence of said peptide or a peptide-like molecule with said numerical value corresponding to said peptide constituent in said peptide sequence;

calculating one or more peptide eigenvalues and a corresponding peptide eigenvector associated with each of said one or more peptide eigenvalues by linear decomposition of an autocovariance matrix formed from said peptide physicochemical data series;

ordering said one or more peptide eigenvalues and said corresponding eigenvectors from largest to smallest;

transforming said peptide physicochemical data series into one or more peptide eigenfunctions, using said ordered peptide eigenvectors as multiplicative weights;

transforming said one or more peptide eigenfunctions into dominant wavenumbers, using all poles maximum entropy power spectra, to produce peptide spectral power peaks;

identifying said peptide power spectral peaks; and comparing said polypeptide spectral power peaks to said peptide spectral power peaks to determine if said polypeptide spectral power peaks match said peptide spectral power peaks, wherein a match between said polypeptide spectral power peaks and said peptide spectral power peaks indicates said peptide or peptide-like molecule may bind to and/or otherwise activate and/or inhibit the function of said target polypeptide or protein.

37. The method of claim 36, further comprising:

(i) transforming said amino acid sequence of said target polypeptide or protein of length N and comprised of amino acids $A_1, A_2, \ldots A_N$ into a polypeptide hydrophobic free energy series $H_1, H_2, \ldots H_N$, where $H_1$ represents the hydrophobic free energy value of amino acid $A_1$ in the Ith position in said polypeptide amino acid sequence;

(ii) forming an M×M autocovariance matrix from data column vectors $V_1^T=(H_1, H_2 \ldots, H_{n-M})$, $V_2^T=(H_2, H_3, \ldots, H_{n-M+1}), \ldots, V_M^T=(H_M, H_{M+1}, \ldots, H_n)$ such that $C_M=1/K\{H_iH_i^T\}$, where $K=n-M+1$, and M is chosen to maximize a least squares fit of a leading eigenfunction of said target polypeptide or protein with a hydropathy plot of said target polypeptide or protein;

(iii) calculating said polypeptide eigenvalues and said corresponding polypeptide eigenvectors, $X_i^R(j)$, of $C_M$, wherein $i=1 \ldots M$ and labels said polypeptide eigenvector, and $j=1 \ldots M$ and refers to a jth component of said corresponding eigenvector;

(iv) using said polypeptide eigenvectors as multiplicative weights to transform said polypeptide hydrophobic free energy series into M statistically weighted polypeptide eigenfunctions, expressed as $\Psi_i^T(j)$, where $i=1 \ldots M$ labels the polypeptide eigenvector and $j=1 \ldots N-M$ (or $j=1 \ldots N$) indexes a jth component of said polypeptide eigenfunction, as $$\Psi_i^R(j) = \sum_{k=1}^{M} X_i(k)H_{j-k+1} \text{ or}$$

$$\Psi_i^R(j) = \sum_{k=1}^{M} X_i(k)H_j$$

for j−k+1>0 (or j>0), and where $\Psi_1^R$ said leading eigenfunction; and (v) choosing one or more of said polypeptide eigenvectors for graphing.

38. The method of claim 37, wherein M is $\leq 50$.

39. The method of claim 37, wherein said polypeptide eigenvector is graphed along an x-axis from 1 to M.

40. The method of claim 37, wherein i of $X_i^R(j)$ is between 1 and 4.

41. The method of claim 37, wherein i of $X_i^R(j)$ is $\geq 2$.

42. The method of claim 37, further comprising:

(i) transforming said sequence of said peptide or a peptide-like molecule of length N and comprised of peptide constituents $A_1, A_2, \ldots A_N$ into a peptide hydrophobic free energy series $H_1, H_2, \ldots H_N$ where $H_1$ represents the hydrophobic free energy value of peptide constituent $A_1$ in the Ith position in said sequence;

(ii) forming an M×M autocovariance matrix from data column vectors $V_1^T=(H_1, H_2 \ldots, H_{n-M})$, $V_2^T=(H_2, H_3, \ldots, H_{n-M+1}), \ldots, V_M^T=(H_M, H_{M+1}, \ldots, H_n)$ such that $C_M=1/K\{H_iH_i^T\}$, where $K=n-M+1$, and M is chosen to maximize a least squares fit of a leading eigenfunction of said peptide with a hydropathy plot of said peptide or peptide-like molecule;

(iii) calculating said peptide eigenvalues and said corresponding peptide eigenvectors, $X_i^L(j)$, of $C_M$, wherein $i=1 \ldots M$ and labels said peptide eigenvector, and $j=1 \ldots M$ and refers to a jth component of said corresponding eigenvector;

(iv) using said peptide eigenvectors as multiplicative weights to transform said peptide hydrophobic free energy series into M statistically weighted peptide eigenfunctions, expressed as $\Psi_i^L(j)$, where $i=1 \ldots M$ labels the polypeptide eigenvector and $j=1 \ldots N-M$ (or $j=1 \ldots N$) indexes a jth component of said polypeptide eigenfunction, as $$\Psi_i^L(j) = \sum_{k=1}^{M} X_i^L(k)H_{j-k+1} \text{ or}$$

$$\Psi_i^R(j) = \sum_{k=1}^{M} X_i(k)H_j$$

for j−k+1>0 (or j>0), and where $\Psi_1^L$ is said leading eigenfunction; and (v) choosing one or more of said peptide eigenvectors for graphing.

43. The method of claim 36, further comprising:

(i) transforming said peptide sequence of said peptide or a peptide-like molecule of length N and comprised of peptide constituents $A_1, A_2, \ldots A_N$ into a peptide hydrophobic free energy series $H_1, H_2, \ldots H_N$ where $H_1$ represents the hydrophobic free energy value of peptide constituent $A_i$ in the ith position in said peptide sequence of said peptide or a peptide-like molecule;

(ii) forming an M×M autocovariance matrix from data column vectors $V_1^T=(H_1, H_2 \ldots, H_{n-M})$, $V_2^T=(H_2, H_3, \ldots, H_{n-M+1}), \ldots, V_M^T=(H_M, H_{M+1}, \ldots, H_n)$ such that $C_M=1/K\{H_iH_i^T\}$, where $K=n-M+1$, and M is chosen to maximize a least squares fit of a leading eigenfunction of said peptide with a hydropathy plot of said peptide or peptide-like molecule;

(iii) calculating said pep tide eigenvalues and said corresponding peptide eigenvectors, $X_i^L(j)$, of $C_M$, wherein $i=1 \ldots M$ and labels said peptide eigenvector, and $j=1 \ldots M$ and refers to a jth component of said corresponding eigenvector;

93

(iv) using said peptide eigenvectors as multiplicative weights to transform said peptide hydrophobic free energy series into M statistically weighted peptide eigenfunctions, expressed as $\Psi_i^L(j)$, where i=1 . . . M labels the polypeptide eigenvector and j=1 . . . N−M (or j=1 . . . N) indexes a jth component of said polypeptide eigenfunction, as $$\Psi_i^L(j) = \sum_{k=1}^{M} X_i^L(k) H_{j-k+1} \text{ or}$$

$$\Psi_i^R(j) = \sum_{k=1}^{M} X_i(k) H_j$$

for j−k+1>0 (or j>0), and where $\Psi_1^L$ is said leading eigenvector; and (v) choosing one or more of said peptide eigenvectors for graphing.

44. A method for matching a peptide or a peptide-like molecule to a target polypeptide or protein to determine if said peptide will bind to and/or otherwise activate and/or inhibit the function of said target polypeptide or protein, comprising the steps of:

assigning to each member of a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each peptide constituent group encompasses a range of said ordered numerical values, and each member of said set of peptide constituents belongs to only one peptide constituent group;

creating a polypeptide physicochemical data series by replacing each amino acid in an amino acid sequence of said target polypeptide or protein with said numerical value corresponding to said amino acid in said amino acid sequence of said target polypeptide or protein;

decomposing said polypeptide physicochemical data series into translated and scaled version of a mother wavelet, w, as $$W^R(a,b) = (1/\sqrt{a}) \int_0^i H(i) w\left(\frac{i-b}{a}\right) di$$

wherein w denotes the chosen mother wavelet function;

separating $W^R(a,b)$ into polypeptide modulus parts and polypeptide phase parts;

graphing said polypeptide phase parts on a polypeptide phase graph, wherein the x-axis of said polypeptide phase graph indexes sequence position and the y-axis of said polypeptide phase graph is numbered in units of one of dilate divisions (dd) and wavelet wavelengths ($\bar{\omega}$);

graphing said polypeptide modulus parts on a polypeptide modulus graph, wherein the x-axis of said polypeptide modulus graph indexes sequence position and the

94 y-axis of said polypeptide modulus graph is numbered in units of one of dilate divisions (dd) and wavelet wavelengths ($\bar{\omega}$);

identifying a plurality of polypeptide maximal phase amplitudes and a plurality of polypeptide moduli in each of said polypeptide phase graph and said polypeptide modulus graph, respectively;

creating a peptide physicochemical data series by replacing each peptide constituent in a peptide sequence of said peptide or a peptide-like molecule with said numerical value corresponding to each said peptide constituent in said peptide sequence;

decomposing said peptide physicochemical data series into translated and scaled version of a mother wavelet, w, as $$W^L(a,b) = (1/\sqrt{a}) \int_0^i H(i) w\left(\frac{i-b}{a}\right) di$$

wherein w denotes the chosen mother wavelet function;

separating $W^L(a,b)$ into peptide modulus parts and peptide phase parts;

graphing said peptide phase parts on a peptide phase graph, wherein the x-axis of said peptide phase graph indexes sequence position and the y-axis of said peptide phase graph is numbered in units of one of relative dilation (dd) and wavelet wavelengths ($\bar{\omega}$);

graphing said peptide modulus parts on a peptide modulus graph, wherein the x-axis of said peptide modulus graph indexes sequence position and the y-axis of said peptide modulus graph is numbered in units of one of dilate divisions (dd) and wavelet wavelengths ($\bar{\omega}$);

identifying a plurality of peptide maximal phase amplitudes and a plurality of peptide moduli in said peptide phase graph and said peptide modulus graph, respectively;

comparing said plurality of polypeptide maximal phase amplitudes in said polypeptide phase graph to said plurality of peptide maximal phase amplitudes in said peptide phase graph respectively to determine if said plurality of polypeptide maximal phase amplitudes match said plurality of peptide maximal phase amplitudes;

comparing said plurality of polypeptide moduli in said polypeptide modulus graph to said plurality of peptide moduli in said peptide modulus graph to determine if said plurality of polypeptide moduli match said plurality of peptide moduli;

wherein a match between said plurality of polypeptide maximal phase amplitudes and said plurality of peptide maximal phase amplitudes, and a match between said plurality of polypeptide moduli and said plurality of peptide moduli, indicates said peptide or peptide-like molecule may bind to and/or otherwise activate and/or inhibit the function of said polypeptide.

45. A method for matching a peptide or peptide-like molecule to a target polypeptide or protein to determine if said peptide or peptide-like molecule will bind to and/or otherwise activate and/or inhibit the function of said target polypeptide or protein, comprising the steps of:

assigning to each member of a a set of peptide constituents a numerical value representative of the hydrophobic free energy of said each member of a set of peptide constituents, said set of peptide constituents including all the members of the set of naturally-occurring amino acids;

arranging said peptide constituents in order of said numerical values;

partitioning said set of peptide constituents into a plurality of peptide constituent groups, whereby each of said peptide constituent groups contains at least one member of said set of peptide constituents, each group encompasses a range of said ordered numerical values, and each member of said peptide constituents belongs to only one peptide constituent group;

creating a polypeptide physicochemical data series by replacing each amino acid in an amino acid sequence of said target polypeptide or protein with said numerical value corresponding to said amino acid in said amino acid sequence of said target polypeptide or protein;

decomposing said polypeptide physicochemical data series with a family of functions $W_{j,n,k}(x)=2^{-j/2}W_n(2^{-j}x-k)$, which when j,n are positive integers and k has an integer value, are organized in one or more tree structures, each of said one or more tree structures being composed of a plurality of nodes, each of said nodes being in the form of:

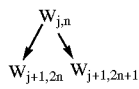

wherein $W_{j,n,k}(x)$ is computed for a mother wavelet function;

computing and frequency-ordering best level and best tree representations of a physicochemical polypeptide series based on SURE and Shannon entropy criteria;

graphing said best level representation on a polypeptide best level graph, wherein the x-axis of said polypeptide best level graph indexes sequence position and the y-axis of said polypeptide best level graph is numbered in units of wavelet wavelengths, $\overline{\omega}$;

graphing said best tree representation on a polypeptide best tree graph, wherein the x-axis of said polypeptide best tree graph indexes sequence position and the y-axis of said polypeptide best tree graph is numbered in units of one of relative dilation (dd) and wavelet wavelengths, $\overline{\omega}$;

identifying a plurality of polypeptide maximal coefficient amplitudes, each of said plurality of polypeptide maximal coefficient amplitudes being derived from said polypeptide best level graph and said polypeptide best tree graph;

creating a peptide physicochemical data series by replacing each peptide constituent in a peptide sequence of said peptide or peptide-like molecule with said numerical value corresponding to said peptide constituent in said peptide sequence;

decomposing said peptide physicochemical data series with the family of functions $W_{j,n,k}(x)=2^{-j/2}W_n(2^{-j}x-k)$, which when j,n are positive integers and k has an integer value, are organized in one or more tree structures, each of said one or more tree structures being comprised of a plurality of nodes, each of said nodes being in the form of

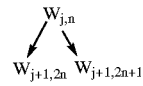

wherein $W_{j,n,k}(x)$ is computed for a mother wavelet function;

computing and frequency-ordering best level and best tree representations of a physicochemical peptide series based on SURE and Shannon entropy criteria;

graphing said best level representation on a peptide best level graph, wherein the x-axis of said peptide best level graph indexes sequence position and the y-axis of said peptide best level graph is numbered in units of wavelet wavelengths, $\overline{\omega}$;

graphing said best tree representation on a peptide best tree graph, wherein the x-axis of said peptide best tree graph indexes sequence position and the y-axis of said peptide best tree graph is numbered in units of one of relative dilation (dd) and wavelet wavelengths, $\overline{\omega}$;

identifying a plurality of peptide maximal coefficient amplitudes, each of said plurality of peptide maximal coefficient amplitudes being derived from said peptide best level graph and said peptide best tree graph;

comparing said plurality of polypeptide maximal coefficient amplitudes to said plurality of peptide maximal coefficient amplitudes to determine if said plurality of polypeptide maximal coefficient amplitudes match said plurality of peptide maximal coefficient amplitudes, wherein a match between said plurality of polypeptide maximal coefficient amplitudes and said plurality of peptide maximal coefficient amplitudes indicates said peptide or peptide-like molecule may bind to and/or otherwise activate and/or inhibit the function of said target polypeptide or protein.

* * * * *